United States Patent
Boville et al.

(10) Patent No.: US 12,024,731 B2
(45) Date of Patent: *Jul. 2, 2024

(54) METHODS AND ENZYME CATALYSTS FOR THE SYNTHESIS OF NON-CANONICAL AMINO ACIDS

(71) Applicant: California Institute of Technology, Pasadena, CA (US)

(72) Inventors: Christina E. Boville, Pasadena, CA (US); Sabine Brinkmann-Chen, Glendale, CA (US); Andrew R. Buller, Pasadena, CA (US); David K. Romney, Pasadena, CA (US); Christopher K. Prier, Brooklyn, NY (US); Philipp Koch, Basel (CH); Remkes A. Scheele, Nijeveen (NL)

(73) Assignee: California Institute of Technology, Pasadena, CA (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/556,555

(22) Filed: Dec. 20, 2021

(65) Prior Publication Data
US 2022/0364130 A1    Nov. 17, 2022

Related U.S. Application Data

(60) Continuation of application No. 16/820,538, filed on Mar. 16, 2020, now Pat. No. 11,279,959, which is a division of application No. 15/970,674, filed on May 3, 2018, now Pat. No. 10,612,056.

(60) Provisional application No. 62/500,698, filed on May 3, 2017.

(51) Int. Cl.
| | |
|---|---|
| C12N 9/88 | (2006.01) |
| C07K 14/415 | (2006.01) |
| C12P 13/00 | (2006.01) |
| C12P 13/04 | (2006.01) |
| C12P 13/06 | (2006.01) |
| C12P 13/22 | (2006.01) |
| C12N 15/82 | (2006.01) |

(52) U.S. Cl.
CPC .......... *C12P 13/227* (2013.01); *C07K 14/415* (2013.01); *C12N 9/88* (2013.01); *C12P 13/005* (2013.01); *C12P 13/04* (2013.01); *C12P 13/06* (2013.01); *C12N 15/8254* (2013.01); *C12Y 402/0102* (2013.01)

(58) Field of Classification Search
CPC ............. C12N 9/1022; C12N 15/8254; C12N 9/0004; C12N 9/90; C12N 9/0006; C12P 17/10; C12P 13/227; C12Y 402/0102
USPC .......... 435/232, 108, 106, 116, 121
See application file for complete search history.

(56) References Cited

U.S. PATENT DOCUMENTS

| | | |
|---|---|---|
| 9,522,947 B2 | 12/2016 | Kawahata et al. |
| 10,513,719 B2 | 12/2019 | Buller et al. |
| 10,612,056 B2 | 4/2020 | Boville et al. |
| 10,752,927 B2 | 8/2020 | Boville et al. |
| 11,279,959 B2 | 3/2022 | Boville et al. |
| 2011/0183885 A1 | 7/2011 | Richelson et al. |
| 2016/0298152 A1 | 10/2016 | Buller et al. |
| 2018/0057806 A1 | 3/2018 | Romney et al. |

FOREIGN PATENT DOCUMENTS

| | | |
|---|---|---|
| DE | 3048318 A1 | 7/1982 |
| WO | 2018039495 A1 | 3/2018 |

OTHER PUBLICATIONS

Bruncko et al., "Cyclic Tautomers of Tryptophan: Enantio-and Diastereoselective Synthesis of β-Substituted and a, β-Disubstituted Derivatives of Tryptophan", The Journal of Organic Chemistry, vol. 59, Jan. 1, 1994, pp. 4239-4249.
EP18795135.5, "Partial Supplementary European Search Report", dated May 30, 2022, 12 pages.
Vekes E et al., "Indirect High-Performance Liquid Chromatographic Separation of Stereoisomers of β-alkyl-substituted Amino Acids by the Application of (S)-n-(4-Nitrophenoxycarbonyl)Phenylalanine Methoxyethyl Ester as Chiral Derivatizing Agent", Journal Of Chromatography A, vol. 949, No. 1-2, Mar. 8, 2002, pp. 125-139.
20190523-15970674 , "STN Search Report", 2019, pp. 1-154.
Boville et al., "Engineered Biosynthesis Of β-Alkyl Tryptophan Analogs", ChemRxiv, Available Online at: < https://authors.library.caltech.edu/88128/1/Boville_2018_ChemRxiv.pdf>, Aug. 14, 2018, 6 pages.
Boville et al., "Improved Synthesis of 4-Cyanotryptophan and Other Tryptophan Analogues in Aqueous Solvent Using Variants of TrpB From Thermotoga Maritima", The Journal of Organic Chemistry, vol. 83, No. 14, Jul. 20, 2018, pp. 7447-7452.
Buller et al., "Directed evolution of the tryptophan synthase β-subunit for stand-alone function recapitulates allosteric activation", Proceedings of National Academy of Sciences, vol. 112, Issue 47, Nov. 24, 2015, pp. 14599-14604.
Buller et al., "Tryptophan Synthase Uses an Atypical Mechanism to Achieve Substrate Specificity", Biochemistry, vol. 55, 2016, 11 pages.

(Continued)

*Primary Examiner* — Robert B Mondesi
*Assistant Examiner* — Mohammad Y Meah
(74) *Attorney, Agent, or Firm* — Kilpatrick Townsend & Stockton LLP

(57) ABSTRACT

The present disclosure provides methods for preparing β-substituted tryptophan compounds. The methods include: combining i) an unsubstituted indole or a substituted indole, ii) a β-substituted serine, and iii) a tryptophan synthase β-subunit (i.e., a TrpB); and maintaining the resulting mixture under conditions sufficient to form the β-substituted tryptophan. The TrpB contains at least one amino acid mutation which promotes formation of an amino-acrylate intermediate. New TrpB variants and new β-substituted tryptophan analogs are also described.

19 Claims, 12 Drawing Sheets

Specification includes a Sequence Listing.

(56) References Cited

OTHER PUBLICATIONS

Devos et al., "Practical Limits of Function Prediction", Proteins: Structure, Function, and Genetics, vol. 41, No. 1, Oct. 1, 2000, pp. 98-107.

Francis et al., "An Engineered Tryptophan Synthase Opens New Enzymatic Pathways to β-Methyltryptophan and Derivatives", ChemBioChem, vol. 18, No. 4, Feb. 16, 2017, pp. 382-386.

Herger et al., "Synthesis of β-Branched Tryptophan Analogs Using an Engineered Subunit of Tryptophan Synthase", Journal of the American Chemical Society, vol. 138, No. 27, Jul. 13, 2016, 11 pages.

Ilisz et al., "Enantioseparation of β-Substituted Tryptophan Analogues with Modified Cyclodextrins by Capillary Zone Electrophoresis", Journal of Chromatography A, vol. 1216, Issue 15, 2009, pp. 3360-3365.

Kalir et al., "Synthesis and Pharmacological Activity of Fluorinated Tryptamine Derivatives", Journal of Medicinal Chemistry, vol. 6, No. 6, Nov. 1, 1963, pp. 716-719.

Kisselev, "Polypeptide Release Factors in Prokaryotes and Eukaryotes: Same Function, Different Structure", Structure, vol. 10, Jan. 2002, pp. 8-9.

Murciano-Calles et al., "A Panel of TrpB Biocatalysts Derived from Tryptophan Synthase through the Transfer of Mutations that Mimic Allosteric Activation", Angewandte Chemie International Edition in English, vol. 55, No. 38, Sep. 12, 2016, pp. 11577-11581.

Murciano-Calles et al., "Directed Evolution of an Allosteric Tryptophan Synthase to Create a Platform for Synthesis of Noncanonical Amino Acids", Directed Enzyme Evolution: Advances and Applications, Feb. 15, 2017, pp. 1-16.

Nemes et al., "A Convenient Synthesis of Conformationally Constrained β-Substituted Tryptophans", Tetrahedron, vol. 56, No. 30, Jul. 21, 2000, pp. 5479-5492.

PCT/US2018/030951, "International Search Report and Written Opinion", dated Sep. 25, 2018, 8 pages.

Romney et al., "Unlocking Reactivity of TrpB: A General Biocatalytic Platform for Synthesis of Tryptophan Analogues", Journal of the American Chemical Society, vol. 139, No. 31, Aug. 9, 2017, pp. 10769-10776.

Whisstock et al., "Prediction of Protein Function from Protein Sequence and Structure", Quarterly Review of Biophysics, vol. 36, No. 3, Aug. 2003, pp. 307-340.

Witkowski et al., "Conversion of a β-Ketoacyl Synthase to a Malonyl Decarboxylase by Replacement of the Active-Site Cysteine with Glutamine", Biochemistry, vol. 38, 1999, pp. 11643-11650.

EP18795135.5, "Extended European Search Report", dated Aug. 30, 2022, 10 pages.

β-branched non-canonical amino acids

β-methylglutamine     4-hydroxyisoleucine     β-methyltryptophan

Products derived from β-branched tryptophan analogs

FR900452     Maremycin B     Herpes protease inhibitor
Inhibitor of platelet activation     Natural product Preparation of β-branched tryptophan analogs with PfTrpB

METHODS AND ENZYME CATALYSTS FOR THE SYNTHESIS OF NON-CANONICAL AMINO ACIDS

CROSS-REFERENCES TO RELATED APPLICATIONS

The present application is a continuation of U.S. patent application Ser. No. 16/820,538, U.S. patent Ser. No. 11/279,959 filed on Mar. 16, 2020, which is a division of U.S. patent application Ser. No. 15/970,674, U.S. patent Ser. No. 10/612,056, filed on May 3, 2018, which claims priority to U.S. Provisional Pat. Appl. No. 62/500,698, filed on May 3, 2017, which applications are incorporated herein by reference in their entirety.

STATEMENT AS TO RIGHTS TO INVENTIONS MADE UNDER FEDERALLY SPONSORED RESEARCH AND DEVELOPMENT

This invention was made with government support under Grant Nos. GM110851 and GM117635 awarded by the National Institutes of Health. The government has certain rights in the invention.

REFERENCE TO SUBMISSION OF A SEQUENCE LISTING AS A TEXT FILE

The Sequence Listing written in file SequenceListing 021320US.txt created on Jun. 25, 2018, 36,704 bytes, machine format IBM-PC, MS-Windows operating system, is hereby incorporated by reference in its entirety for all purposes.

BACKGROUND OF THE INVENTION

Amino acids are nature's premier synthetic building blocks for bioactive molecules. Alongside the standard proteinogenic amino acids are diverse non-canonical amino acids (ncAAs) that are structurally similar but contain unnatural functional groups that confer novel chemical properties. These ncAAs function as precursors to natural products and are useful synthetic building blocks found in 12% of the 200 top-grossing pharmaceuticals. Of special interest are β-branched ncAAs that possess a second chiral center at the β-position in addition to the chirality typically found at the α-position (FIG. 1A). The two adjacent stereocenters impose conformational constraints that affect the biochemical properties of both the amino acids themselves and the molecules that incorporate them, making β-branched ncAAs frequent components of useful natural products, biochemical probes, and therapeutics (FIG. 1B). Despite their broad utility, most β-branched ncAAs are not readily available due to the challenge of forming two adjacent stereocenters while tolerating the reactive functional groups present in amino acids. For example, traditional organic synthesis of β-methyltryptophan requires multiple steps that incorporate protecting groups, hazardous reagents, and expensive metal catalysts. To take full advantage of these bioactive molecules, a more efficient methodology is needed to synthesize β-branched ncAAs.

BRIEF SUMMARY OF THE INVENTION

Provided herein are methods for preparing β-substituted amino acids according to Formula I:

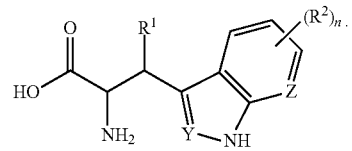

The methods include:
  combining i) an unsubstituted indole or a substituted indole, ii) a β-substituted serine, and iii) a tryptophan synthase β-subunit (i.e., a TrpB) comprising the amino acid sequence set forth in SEQ ID NO: 1 and further comprising at least one amino acid mutation, wherein the amino acid mutation promotes formation of an amino-acrylate intermediate; and
  maintaining the resulting mixture under conditions sufficient to form the β-substituted amino acid according to Formula I.

For compounds of Formula I:
  $R^1$ is $C_{2-8}$ alkyl, which is optionally substituted with one or more $R^{1a}$;
  each $R^{1a}$ is independently selected from the group consisting of halogen, —OH, —CN, —N$_3$, —NO$_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N($R^{1b}$)$_2$, —B(O$R^{1b}$)$_2$, —C(O)$R^{1c}$, —C(O)N($R^{1b}$)$_2$, —N$R^{1b}$C(O)$R^{1c}$, and —OC(O)$R^{1c}$;
  each $R^{1b}$ is independently selected from the group consisting of H and $C_{1-6}$ alkyl;
  each $R^{1c}$ is independently selected from the group consisting of H, —OH, halogen, $C_{1-6}$ alkyl, $C_{1-6}$ alkoxy;
  Y and Z are independently selected from the group consisting of CH, CR$^2$, and N;
  each $R^2$ is independently selected from the group consisting of halogen, —OH, —CN, —N$_3$, —NO$_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N($R^{2a}$)$_2$, —B(O$R^{2a}$)$_2$, —C(O)$R^{2b}$, —C(O)N($R^{2a}$)$_2$, —N$R^{2a}$C(O)$R^{2b}$, and —OC(O)$R^{2b}$;
  each $R^{2a}$ is independently selected from the group consisting of H and $C_{1-6}$ alkyl;
  each $R^{2b}$ is independently selected from the group consisting of H, —OH, halogen, $C_{1-6}$ alkyl, $C_{1-6}$ alkoxy; and
  subscript n is 0, 1, 2, or 3.
  In some embodiments, the TrpB contains a L161 mutation, such as an L161A mutation or an L161V mutation. The amino acid mutations can prevent hydrolysis and/or deamination of the amino-acrylate intermediate involved in tryptophan formation.

Also provided herein are new TrpB variants for preparing tryptophan analogs, as well as β-substituted tryptophans which can be used for the synthesis of pharmaceuticals, natural product derivatives/analogs, and tools for chemical biology.

DETAILED DESCRIPTION OF THE INVENTION

Introduction

Figure 1A:
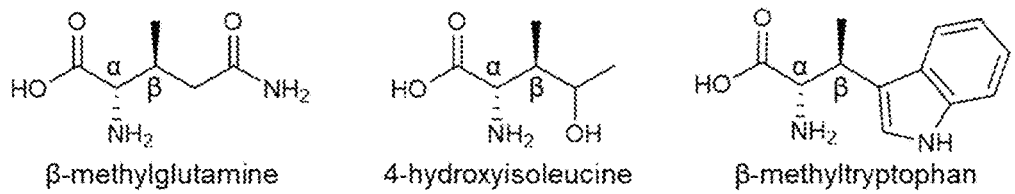
FIG. 1A shows β-branched ncAAs, which contain two adjacent stereocenters (α and β).
Figure 1B:
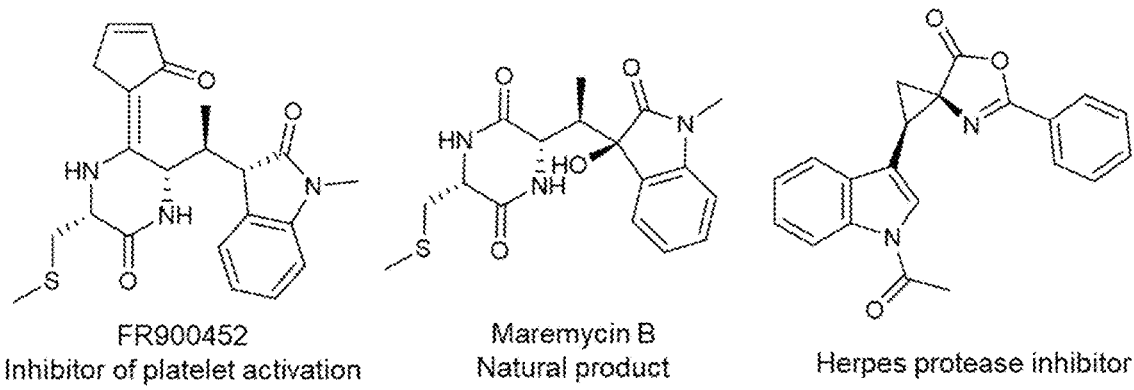
FIG. 1B shows natural products derived from β-branched tryptophan analogs.

Non-canonical amino acids (ncAAs) with dual stereocenters at the α and β positions are valuable precursors to natural products and therapeutics. Despite their bioactive potential, applications of such β-branched ncAAs are limited by their availability: synthesis requires inefficient, multi-step routes that often exhibit low overall stereoselectivity. Reported herein is the stereoselective biocatalytic synthesis of β-branched tryptophan analogs using an engineered variant of *Pyrococcus furiosus* tryptophan synthase (PfTrpB), PfTrpB$^{7E6}$. Compared to earlier catalysts, PfTrpB$^{7E6}$ displays greatly improved yields, granting access to challenging ncAAs. The utility of this biocatalyst is exemplified by the production of 27 enantiopure β-branched tryptophan analogs, 20 of which are previously unreported. The molecular basis for the efficient catalysis and versatile substrate scope was explored through X-ray crystallography and UV-visible light spectroscopy, which revealed that a combination of active-site and remote mutations increases the abundance and persistence of a key reactive intermediate. This enzyme provides an operationally simple and environmentally benign platform for preparation of β-branched tryptophan building blocks.

Demonstrated herein is a biocatalytic route to (2S, 3S)-β-tryptophan analogs using the engineered thermostable catalyst, PfTrpB$^{7E6}$. Through directed evolution, the abundance and persistence of the key E(A-A) intermediate was increased by the introduction of active-site and remote mutations. In turn, PfTrpB$^{7E6}$ displays improved yields and coupling efficiencies with an array of β-alkyl Ser analogs and highlights the applicability of engineered biocatalysts to produce desirable β-branched synthetic building blocks on a preparative scale.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the reagent" includes reference to one or more reagents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The terms "tryptophan synthase β-subunit" and "TrpB" refer to a polypeptide (EC 4.2.1.20) that catalyzes the formation of tryptophan from serine (unsubstituted or substituted) and indole (unsubstituted or substituted). Tryptophan synthases are absent in animals, but they are expressed in a variety of species of plants, eubacteria, archaebacteria, protista, and fungi. The β subunit catalyzes the condensation of indole and serine to form tryptophan in a PLP-dependent reaction.

The term "indole," by itself or as part of another functional group, refers to 2,3-benzopyrrole and substituted analogs thereof. Unless otherwise specified, substituted indoles can be substituted with one or more moieties selected from halo, hydroxy, amino, alkylamino, alkoxy, haloalkyl, carboxy, amido, nitro, oxo, and cyano.

The term "β-substituted serine" refers to a 2-amino-3-hydroxypropanoic acid having an alkyl substituent covalently bonded to the 3-carbon (i.e., in the β position with respect to the carboxylate functional group). The alkyl substituent can be further substituted as described below.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Alkyl groups can be unsubstituted or substituted. Unless otherwise specified, "substituted alkyl" groups can be substituted with one or more moieties selected from halo, hydroxy, amino, alkylamino, alkoxy, haloalkyl, carboxy, amido, nitro, oxo, and cyano.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be unsubstituted or substituted. Unless otherwise specified, "substituted alkenyl" groups can be substituted with one or more moieties selected from halo, hydroxy, amino, alkylamino, alkoxy, haloalkyl, carboxy, amido, nitro, oxo, and cyano.

As used herein, the term "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be unsubstituted or substituted. Unless otherwise specified, "substituted alkynyl" groups can be substituted with one or more moieties selected from halo, hydroxy, amino, alkylamino, alkoxy, haloalkyl, carboxy, amido, nitro, oxo, and cyano.

As used herein, the term "aryl" refers to an aromatic carbon ring system having any suitable number of ring atoms and any suitable number of rings. Aryl groups can include any suitable number of carbon ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be unsubstituted or substituted. Unless otherwise specified, "substituted aryl" groups can be substituted with one or more moieties selected from halo, hydroxy, amino, alkylamino, alkoxy, haloalkyl, carboxy, amido, nitro, oxo, and cyano.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Cycloalkyl groups can be unsubstituted or substituted. Unless otherwise specified, "substituted cycloalkyl" groups can be substituted with one or more moieties selected from halo, hydroxy, amino, alkylamino, alkoxy, haloalkyl, carboxy, amido, nitro, oxo, and cyano.

As used herein, the term "heterocyclyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 4 to 6, or 4 to 7 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. Examples of heterocyclyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocyclyl groups can be unsubstituted or substituted. Unless otherwise specified, "substituted heterocyclyl" groups can be substituted with one or more moieties selected from halo, hydroxy, amino, alkylamino, alkoxy, haloalkyl, carboxy, amido, nitro, oxo, and cyano.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms including, but not limited to, B, Al, Si and P can also be present in a heteroaryl group. The heteroatoms can be oxidized to form moieties such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. Examples of heteroaryl groups include, but are not limited to, pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. Heteroaryl groups can be unsubstituted or substituted. Unless otherwise specified, "substituted heteroaryl" groups can be substituted with one or more moieties selected from halo, hydroxy, amino, alkylamino, alkoxy, haloalkyl, carboxy, amido, nitro, oxo, and cyano.

As used herein, the term "alkoxy" refers to an alkyl group having an oxygen atom that connects the alkyl group to the point of attachment: i.e., alkyl-O—. As for alkyl group, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups can be unsubstituted or substituted. Unless otherwise specified, "substituted alkoxy" groups can be substituted with one or more moieties selected from halo, hydroxy, amino, alkylamino, alkoxy, haloalkyl, carboxy, amido, nitro, oxo, and cyano.

As used herein, the term "alkylthio" refers to an alkyl group having a sulfur atom that connects the alkyl group to the point of attachment: i.e., alkyl-S—. As for alkyl groups, alkylthio groups can have any suitable number of carbon atoms, such as $C_{1-6}$ or $C_{1-4}$. Alkylthio groups include, for example, methoxy, ethoxy, propoxy, iso-propoxy, butoxy, 2-butoxy, iso-butoxy, sec-butoxy, tert-butoxy, pentoxy, hexoxy, etc. groups can be unsubstituted or substituted.

Unless otherwise specified, "substituted alkylthio" groups can be substituted with one or more moieties selected from halo, hydroxy, amino, alkylamino, alkoxy, haloalkyl, carboxy, amido, nitro, oxo, and cyano.

As used herein, the term "heteroalkyl" refers to an alkyl group having one or more non-adjacent methylene (i.e., $CH_2$) units that is replaced by O, S, or NH. A carbon atom is the point of attachment for the heteroalkyl group to the remainder of the molecule, but the methylene replacement can occur at any other point along the carbon backbone. In the case of oxygen for example, replacement of $CH_2$ can occur in the middle of an alkyl group (e.g., in the middle of a propyl group, forming methoxymethyl with the formula $CH_3OCH_2$—) or at the end of the alkyl group (e.g., at the end of the propyl group, forming hydroxyethyl with the formula $HOCH_2CH_2$—).

As used herein, the terms "halo" and "halogen" refer to fluorine, chlorine, bromine and iodine.

As used herein, the term "haloalkyl" refers to an alkyl moiety as defined above substituted with at least one halogen atom.

As used herein, the term "alkylsilyl" refers to a moiety —$SiR_3$, wherein at least one R group is alkyl and the other R groups are H or alkyl. The alkyl groups can be substituted with one more halogen atoms.

As used herein, the term "acyl" refers to a moiety —C(O)R, wherein R is an alkyl group.

As used herein, the term "oxo" refers to an oxygen atom that is double-bonded to a compound (i.e., O=).

As used herein, the term "carboxy" refers to a moiety —C(O)OH. The carboxy moiety can be ionized to form the carboxylate anion. "Alkyl carboxylate" refers to a moiety —C(O)OR, wherein R is an alkyl group as defined herein.

As used herein, the term "amino" refers to a moiety —$NR_3$, wherein each R group is H or alkyl.

As used herein, the term "amido" refers to a moiety —NRC(O)R or —C(O)$NR_2$, wherein each R group is H or alkyl.

As used herein, the term "protecting group" refers to a chemical moiety that renders a functional group such as an amine or carboxylic acid unreactive, but is also removable so as to restore the reactive functional group. Examples of protecting groups include, but are not limited to, benzyloxycarbonyl; 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other protecting groups are known to those of skill in the art including, for example, those described by Green and Wuts (*Protective Groups in Organic Synthesis*, 4th Ed. 2007, Wiley-Interscience, New York).

The terms "protein," "peptide," and "polypeptide" are used interchangeably herein to refer to a polymer of amino acid residues, or an assembly of multiple polymers of amino acid residues. The terms apply to amino acid polymers in which one or more amino acid residues are an artificial chemical mimic of a corresponding naturally occurring amino acid, as well as to naturally occurring amino acid polymers and non-naturally occurring amino acid polymers.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an a carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins,* 1993).

The term "oligonucleotide," "nucleic acid," "nucleotide," or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19: 5081 (1991), Ohtsuka et al., *J. Biol. Chem.* 260: 2605-2608 (1985), and Rossolini et al., *Mol. Cell. Probes* 8: 91-98 (1994)). The term nucleic acid is used interchangeably with gene, cDNA, and mRNA encoded by a gene.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, for example, BLAST and BLAST 2.0 algorithms can be used, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The BLAST algorithms provide a statistical analysis of the similarity between two sequences (see, e.g., Karlin and Altschul, *Proc. Nat'l. Acad. Sci. USA,* 90: 5873-5787 (1993)). One measure of similarity provided by the BLAST algorithm is the smallest sum probability (P(N)), which provides an indication of the probability by which a match between two nucleotide or amino acid sequences would occur by chance.

The term "site-directed mutagenesis" refers to various methods in which specific changes are intentionally made introduced into a nucleotide sequence (i.e., specific nucleotide changes are introduced at pre-determined locations). Known methods of performing site-directed mutagenesis include, but are not limited to, PCR site-directed mutagenesis, cassette mutagenesis, whole plasmid mutagenesis, and Kunkel's method.

The term "site-saturation mutagenesis," also known as "saturation mutagenesis," refers to a method of introducing random mutations at predetermined locations with a nucleotide sequence, and is a method commonly used in the context of directed evolution (e.g., the optimization of proteins (e.g., in order to enhance activity, stability, and/or stability), metabolic pathways, and genomes). In site-saturation mutagenesis, artificial gene sequences are synthesized using one or more primers that contain degenerate codons; these degenerate codons introduce variability into the position(s) being optimized. Each of the three positions within a degenerate codon encodes a base such as adenine (A), cytosine (C), thymine (T), or guanine (G), or encodes a degenerate position such as K (which can be G or T), M (which can be A or C), R (which can be A or G), S (which can be C or G), W (which can be A or T), Y (which can be C or T), B (which can be C, G, or T), D (which can be A, G, or T), H (which can be A, C, or T), V (which can be A, C, or G), or N (which can be A, C, G, or T). Thus, as a non-limiting example, the degenerate codon NDT encodes an A, C, G, or T at the first position, an A, G, or T at the second position, and a T at the third position. This particular combination of 12 codons represents 12 amino acids (Phe, Leu, Ile, Val, Tyr, His, Asn, Asp, Cys, Arg, Ser, and Gly). As another non-limiting example, the degenerate codon VHG encodes an A, C, or G at the first position, an A, C, or T at the second position, and G at the third position. This particular combination of 9 codons represents 8 amino acids (Lys, Thr, Met, Glu, Pro, Leu, Ala, and Val). As another non-limiting example, the "fully randomized" degenerate codon NNN includes all 64 codons and represents all 20 naturally-occurring amino acids.

In some instances, a mixture of degenerate primers is used. A mixture of degenerate primers can contain any number of different degenerate primers in any ratio. As a non-limiting example, a mixture of primers containing the NDT, VHG, and TGG primers can be used. Such a mixture can contain, for example, an amount of each primer in a 12:9:1 ratio (e.g., a NDT:VHG:TGG ratio of 12:9:1). Based on various considerations, non-limiting examples being desired redundancy, the desired presence of stop codons, and/or desired amino acid characteristics (e.g., the presence of nonpolar residues, charged residues, or small side chain residues), different combinations of degenerate primers can be used. Considerations and methods for choosing optimal combinations of degenerate primers will be known to one of skill in the art.

The term "nucleotide sequence encoding a peptide" means the segment of DNA involved in producing a peptide chain. The term can include regions preceding and following the coding region (leader and trailer) involved in the transcription/translation of a gene product and the regulation of the transcription/translation, as well as intervening sequences (introns) between individual coding segments (exons).

The term "homolog," as used herein with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In particular embodiments, the homology between two proteins is indicative of its shared ancestry, related by evolution.

III. Methods for Preparation of Non-Canonical Tryptophan Compounds

Provided herein are methods for preparing β-substituted amino acids according to Formula I:

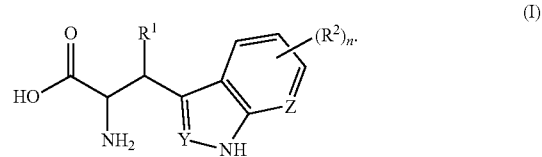

The methods include:
combining i) an unsubstituted indole or a substituted indole, ii) a β-substituted serine, and iii) a tryptophan synthase β-subunit comprising the amino acid sequence set forth in SEQ ID NO: 1 and further comprising at least one amino acid mutation, wherein the amino acid mutation promotes formation of an amino-acrylate intermediate; and
maintaining the resulting mixture under conditions sufficient to form the β-substituted amino acid according to Formula I;
wherein:
$R^1$ is $C_{2-8}$ alkyl, which is optionally substituted with one or more $R^{1a}$;
each $R^{1a}$ is independently selected from the group consisting of halogen, —OH, —CN, —N$_3$, —NO$_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N(R$^{1b}$b)$_2$, —B(OR$^{1b}$)$_2$, —C(O)R$^{1c}$, —C(O)N(R$^{1b}$)$_2$, —NR$^{1b}$C(O)R$^{1c}$, and —OC(O)R$^{1c}$;
each $R^{1b}$ is independently selected from the group consisting of H and $C_{1-6}$ alkyl;
each $R^{1c}$ is independently selected from the group consisting of H, —OH, halogen, $C_{1-6}$ alkyl, $C_{1-6}$ alkoxy;

Y and Z are independently selected from the group consisting of CH, CR², and N;

each R² is independently selected from the group consisting of halogen, —OH, —CN, —N₃, —NO₂, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N(R²ᵃ)₂, —B(OR²ᵃ)₂, —C(O)R²ᵇ, —C(O)N(R²ᵃ)₂, NR²ᵃC(O)R²ᵇ, and —OC(O)R²ᵇ;

each R²ᵃ is independently selected from the group consisting of H and $C_{1-6}$ alkyl;

each R²ᵇ is independently selected from the group consisting of H, —OH, halogen, $C_{1-6}$ alkyl, $C_{1-6}$ alkoxy; and subscript n is 0, 1, 2, or 3.

Tryptophan synthase (TrpS; EC 4.2.1.20) is a heterodimeric complex that catalyzes the formation of L-tryptophan (Trp) from L-serine (Ser) and indole glycerol phosphate (IGP). TrpS is a naturally promiscuous enzyme complex catalyzing β-substitution reactions with haloindoles, methylindoles, and aminoindoles, along with an assortment of nonindole nucleophiles for C—S and C—N bond formation. Such ncAAs have diverse applications in chemical biology, serve as intermediates in the synthesis of natural products, and are privileged scaffolds for the development of pharmaceuticals.

The catalytic mechanism has been extensively studied for TrpS from *Escherichia coli* and *Salmonella typhimurium*, where it has been shown that the enzyme consists of two subunits, TrpA (α-subunit) and TrpB (β-subunit), both of which have low catalytic efficiencies in isolation. The activities of both subunits increase upon complex formation and are further regulated by an intricate and well-studied allosteric mechanism. IGP binding to the α-subunit stimulates pyridoxal phosphate (PLP)-dependent amino-acrylate formation in the β-subunit [E(A-A)], which in turn promotes retro-aldol cleavage of IGP in the α-subunit, releasing indole. Indole reacts with E(A-A) in a C—C bond-forming reaction, yielding L-tryptophan as product. These allosteric effects are mediated through the rigid-body motion of the communication (COMM) domain and a monovalent cation (MVC) binding site within the β-subunit, which undergo complex conformational transitions associated with open, partially closed, and fully closed states during the catalytic cycle.

Despite its natural ability to produce these desirable compounds, TrpS has enjoyed only limited application. Optimized methods are restricted by low substrate concentrations and yields typically below 50%. To produce ncAAs, researchers have used the *S. typhimurium* TrpS complex (StTrpS), which suffers from poor thermostability and low tolerance to organic solvents.

Tryptophan synthase is typically found as a bi-enzyme complex linearly arranged. In *S. typhimurium*, the smaller α-subunit (27 kDa) adopts a TIM β/α barrel. The PLP-dependent β-subunit (43 kDa) is of a fold type II conformation and features a monovalent cation-binding site adjacent to its catalytic center. The active sites of the subunits are interconnected by a substrate tunnel for efficient channeling of the common metabolite, indole. A great degree of allosteric regulation by an intricate network of interactions is necessary to synchronize the catalytic activities in the spatially separated active sites of the tryptophan synthase complex. A variety of analytical tools have been employed to gain a more detailed mechanical and chemical understanding of the allosteric regulation mechanisms involved in catalysis, including biochemical solution experiments, mutational studies, and X-ray crystallography. The most essential feature allowing for the high enzymatic efficiency of tryptophan synthase is the direct channeling of the common intermediate, indole, through the hydrophobic 25-Å long substrate tunnel interconnecting the active sites of the subunits. Two alpha subunits and two beta subunits, referred to as TrpA (tryptophan-α) and TrpB (tryptophan-β), form an α-ββ-α complex. The αsubunit has a TIM barrel conformation. The β subunit has a fold type II conformation and a binding site adjacent to the active site for monovalent cations. Their assembly into a complex leads to structural changes in both subunits resulting in reciprocal activation. There are two main mechanisms for intersubunit communication. First, the COMM domain of the β-subunit and the α-loop2 of the α-subunit interact. Additionally, there are interactions between the αGly181 and βSer178 residues. The active sites are regulated allosterically and undergo transitions between open, inactive, and closed, active, states.

Figure 1C:
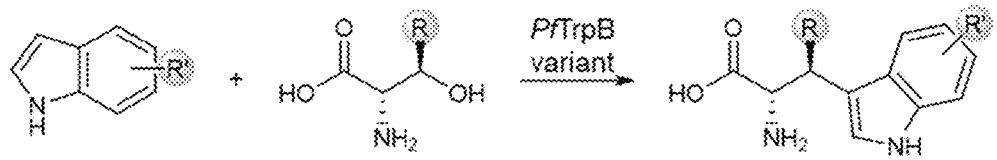
FIG. 1C shows engineered PfTrpB employed in a simple and stereoselective approach to synthesize β-branched tryptophan analogs.

The β-subunit of tryptophan synthase from the thermophilic organism *Pyrococcus furiosus* (PfTrpB) has been engineered as a stand-alone ncAA synthase able to generate tryptophan (Trp) analogs from serine (Ser) and the corresponding substituted indole (FIG. 1C). See, Buller (*Proc. Natl. Acad. Sci. U.S.A.* 112, 14599-14604 (2015)); Romney (*J. Am. Chem. Soc.* 139, 10769-10776 (2017)); Murciano-Calles (*Angew. Chem. Int. Ed.* 55, 11577-11581 (2016). Further engineering of PfTrpB for improved C—C bond formation with indole analogs and threonine (Thr) led to PfTrpB²ᴮ⁹ (eight mutations from wild-type PfTrpB), which exhibited a >1,000-fold improvement in (2S, 3S)-β-methyltryptophan (β-MeTrp) production relative to PfTrpB. See, Buller (*Biochemistry* 55, 7043-7046 (2016)); Herger, (*J. Am. Chem. Soc.* 138, 8388-8391 (2016)).

In some embodiments, the TrpB is an engineered variant comprising one or more mutation(s). In some instances, the mutation is a substitution of the native residue with Ala, Asp, Arg, Asn, Cys, Glu, Gin, Gly, His, Ile, Lys, Leu, Met, Phe, Pro, Ser, Thr, Trp, Tyr, or Val. In some embodiments, the TrpB variant is a chimeric protein comprising recombined sequences or blocks of amino acids from two, three, or more different proteins. As described herein, TrpBs can be improved through the introduction of mutations which alter the amino acid sequence of the polypeptide so as to generate a catalyst that is highly productive and selective for the desired product-forming reaction.

The development of the methods disclosed herein was guided, in part, by the discovery that the activity of TrpB catalysts can be improved by introducing amino acid mutations that promote the formation and/or persistence of the amino-acrylate intermediate in the TrpB catalytic cycle. As used herein, the terms "amino-acrylate intermediate" and "E(A-A) intermediate" refer to a 4-substituted (E)-2-(((E)-(2-methyl-3-oxido-5-((phosphonooxy)-methyl)pyridin-4-yl)methylene)ammonio)but-2-enoate species according to Formula A-A:

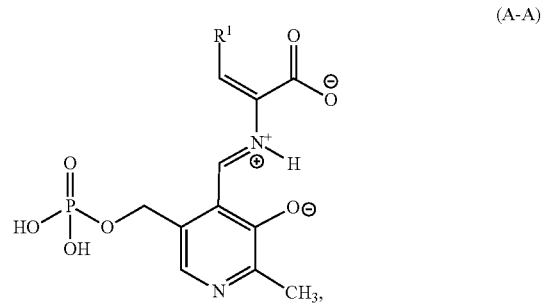

wherein R¹ is $C_{2-8}$ alkyl, which is optionally substituted with one or more $R^{1a}$ as described above. One of skill in the art will appreciate that the amino-acrylate intermediate can exist in different tautomeric forms, where the ionizable functional groups (i.e., carboxylate, phosphate, phenolate, iminium) are protonated or deprotonated.

Mutational methods of generating diversity include, for example, site-directed mutagenesis (Ling et al. (1997) *Anal Biochem.* 254(2): 157-178; Dale et al. (1996) *Methods Mol. Biol.* 57: 369-374; Smith (1985) *Ann. Rev. Genet.* 19: 423-462; Botstein & Shortle (1985) *Science* 229: 1193-1201; Carter (1986) *Biochem. J.* 237: 1-7; and Kunkel (1987) in *Nucleic Acids & Molecular Biology* (Eckstein, F. and Lilley, D. M. J. eds., Springer Verlag, Berlin)); mutagenesis using uracil containing templates (Kunkel (1985) *Proc. Natl. Acad. Sci. USA* 82: 488-492; Kunkel et al. (1987) *Methods in Enzymol.* 154, 367-382; and Bass et al. (1988) *Science* 242: 240-245); oligonucleotide-directed mutagenesis (*Methods in Enzymol.* 100: 468-500 (1983); *Methods in Enzymol.* 154: 329-350 (1987); Zoller & Smith (1982) *Nucleic Acids Res.* 10:6487-6500; Zoller & Smith (1983) *Methods in Enzymol.* 100: 468-500; and Zoller & Smith (1987) *Methods in Enzymol.* 154: 329-350); phosphorothioate-modified DNA mutagenesis (Taylor et al. (1985) *Nucl. Acids Res.* 13: 8749-8764; Taylor et al. (1985) *Nucl. Acids Res.* 13: 8765-8787; Nakamaye & Eckstein (1986) *Nucl. Acids Res.* 14: 9679-9698; Sayers et al. (1988) *Nucl. Acids Res.* 16: 791-802; and Sayers et al. (1988) *Nucl. Acids Res.* 16: 803-814); mutagenesis using gapped duplex DNA (Kramer et al. (1984) *Nucl. Acids Res.* 12: 9441-9456; Kramer & Fritz (1987) *Methods in Enzymol.* 154: 350-367; Kramer et al. (1988) *Nucl. Acids Res.* 16: 7207; and Fritz et al. (1988) *Nucl. Acids Res.* 16: 6987-6999).

Additional suitable methods include point mismatch repair (Kramer et al. (1984) *Cell* 38: 879-887), mutagenesis using repair-deficient host strains (Carter et al. (1985) *Nucl. Acids Res.* 13: 4431-4443; and Carter (1987) *Methods in Enzymol.* 154: 382-403), deletion mutagenesis (Eghtedarzadeh & Henikoff (1986) *Nucl. Acids Res.* 14: 5115), restriction-selection and restriction-purification (Wells et al. (1986) *Phil. Trans. R. Soc. Lond. A* 317: 415-423), mutagenesis by total gene synthesis (Nambiar et al. (1984) *Science* 223: 1299-1301; Sakamar & Khorana (1988) *Nucl. Acids Res.* 14: 6361-6372; Wells et al. (1985) *Gene* 34: 315-323; and Grundstrom et al. (1985) *Nucl. Acids Res.* 13: 3305-3316); double-strand break repair (Mandecki (1986); Arnold (1993) *Current Opinion in Biotechnology* 4: 450-455; and *Proc. Natl. Acad. Sci. USA,* 83:7177-7181).

Additional details regarding various diversity generating methods can be found in the following U.S. patents, PCT publications, and EPO publications: U.S. Pat. No. 5,605,793 to Stemmer (Feb. 25, 1997), U.S. Pat. No. 5,811,238 to Stemmer et al. (Sep. 22, 1998) U.S. Pat. No. 5,830,721 to Stemmer et al. (Nov. 3, 1998), U.S. Pat. No. 5,834,252 to Stemmer, et al. (Nov. 10, 1998) U.S. Pat. No. 5,837,458 to Minshull, et al. (Nov. 17, 1998), WO 95/22625, Stemmer and Crameri, WO 96/33207 by Stemmer and Lipschutz, WO 97/20078 by Stemmer and Crameri; WO 97/35966 by Minshull and Stemmer, WO 99/41402 by Punnonen et al., WO 99/41383 by Punnonen et al., WO 99/41369 by Punnonen et al., WO 99/41368 by Punnonen et al., EP 752008 by Stemmer and Crameri, EP 0932670 by Stemmer, WO 99/23107 by Stemmer et al., WO 99/21979 by Apt et al., WO 98/31837 by del Cardayre et al., WO 98/27230 by Patten and Stemmer, WO 98/13487 by Stemmer et al., WO 00/00632, WO 00/09679, WO 98/42832 by Arnold et al., WO 99/29902 by Arnold et al., WO 98/41653 by Vind, WO 98/41622 by Borchert et al., WO 98/42727 by Pati and Zarling, WO 00/18906 by Patten et al., WO 00/04190 by del Cardayre et al., WO 00/42561 by Crameri et al., WO 00/42559 by Selifonov and Stemmer, WO 00/42560 by Selifonov et al., WO 01/23401 by Welch et al., and WO 01/64864 by Affholter.

In some embodiments, the TrpB mutation prevents hydrolysis of the amino-acrylate intermediate. In some embodiments, the amino acid mutation reduces deamination of the amino-acrylate intermediate. The competitive hydrolysis/deamination process is depicted in FIG. 2B. The effects of a particular mutation can be assessed spectroscopically as described in detail below. For example, incubation of TrpB with a β-substituted serine leads to formation of the amino-acrylate intermediate and a detectable absorbance at 350 nm. Hydrolysis of the amino-acrylate intermediate can result in a partial or complete loss of the absorbance at 350 nm. Deamination of the hydrolyzed amino-acrylate, in turn, results in the formation of an α-keto acid having a distinct, detectable absorbance at 320 nm. Accordingly, the effects of a particular mutation in promoting formation of the amino-acrylate intermediate and/or its persistence during the TrpB catalytic cycle can be readily determined by assessing the absorbance spectrum of a mixture containing the TrpB and the β-substituted serine. This can include measuring the absorbance at 350 nm (e.g., observing an increase in absorbance at 350 nm) and/or measuring the absorbance at 320 nm (e.g., finding that the absorbance at 320 nm does not increase with time).

In some embodiments, the tryptophan synthase β-subunit includes an L161 mutation. The L161 mutation can be, for example, L161A or L161V.

In some embodiments, the tryptophan synthase β-subunit further comprises one or more mutations selected from the group consisting of a V68 mutation, an L91 mutation, an M139 mutation, an N166 mutation, a V173 mutation, an H275 mutation, an A321 mutation, and an S335 mutation.

In some embodiments, the tryptophan synthase β-subunit comprises the amino acid sequence set forth in any one of SEQ ID NOS:2-5.

In some embodiments, the tryptophan synthase β-subunit comprises the amino acid sequence set forth in SEQ ID NO:4.

In some embodiments, the TrpB comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to any of the amino acid sequences described herein (e.g., any of the amino acid sequences set forth in SEQ ID NOS:2-5). In other embodiments, the TrpB comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to any of the amino acid sequences described herein. In particular embodiments, the TrpB comprises an amino acid sequence that has about 90% or greater (e.g., about 90%, 91%, 92%, 93%, 94%, 95%, 96%, 97%, 98%, 99%, or 100%) identity any of the amino acid sequences described herein. In some instances, the TrpB comprises an amino acid sequence that is about 95%, 96%, 97%, 98%, 99%, or 100% identical any of the amino acid sequences described herein. In some embodiments, the TrpB variants are used without the N-terminal methionine residues set forth in SEQ ID NOS:2-5.

In some embodiments, the TrpB comprises an amino acid sequence that contains at least about between about 5 and 385 (e.g., about 5, 10, 15, 20, 25, 30, 35, 40, 45, 50, 55, 60, 65, 70, 80, 90, 100, 105, 110, 115, 120, 125, 135, 140, 145, 150, 155, 160, 165, 170, 175, 180, 185, 190, 195, 200, 205, 210, 215, 220, 225, 235, 240, 245, 250, 255, 260, 265, 270, 275, 280, 285, 290, 295, 300, 305, 310, 315, 320, 325, 335, 340, 345, 350, 355, 360, 365, 370, 375, 380, or 385) of the amino acids in SEQ ID NOS:2-5, or variants thereof as described above. The amino acids may be contiguous, or separated by any number of amino acids.

The TrpB may contain further mutations for enhancement of activity, depending in part on factors such as the particular indole or particular β-substituted serine being employed. In some embodiments, the TrpB may contain one or more mutations at one or more of positions 104, 144, 165, 183, 186, 212, and 301 in SEQ ID NO:2, SEQ ID NO:3, SEQ ID NO:4, or SEQ ID NO:5. The TrpB may contain, for example, an E104G mutation, an M144T mutation, an I165F mutation, an I183F mutation, a V186A mutation, an L212P mutation, and/or a Y301H mutation. Such mutations can be particularly useful for enhancing activity with variously substituted indoles as described Romney, et al. in in US 2018/0057806. In some embodiments, the TrpB may contain mutations at one or both of positions 28 and 227 in SEQ ID NO:2, SEQ ID NO:3, SEQ ID NO:4, or SEQ ID NO:5. The TrpB may include, for example, an R28G mutation or a G227S mutation as described by Boville et al. (JOC, 2018). In some embodiments, the TrpB further includes on or more mutations selected from an E104 mutation, a G106 mutation, an A107 mutation, an S185 mutation, a G298 mutation, a D300 mutation, and/or a Y301 mutation.

Tryptophan synthases from other organisms can be engineered with mutations as described above, at the amino acid positions corresponding to the analogous sites in *P. furiosus*. TrpB sequences are typically characterized by two domains which are approximately equivalent in size, each having a helix/sheet/helix fold, with the PLP binding site located in the interface between the two domains; see, e.g., Hyde, et al. (*J. Biol. Chem.* 1988. 263: 17857-17871) and Ro, et al. (*J. Biol. Chem.* 1999. 274: 36439-36445), which are incorporated herein by reference in their entirety. TrpBs from *T. maritima* (SEQ ID NO:7), *A. fulgidus* (SEQ ID NO:8), or *E. coli* (SEQ ID NO:9), for example, can also be engineered for synthesis of β-substituted tryptophan analogs. The TrpB from *S. typhimurium* TrpB (UniProt Accession No. P0A2K1), and variants thereof, can also be employed for the synthesis of β-substituted tryptophan analogs. The TrpB can be an *A. cryptum* TrpB (e.g., UniProt Accession No. A5FY57), an *A. ferrooxidans* TrpB (e.g., UniProt Accession No. B7J4S9), an *A. citrulli* TrpB (e.g., UniProt Accession No. A1TLG8), an *A. baylyi* TrpB (e.g., UniProt Accession No. Q6FEF1), an *A. pleuropneumoniae* TrpB (e.g., UniProt Accession No. B0BU72), an *A. succinogenes* TrpB (e.g., UniProt Accession No. A6VPD9), an *A. hydrophila* TrpB (e.g., UniProt Accession No. A0KMD0), an *A. salmonicida* TrpB (e.g., UniProt Accession No. A4SKT1), an *A. fabrum* TrpB (e.g., UniProt Accession No. Q8UJB0), an *A. radiobacter* TrpB (e.g., UniProt Accession No. B9JG43), an *A. vitis* TrpB (e.g., UniProt Accession No. B9JXV6), an *A. salmonicida* TrpB (e.g., UniProt Accession No. B6EJA3), an *A. metalliredigens* TrpB (e.g., UniProt Accession No. A6TM76), an *A. mediterranea* TrpB (e.g., UniProt Accession No. B4S1J4), an *A. variabilis* TrpB (e.g., UniProt Accession No. Q3MBV3), an *A. flavithermus* TrpB (e.g., UniProt Accession No. B7GHQ9), an *A. pseudotrichonymphae* TrpB (e.g., UniProt Accession No. B6YQ32), an *A. vinelandii* TrpB (e.g., UniProt Accession No. C1DH66), a *B. anthracis* TrpB (e.g., UniProt Accession No. Q81TL8), a *B. cereus* TrpB (e.g., UniProt Accession No. C1ELF0), a *B. clausii* TrpB (e.g., UniProt Accession No. Q5WGS1), a *B. halodurans* TrpB (e.g., UniProt Accession No. Q9KCB0), a *B. licheniformis* TrpB (e.g., UniProt Accession No. Q65I35), a *B. pumilus* TrpB (e.g., UniProt Accession No. A8FEJ8), a *B. subtilis* TrpB (e.g., UniProt Accession No. P07600), a *B. thuringiensis* TrpB (e.g., UniProt Accession No. A0RB64), a *B. velezensis* TrpB (e.g., UniProt Accession No. A7Z616), a *B. weihenstephanensis* TrpB (e.g., UniProt Accession No. A9VJW2), a *B. fragilis* TrpB (e.g., UniProt Accession No. Q5LBZ8), a *B. thetaiotaomicron* TrpB (e.g., UniProt Accession No. Q8AAD2), a *B. vulgatus* TrpB (e.g., UniProt Accession No. A6L7M5), a *B. indica* TrpB (e.g., UniProt Accession No. B2IF48), a *B. floridanus* TrpB (e.g., UniProt Accession No. Q7VR00), a *B. pennsylvanicus* TrpB (e.g., UniProt Accession No. Q492N6), a *B. bronchiseptica* TrpB (e.g., UniProt Accession No. Q7WD04), a *B. parapertussis* TrpB (e.g., UniProt Accession No. Q7W5G8), a *B. pertussis* TrpB (e.g., UniProt Accession No. Q7VTF1), a *B. petrii* TrpB (e.g., UniProt Accession No. A9IIE0), a *B. diazoefficiens* TrpB (e.g., UniProt Accession No. Q89WE5), a *B. abortus* TrpB (e.g., UniProt Accession No. Q2YQW5), a *B. canis* TrpB (e.g., UniProt Accession No. A9M9U2), a *B. melitensis* TrpB (e.g., UniProt Accession No. Q8YE60), a *B. suis* TrpB (e.g., UniProt Accession No. B0CJK8), a *B. aphidicola* TrpB (e.g., UniProt Accession No. Q44685), a *C. subterraneus* TrpB (e.g., UniProt Accession No. Q8R9M9), a *C. jejuni* TrpB (e.g., UniProt Accession No. Q5HWB9), a *C. vibrioides* TrpB (e.g., UniProt Accession No. P12290), a *C. trachomatis* TrpB (e.g., UniProt Accession No. O84172), a *C. tepidum* TrpB (e.g., UniProt Accession No. Q8KF11), a *C. violaceum* TrpB (e.g., UniProt Accession No. Q7NUD8), a *C. koseri* TrpB (e.g., UniProt Accession No. A8AG61), a *C. michiganensis* TrpB (e.g., UniProt Accession No. A5CRV6), a *C. acetobutylicum* TrpB (e.g., UniProt Accession No. Q97EF5), a *C. beijerinckii* TrpB (e.g., UniProt Accession No. A6LU96), a *C. botulinum* TrpB (e.g., UniProt Accession No. B2V2T4), a *C. kluyveri* TrpB (e.g., UniProt Accession No. A5N7P0), a *C. novyi* TrpB (e.g., UniProt Accession No. A0PYH3), a *C. glutamicum* TrpB (e.g., UniProt Accession No. P06561), a *C. sakazakii* TrpB (e.g., UniProt Accession No. A7MMG1), a *D. aromatica* TrpB (e.g., UniProt Accession No. Q47HQ5), a *D. radiodurans* TrpB (e.g., UniProt Accession No. Q9RVT1), a *D. amylolyticus* TrpB (e.g., UniProt Accession No. B8D4P0), a *D. shibae* TrpB (e.g., UniProt Accession No. A8LSF9), an *E. ictaluri* TrpB (e.g., UniProt Accession No. C5BDB7), an *E. minutum* TrpB (e.g., UniProt Accession No. B2KCI5), an *E. tasmaniensis* TrpB (e.g., UniProt Accession No. B2VKT2), an *E. fergusonii* TrpB (e.g., UniProt Accession No. B7LS19), an *E. sibiricum* TrpB (e.g., UniProt Accession No. B1YLS4), an *F. nodosum* TrpB (e.g., UniProt Accession No. A7HMG8), an *F. philomiragia* TrpB (e.g., UniProt Accession No. B0TWI3), an *F. tularensis* TrpB (e.g., UniProt Accession No. A7N9D2), an *F. nucleatum* TrpB (e.g., UniProt Accession No. Q8RGH8), an *G. stearothermophilus* TrpB (e.g., UniProt Accession No. P19868), an *G. thermodenitrificans* TrpB (e.g., UniProt Accession No. A4IQ82), an *G. violaceus* TrpB (e.g., UniProt Accession No. Q7NGX9), an *H. influenzae* TrpB (e.g., UniProt Accession No. Q4QKF5), an *H. hepaticus* TrpB (e.g., UniProt Accession No. Q7VGA7), an *H. pylori* TrpB (e.g., UniProt Accession No. P56142), an *H. somni* TrpB (e.g., UniProt Accession No. B0UU34), a *K. pneumoniae* TrpB (e.g., UniProt Accession No. B5XT02), a *K. versatilis* TrpB (e.g., UniProt Accession No. Q1ISI9), an *L. casei* TrpB (e.g., UniProt Accession No. P17167), an *L. casei* TrpB (e.g., UniProt Accession No. B3W6W6), an *L. paracasei* TrpB (e.g., UniProt Accession No. Q03CY3), an *L. plantarum* TrpB (e.g., UniProt Accession No. Q88WI0), an *L. lactis* TrpB (e.g., UniProt Accession No. A2RK24), an *L. pneumophila* TrpB (e.g., UniProt Accession No. A5IBF7), an *L. xyli* TrpB (e.g., UniProt Accession No. Q6AF67), an *L. biflexa* TrpB (e.g., UniProt Accession No. B0SDM8), an *L. borgpetersenii* TrpB (e.g., UniProt Accession No. Q04U63), an *L. interrogans* TrpB (e.g., UniProt Accession No. Q72U05), an *L. cholodnii* TrpB (e.g., UniProt Accession No. B1XY48), an *L. innocua* TrpB (e.g., UniProt Accession No. Q92B81), an *L. monocytogenes* TrpB (e.g., UniProt Accession No. B8DHB4), an *L. welshimeri* TrpB (e.g., UniProt Accession No. A0AJ80), an *M. succiniciproducens* TrpB (e.g., UniProt Accession No. Q65TF0), an *M. jannaschii* TrpB (e.g., UniProt Accession No. Q60179), an *M. aeolicus* TrpB (e.g., UniProt Accession No. A6UW25), an *M. voltae* TrpB (e.g., UniProt Accession No. P14638), an *M. labreanum* TrpB (e.g., UniProt Accession No. A2STA4), an *M. kandleri* TrpB (e.g., UniProt Accession No. Q8TX91), an *M. petroleiphilum* TrpB (e.g., UniProt Accession No. A2SHS4), an *M. flagellatus* TrpB (e.g., UniProt Accession No. Q1H0M1), an *M. extorquens* TrpB (e.g., UniProt Accession No. B7L1H4), an *M. nodulans* TrpB (e.g., UniProt Accession No. B8I9V8), an *M. populi* TrpB (e.g., UniProt Accession No. B1ZG57), an *M. radiotolerans* TrpB (e.g., UniProt Accession No. B 1LSI6), an *M. capsulatus* TrpB (e.g., UniProt Accession No. Q604P3), an *M. bovis* TrpB (e.g., UniProt Accession No. P66985), an *M. intracellulare* TrpB (e.g., UniProt Accession No. O68905), an *M. leprae* TrpB (e.g., UniProt Accession No. Q9CC54), an *M. tuberculosis* TrpB (e.g., UniProt Accession No. P9WFX9), an *N. gonorrhoeae* TrpB (e.g., UniProt Accession No. Q84GJ9), an *N. meningitidis* TrpB (e.g., UniProt Accession No. Q9JVC0), an *N. europaea* TrpB (e.g., UniProt Accession No. Q82WI2), an *N. multiformis* TrpB (e.g., UniProt Accession No. Q2Y7R4), an *N. aromaticivorans* TrpB (e.g., UniProt Accession No. Q2G8S7), an *O. iheyensis* TrpB (e.g., UniProt Accession No. Q8ESU4), an *O. anthropi* TrpB (e.g., UniProt Accession No. A6WX28), an *O. carboxidovorans* TrpB (e.g., UniProt Accession No. B6JCP2), a *P. distasonis* TrpB (e.g., UniProt Accession No. A6L9K4), a *P. denitrificans* TrpB (e.g., UniProt Accession No. A1B8L3), a *P. lavamentivorans* TrpB (e.g., UniProt Accession No. A7HPD3), a *P. multocida* TrpB (e.g., UniProt Accession No. P54203), a *P. atrosepticum* TrpB (e.g., UniProt Accession No. Q6D4U0), a *P. carotovorum* TrpB (e.g., UniProt Accession No. C6DGZ5), a *P. zucineum* TrpB (e.g., UniProt Accession No. B4RCL0), a *P. profundum* TrpB (e.g., UniProt Accession No. Q6LPA4), a *P. luminescens* TrpB (e.g., UniProt Accession No. Q7N486), a *P. torridus* TrpB (e.g., UniProt Accession No. Q6L271), a *P. naphthalenivorans* TrpB (e.g., UniProt Accession No. A1VRR7), a *P. marinus* TrpB (e.g., UniProt Accession No. A2BNV9), a *P. atlantica* TrpB (e.g., UniProt Accession No. Q15RZ5), a *P. aeruginosa* TrpB (e.g., UniProt Accession No. P07345), a *P. entomophila* TrpB (e.g., UniProt Accession No. Q1IH20), a *P. fluorescens* TrpB (e.g., UniProt Accession No. Q4KKP4), a *P. putida* TrpB (e.g., UniProt Accession No. P11080), a *P. savastanoi* TrpB (e.g., UniProt Accession No. Q849P2), a *P. syringae* TrpB (e.g., UniProt Accession No. P34817), a *P. lettingae* TrpB (e.g., UniProt Accession No. A8F8F7), a *P. ingrahamii* TrpB (e.g., UniProt Accession No. A1STT0), a *P. aerophilum* TrpB (e.g., UniProt Accession No. Q8ZV44), a *P. arsenaticum* TrpB (e.g., UniProt Accession No. A4WKQ9), a *P. islandicum* TrpB (e.g., UniProt Accession No. A1RVT1), a *P. horikoshii* TrpB (e.g., UniProt Accession No. O59265), an *R. solanacearum* TrpB (e.g., UniProt Accession No. Q8XXY0), an *R. etli* TrpB (e.g., UniProt Accession No. Q2KE82), an *R. leguminosarum* TrpB (e.g., UniProt Accession No. B5ZV70), an *R. loti* TrpB (e.g., UniProt Accession No. Q98CN7), an *R. meliloti* TrpB (e.g., UniProt Accession No. Q92TC9), an *R. sphaeroides* TrpB (e.g., UniProt Accession No. Q9X4E5), an *R. ferrireducens* TrpB (e.g., UniProt Accession No. Q21XI6), an *R. baltica* TrpB (e.g., UniProt Accession No. Q7UKG9), an *R. palustris* TrpB (e.g., UniProt Accession No. Q6NDN6), an *R. denitrificans* TrpB (e.g., UniProt Accession No. Q161H9), an *R. pomeroyi* TrpB (e.g., UniProt Accession No. Q5LV94), an *R. magnifica* TrpB (e.g., UniProt Accession No. A1AXS9), an *S. agona* TrpB (e.g., UniProt Accession No. B5F4M4), an *S. arizonae* TrpB (e.g., UniProt Accession No. A9MPY7), an *S. choleraesuis* TrpB (e.g., UniProt Accession No. Q57NT3), an *S. dublin* TrpB (e.g., UniProt Accession No. B5FU66), an *S. enteritidis* TrpB (e.g., UniProt Accession No. B5R3P4), an *S. heidelberg* TrpB (e.g., UniProt Accession No. B4TJK8), an *S. newport* TrpB (e.g., UniProt Accession No. B4T6X1), an *S. paratyphi* TrpB (e.g., UniProt Accession No. B5BIC1), an *S. schwarzengrund* TrpB (e.g., UniProt Accession No. B4TX38), an *S. typhi* TrpB (e.g., UniProt Accession No. P0A2K2), an *S. typhimurium* TrpB (e.g., UniProt Accession No. P0A2K1), an *S. proteamaculans* TrpB (e.g., UniProt Accession No. A8GF82), an *S. amazonensis* TrpB (e.g., UniProt Accession No. A1S7I2), an *S. baltica* TrpB (e.g., UniProt Accession No. A3D630), an *S. denitrificans* TrpB (e.g., UniProt Accession No. Q12LE2), an *S. frigidimarina* TrpB (e.g., UniProt Accession No. Q084N8), an *S. halifaxensis* TrpB (e.g., UniProt Accession No. B0TP63), an *S. loihica* TrpB (e.g., UniProt Accession No. A3QF73), an *S. oneidensis* TrpB (e.g., UniProt Accession No. Q8ECV0), an *S. pealeana* TrpB (e.g., UniProt Accession No. A8H2X4), an *S. piezotolerans* TrpB (e.g., UniProt Accession No. B8CLM6), an *S. putrefaciens* TrpB (e.g., UniProt Accession No. A4Y845), an *S. woodyi* TrpB (e.g., UniProt Accession No. B1KK02), an *S. boydii* TrpB (e.g., UniProt Accession No. B2U0F2), an *S. dysenteriae* TrpB (e.g., UniProt Accession No. Q32GS9), an *S. flexneri* TrpB (e.g., UniProt Accession No. P0A880), an *S. fredii* TrpB (e.g., UniProt Accession No. C3MB99), an *S. medicae* TrpB (e.g., UniProt Accession No. A6UEI1), an *S. glossinidius* TrpB (e.g., UniProt Accession No. Q2NT52), an *S. aureus* TrpB (e.g., UniProt Accession No. Q2YXX2), an *S. epidermidis* TrpB (e.g., UniProt Accession No. Q8CPB1), an *S. saprophyticus* TrpB (e.g., UniProt Accession No. Q49XH8), an *S. maltophilia* TrpB (e.g., UniProt Accession No. B2FNZ1), an *S. pneumoniae* TrpB (e.g., UniProt Accession No. C1C966), an *S. thermophilus* TrpB (e.g., UniProt Accession No. Q5M350), an *S. avermitilis* TrpB (e.g., UniProt Accession No. Q82A82), an *S. coelicolor* TrpB (e.g., UniProt Accession No. O05625), an *S. griseus* TrpB (e.g., UniProt Accession No. B1W0P0), a *T. pseudethanolicus* TrpB (e.g., UniProt Accession No. B0K8T6), a *T. gammatolerans* TrpB (e.g., UniProt Accession No. C5A1P4), a *T. onnurineus* TrpB (e.g., UniProt Accession No. B6YSU5), a *T. acidophilum* TrpB (e.g., UniProt Accession No. Q9HKD2), a *T. volcanium* TrpB (e.g., UniProt Accession No. Q97A51), a *T. africanus* TrpB (e.g., UniProt Accession No. B7IHA8), a *T. elongatus* TrpB (e.g., UniProt Accession No. Q8DG49), a *T. thermophilus* TrpB (e.g., UniProt Accession No. P16609), a *T. denitrificans* TrpB (e.g., UniProt Accession No. Q3SHL9), a *T. auensis* TrpB (e.g., UniProt Accession No. C4LC89), a *T. erythraeum* TrpB (e.g., UniProt Accession No. Q118P8), a *V. eiseniae* TrpB (e.g., UniProt Accession No. A1WSF1), a *V. okutanii* TrpB (e.g., UniProt Accession No. A5CVH4), a *V.*

*campbellii* TrpB (e.g., UniProt Accession No. A7MRY0), a *V. cholerae* TrpB (e.g., UniProt Accession No. Q9KST6), a *V. fischeri* TrpB (e.g., UniProt Accession No. Q5E623), a *V. metschnikovii* TrpB (e.g., UniProt Accession No. Q9RCE8), a *V. tasmaniensis* TrpB (e.g., UniProt Accession No. B7VGU7), a *V. vulnificus* TrpB (e.g., UniProt Accession No. Q8D8B2), *X. axonopodis* TrpB (e.g., UniProt Accession No. Q8PJ28), *X. campestris* TrpB (e.g., UniProt Accession No. Q4UWD2), *X. oryzae* TrpB (e.g., UniProt Accession No. Q2P0U2), *X. fastidiosa* TrpB (e.g., UniProt Accession No. Q9PDK4), a *Y. enterocolitica* TrpB (e.g., UniProt Accession No. A1JPX6), a *Y. pestis* TrpB (e.g., UniProt Accession No. Q8ZEG9), or a variant thereof.

In some embodiments, the TrpB is recombinantly expressed and optionally isolated and/or purified for carrying out the in vitro tryptophan synthesis. In other embodiments, the TrpB is expressed in whole cells such as bacterial cells, archaeal cells, yeast cells, fungal cells, insect cells, plant cells, or mammalian cells, and these cells are used for carrying out the in vivo tryptophan synthesis. The wild-type or mutated gene can be expressed in a whole cell using an expression vector under the control of an inducible promoter or by means of chromosomal integration under the control of a constitutive promoter. Enzymatic activity can be screened in vivo or in vitro by following product formation by GC or HPLC.

Suitable bacterial host cells include, but are not limited to, BL21 *E. coli*, DE3 strain *E. coli*, *E. coli* M15, DH5α, DH10β, HB101, T7 Express Competent *E. coli* (NEB), *B. subtilis* cells, *Pseudomonas fluorescens* cells, and cyanobacterial cells such as *Chlamydomonas reinhardtii* cells and *Synechococcus elongates* cells. Non-limiting examples of archaeal host cells include *Pyrococcus furiosus, Metallosphera sedula, Thermococcus litoralis, Methanobacterium thermoautotrophicum, Methanococcus jannaschii, Pyrococcus abyssi, Sulfolobus solfataricus, Pyrococcus woesei, Sulfolobus shibatae*, and variants thereof. Fungal host cells include, but are not limited to, yeast cells from the genera *Saccharomyces* (e.g., *S. cerevisiae*), *Pichia* (*P. pastoris*), *Kluyveromyces* (e.g., *K. lactis*), *Hansenula* and *Yarrowia*, and filamentous fungal cells from the genera *Aspergillus, Trichoderma,* and *Myceliophthora*. Suitable insect host cells include, but are not limited to, Sf9 cells from *Spodoptera frugiperda*, Sf21 cells from *Spodoptera frugiperda*, Hi-Five cells, BTI-TN-5B1-4 *Trichophusia ni* cells, and Schneider 2 (S2) cells and Schneider 3 (S3) cells from *Drosophila melanogaster*. Non-limiting examples of mammalian host cells include HEK293 cells, HeLa cells, CHO cells, COS cells, Jurkat cells, NS0 hybridoma cells, baby hamster kidney (BHK) cells, MDCK cells, NIH-3T3 fibroblast cells, and any other immortalized cell line derived from a mammalian cell. Non-limiting examples of plant host cells include those from tobacco, tomato, potato, maize, rice, lettuce, and spinach. In general, cells from plants that have short generation times and/or yield reasonable biomass with standard cultivation techniques are preferable.

In certain embodiments, TrpBs inside living cells are provided. As a non-limiting example, bacterial cells (e.g., *E. coli*) can be used as host whole cell catalysts for in vivo tryptophan preparation, although any number of host whole cells may be used, including but not limited to the host cells described herein. In some embodiments, host whole cell catalysts containing TrpBs are found to significantly enhance the total turnover number (TTN) compared to the in vitro reactions using isolated TrpBs.

The expression vector comprising a nucleic acid sequence that encodes a TrpB can be a viral vector, a plasmid, a phage, a phagemid, a cosmid, a fosmid, a bacteriophage (e.g., a bacteriophage P1-derived vector (PAC)), a baculovirus vector, a yeast plasmid, or an artificial chromosome (e.g., bacterial artificial chromosome (BAC), a yeast artificial chromosome (YAC), a mammalian artificial chromosome (MAC), and human artificial chromosome (HAC)). Expression vectors can include chromosomal, non-chromosomal, and synthetic DNA sequences. Equivalent expression vectors to those described herein are known in the art and will be apparent to the ordinarily skilled artisan.

The expression vector can include a nucleic acid sequence encoding a TrpB that is operably linked to a promoter, wherein the promoter comprises a viral, bacterial, archaeal, fungal, insect, plant, or mammalian promoter. In certain embodiments, the promoter is a constitutive promoter. In some embodiments, the promoter is an inducible promoter. In other embodiments, the promoter is a tissue-specific promoter or an environmentally regulated or a developmentally regulated promoter.

In some embodiments, the nucleic acid sequence encodes a TrpB that comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NOS:2-5. In other embodiments, the nucleic acid sequence encodes a TrpB that comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NOS:2-5. In particular embodiments, the nucleic acid sequence encodes a TrpB that comprises an amino acid sequence that has about 90% or greater (e.g., about 90%, 91%, 92%, 93%, 94%, 95%, 96%, 97%, 98%, 99%, or 100%) identity to the amino acid sequence set forth in SEQ ID NOS:2-5. In some instances, the nucleic acid sequence encodes a TrpB that comprises an amino acid sequence that is about 95%, 96%, 97%, 98%, 99%, or 100% identical to the amino acid sequence set forth in SEQ ID NOS:2-5.

In other embodiments, the nucleic acid sequence encodes a TrpB that comprises an amino acid sequence that contains between about 5 and 124 (e.g., about 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 124) of the amino acids in SEQ ID NOS:2-5. The amino acids may be contiguous, or separated by any number of amino acids.

It is understood that affinity tags may be added to the N- and/or C-terminus of a TrpB expressed using an expression vector to facilitate protein purification. Non-limiting examples of affinity tags include metal binding tags such as His6-tags and other tags such as glutathione S-transferase (GST).

Non-limiting expression vectors for use in bacterial host cells include pCWori, pET vectors such as pET22 (EMD Millipore), pBR322 (ATCC37017), pQE™ vectors (Qiagen), pBluescript™ vectors (Stratagene), pNH vectors, lambda-ZAP vectors (Stratagene); ptrc99a, pKK223-3, pDR540, pRIT2T (Pharmacia), pRSET, pCR-TOPO vectors, pET vectors, pSyn_1 vectors, pChlamy_1 vectors (Life Technologies, Carlsbad, CA), pGEM1 (Promega, Madison, WI), and pMAL (New England Biolabs, Ipswich, MA). Non-limiting examples of expression vectors for use in eukaryotic host cells include pXT1, pSG5 (Stratagene), pSVK3, pBPV, pMSG, pSVLSV40 (Pharmacia), pcDNA3.3, pcDNA4/TO, pcDNA6/TR, pLenti6/TR, pMT vectors (Life Technologies), pKLAC1 vectors, pKLAC2 vectors (New England Biolabs), pQE™ vectors (Qiagen), BacPak baculoviral vectors, pAdeno-X™ adenoviral vectors (Clontech), and pBABE retroviral vectors. Any other vector may be used as long as it is replicable and viable in the host cell.

A number of β-substituted amino acid according to Formula I, as set forth above, can be prepared according to the methods disclosed herein. The compounds can contain unbranched or branched β-substituents ($R^1$) of varying length. $R^1$ can be, for example, optionally substituted ethyl, optionally substituted n-propyl, optionally substituted isopropyl, optionally substituted n-butyl, optionally substituted isobutyl, optionally substituted sec-butyl, optionally substituted tert-butyl, optionally substituted n-pentyl, optionally substituted isopentyl, optionally substituted n-hexyl, optionally substituted branched hexyl, optionally substituted n-heptyl, optionally substituted branched heptyl, optionally substituted n-octyl, and optionally substituted branched octyl. The $R^1$ groups can be substituted with one or more $R^{1a}$ groups as set forth above. In some embodiments, $R^1$ is selected from the group consisting of ethyl, n-propyl, isopropyl, n-butyl, isobutyl, sec-butyl, and tert-butyl. In some embodiments, $R^1$ is selected from the group consisting of ethyl and n-propyl, which are optionally substituted with one or more $R^{1a}$. In some embodiments, $R^1$ is selected from the group consisting of unsubstituted ethyl and unsubstituted n-propyl.

In some embodiments, Y is selected from the group consisting of CH and N. In some embodiments, Y is CH and n is 1, 2, or 3, and $R^2$ is selected from fluoro, chloro, bromo, methyl, ethyl, n-propyl, isopropyl, n-butyl, isobutyl, sec-butyl, and tert-butyl. In some embodiments, subscript n is 1 or 2, and $R^2$ is selected from fluoro, chloro, bromo, methyl, ethyl, n-propyl, isopropyl, n-butyl, isobutyl, sec-butyl, and tert-butyl. In some embodiments, subscript n is 1 and $R^2$ is selected from fluoro, chloro, and methyl.

To produce these compounds with TrpB, the appropriate β-substituted Ser derivatives are needed. Although β-Me-Ser (Thr) is readily available, β-ethyl-, β-propyl- and β-isopropyl-serine are expensive and not available in stereo pure form. With the exception of β-phenylserine, other β-substituted serines are not available. This problem can be addressed using a coupled-enzyme system employing a threonine aldolase (TA), e.g., TA from Thermotoga maritima, to produce β-substituted serines. Natively, TA catalyzes the reversible retro-aldol cleavage of Thr to produce acetaldehyde and glycine. The direction of the reaction can be controlled thermodynamically, favoring the aldol condensation product by using an excess of glycine. TmTA has a promiscuous substrate scope, also catalyzing the aldol condensation of β-Et-Ser, β-Pr-Ser, and β-phenyl-Ser. Combining the two reactions in a one pot in a reaction cascade can provide β-substituted Trp from cheap starting products like glycine and different derivatives of acetaldehyde. As shown in Scheme 1, TmTA can produce both diastereomers. Even though PfTrpB is only active on the syn epimer, this dynamic kinetic asymmetric transformation has a theoretical yield of 100%. PfTrpB uses the syn epimer from the reaction, after which TmTA restores the thermodynamic equilibrium producing the new syn epimer for TrpB to react with.

Scheme 1

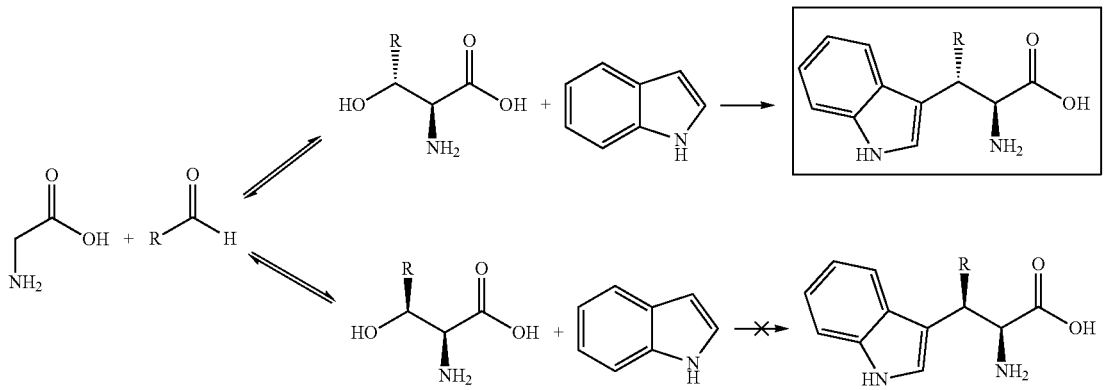

$R^1$ is selected from the group consisting of ethyl, n-propyl, isopropyl, n-butyl, isobutyl, sec-butyl, and tert-butyl, each of which is optionally substituted with $R^{1a}$ In some such embodiments, subscript n is 0, 1, or 2. In some embodiments, Y is N and $R^1$ is selected from the group consisting of ethyl, n-propyl, isopropyl, n-butyl, isobutyl, sec-butyl, and tert-butyl, each of which is optionally substituted with $R^{1a}$. In some such embodiments, subscript n is 0, 1, or 2. In some embodiments, subscript n is 0 or 1.

In some embodiments, $R^2$ is selected from the group consisting of halogen and $C_{1-6}$ alkyl. $R^2$ can be, for example, fluoro, chloro, bromo, methyl, ethyl, n-propyl, isopropyl, n-butyl, isobutyl, sec-butyl, tert-butyl, n-pentyl, isopentyl, n-hexyl, or branched hexyl. In some embodiments, subscript Accordingly, in some embodiments the β-substituted serine is prepared by combining a) glycine, b) an aldehyde, and c) an aldolase or variant thereof under conditions sufficient to form the β-substituted serine. In some embodiments, the aldolase is a threonine aldolase (EC 4.1.2.5). In some embodiments, the aldolase comprises the amino acid sequence set forth in SEQ ID NO:6. In some embodiments, a TmTA variant containing an amino acid sequence having at least about 70% sequence identity to the amino acid sequence set forth in SEQ ID NO:6 is used in the method. The TmTA variant can have, for example, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to the amino acid sequence set forth in SEQ ID NO:6.

IV. Reaction Conditions

The TrpB and other enzymes can be used in purified form, partially purified form, or as whole-cell (e.g., bacterial) catalysts, without purification. Many indoles and β-substituted serines can enter E. coli cells and interact with the enzymes inside the cells, where the reaction takes place. Thus tryptophan compounds can be made in a process wherein intact or partially permeabilized cells expressing the enzyme catalyst are suspended in buffer and combined with indole and β-substituted serine (dissolved in appropriate solvent or in a form of suspension) and allowed to react. The process can also use purified or partially purified protein in place of whole cells. One skilled in the art will be able to identify appropriate processing conditions for a given set of substrates and a given enzyme.

The methods provided herein generally include forming reaction mixtures that comprise an indole, a β-substituted serine, and a TrpB as described above. In some embodiments, the method is carried out in vitro. In other embodiments, the TrpB is localized within a whole cell and the method is carried out in vivo. In some embodiments, the TrpB is expressed in a bacterial, archaeal, yeast or fungal host organism. In some embodiments, the method is carried out under anaerobic conditions. In other embodiments, the process is carried out under aerobic conditions.

The TrpBs can be, for example, purified prior to addition to a reaction mixture or secreted by a cell present in the reaction mixture. The reaction mixture can contain a cell lysate including the TrpB as well as other proteins and other cellular materials. Alternatively, a TrpB can catalyze the reaction within a cell expressing the TrpB. Any suitable amount of TrpB can be used in the methods. In general, the reaction mixtures will contain from about 0.01 mol % to about 10 mol % TrpB with respect to the indole and/or β-substituted serine. The reaction mixtures can contain, for example, from about 0.01 mol % to about 0.1 mol % TrpB, or from about 0.1 mol % to about 1 mol % TrpB, or from about 1 mol % to about 10 mol % TrpB. The reaction mixtures can contain from about 0.05 mol % to about 5 mol % TrpB, or from about 0.05 mol % to about 0.5 mol % TrpB. The reaction mixtures can contain about 0.1, 0.2, 0.3, 0.4, 0.5, 0.6, 0.7, 0.8, 0.9, or about 1 mol % TrpB.

The concentration of the indole and the β-substituted serine are typically in the range of from about 100 µM to about 1 M. The concentration can be, for example, from about 100 µM to about 1 mM, or about from 1 mM to about 100 mM, or from about 100 mM to about 500 mM, or from about 500 mM to 1 M. The concentration can be from about 500 µM to about 500 mM, 500 µM to about 50 mM, or from about 1 mM to about 50 mM, or from about 15 mM to about 45 mM, or from about 15 mM to about 30 mM. The concentration of indole or β-substituted serine can be, for example, about 100, 200, 300, 400, 500, 600, 700, 800, or 900 µM. The concentration of indole or β-substituted serine can be about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500 mM.

Reaction mixtures can contain additional reagents. As non-limiting examples, the reaction mixtures can contain buffers (e.g., M9-N buffer, 2-(N-morpholino)ethanesulfonic acid (IVIES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, $CaCl_2$, and salts of $Mn^{2+}$ and $Mg^{2+}$), denaturants (e.g., urea and guanadinium hydrochloride), detergents (e.g., sodium dodecylsulfate and Triton-X 100), chelators (e.g., ethylene glycol-bis(2-aminoethylether)-N,N,N',N'-tetraacetic acid (EGTA), 2-({2-[Bis(carboxymethyl)amino]ethyl} (carboxymethyl)amino)acetic acid (EDTA), and 1,2-bis(o-aminophenoxy)ethane-N,N,N',N'-tetraacetic acid (BAPTA)), sugars (e.g., glucose, sucrose, and the like), and reducing agents (e.g., sodium dithionite, NADPH, dithiothreitol (DTT), β-mercaptoethanol (BME), and tris(2-carboxyethyl)phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 µM to about 1 M. For example, a buffer, a cosolvent, a salt, a denaturant, a detergent, a chelator, a sugar, or a reducing agent can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. In some embodiments, a reducing agent is used in a sub-stoichiometric amount with respect to the olefin substrate and the diazo reagent. Cosolvents, in particular, can be included in the reaction mixtures in amounts ranging from about 1% v/v to about 75% v/v, or higher. A cosolvent can be included in the reaction mixture, for example, in an amount of about 5, 10, 20, 30, 40, or 50% (v/v).

Reactions are conducted under conditions sufficient to catalyze the formation of the amino acid product. The reactions can be conducted at any suitable temperature. In general, the reactions are conducted at a temperature of from about 4° C. to about 40° C. The reactions can be conducted, for example, at about 25° C. or about 37° C. The TrpBs or cells expressing or containing the TrpBs can be heat treated. In some embodiments, heat treatment occurs at a temperature of about 75° C. The reactions can be conducted at any suitable pH. In general, the reactions are conducted at a pH of from about 6 to about 10. The reactions can be conducted, for example, at a pH of from about 6.5 to about 9 (e.g., about 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0). The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. The reactions can be conducted for about 1 to 4 hours (e.g., 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or 4 hours). Reactions can be conducted under aerobic conditions or anaerobic conditions. Reactions can be conducted under an inert atmosphere, such as a nitrogen atmosphere or argon atmosphere. In some embodiments, a solvent is added to the reaction mixture. In some embodiments, the solvent forms a second phase, and the indole addition to the amino-acrylate intermediate occurs in the aqueous phase. In some embodiments, the TrpB is located in the aqueous layer whereas the substrates and/or products occur in an organic layer. Other reaction conditions may be employed in the methods, depending on the identity of a particular TrpB, indole, or β-substituted serine.

Reactions can be conducted in vivo with intact cells expressing a TrpB or variant as described herein. The in vivo reactions can be conducted with any of the host cells used for expression of the enzymes. A suspension of cells can be formed in a suitable medium supplemented with nutrients (such as mineral micronutrients, glucose and other fuel sources, and the like). Product yields from reactions in vivo can be controlled, in part, by controlling the cell density in the reaction mixtures. Cellular suspensions exhibiting optical densities ranging from about 0.1 to about 50 at 600 nm can be used for the amino acid-forming reactions. Other densities can be useful, depending on the cell type, specific TrpBs, or other factors.

The methods can be assessed in terms of the diastereoselectivity and/or enantioselectivity of indole addition to the amino-acrylate intermediate—that is, the extent to which the reaction produces a particular isomer, whether a diastereomer or enantiomer. A perfectly selective reaction produces a single isomer, such that the isomer constitutes 100% of the product. As another non-limiting example, a reaction producing a particular enantiomer constituting 90% of the total product can be said to be 90% enantioselective. A reaction producing a particular diastereomer constituting 30% of the total product, meanwhile, can be said to be 30% diastereoselective.

In general, the methods include reactions that are from about 1% to about 99% diastereoselective. The reactions are from about 1% to about 99% enantioselective. The reaction can be, for example, from about 10% to about 90% diastereoselective, or from about 20% to about 80% diastereoselective, or from about 40% to about 60% diastereoselective, or from about 1% to about 25% diastereoselective, or from about 25% to about 50% diastereoselective, or from about 50% to about 75% diastereoselective. The reaction can be about 10%, 15%, 20%, 25%, 30%, 35%, 40%, 45%, 50%, 55%, 60%, 65%, 70%, 75%, 80%, 85%, 90%, or about 95% diastereoselective. The reaction can be from about 10% to about 90% enantioselective, from about 20% to about 80% enantioselective, or from about 40% to about 60% enantioselective, or from about 1% to about 25% enantioselective, or from about 25% to about 50% enantioselective, or from about 50% to about 75% enantioselective. The reaction can be about 10%, 15%, 20%, 25%, 30%, 35%, 40%, 45%, 50%, 55%, 60%, 65%, 70%, 75%, 80%, 85%, 90%, or about 95% enantioselective. Accordingly some embodiments provide methods wherein the reaction is at least 30% to at least 90% diastereoselective. In some embodiments, the reaction is at least 30% to at least 90% enantioselective. Preferably, the reaction is at least 80% (e.g., at least about 80%, 81%, 82%, 83%, 84%, 85%, 86%, 87%, 88%, 89%, 90%, 91%, 92%, 93%, 94%, 95%, 96%, 97%, 98%, 99%, or 100%) enantioselective. More preferably, the reaction is at least 90% (e.g., at least about 90%, 91%, 92%, 93%, 94%, 95%, 96%, 97%, 98%, 99%, or 100%) enantioselective.

V. TrpB Variants

Also provided herein are tryptophan synthase β-subunits comprising the amino acid sequence set forth in SEQ ID NO:1 and further comprising an L161A mutation. In some embodiments, the tryptophan synthase β-subunit further includes one or more mutations selected from the group consisting of a V68 mutation, an L91 mutation, an M139 mutation, an N166 mutation, a V173 mutation, an H275 mutation, an A321 mutation, and an S335 mutation. In some embodiments, the tryptophan synthase β-subunit includes the amino acid sequence set forth in any one of SEQ ID NOS:2-5. In some embodiments, the TrpB variants are provided without the N-terminal methionine residues set forth in SEQ ID NOS:2-5.

As described above, the TrpB variant can be a *P. furiosus* TrpB having an amino acid sequence with about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to any of the amino acid sequences described herein (e.g., any of the amino acid sequences set forth in SEQ ID NOS:2-5. The TrpB variant can also contain an amino acid sequence from *T. maritima* TrpB (SEQ ID NO:7), *A. fulgidus* TrpB (SEQ ID NO:8), or *E. coli* Trp (SEQ ID NO:9) and the corresponding mutations made at the analogous amino acid positions.

VI. Non-Canonical Tryptophan Analogs

Also provided herein are β-substituted amino acid according to Formula II:

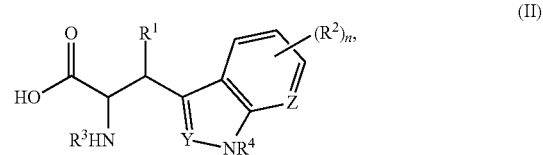

(II)

as well as salts and esters thereof.

For compounds of Formula II:

$R^1$ is $C_{2-8}$ alkyl, which is optionally substituted with one or more $R^{1a}$;

each $R^{1a}$ is independently selected from the group consisting of halogen, —OH, —CN, —N$_3$, —NO$_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N(R$^{1b}$)$_2$, —C(O)R$^{1c}$, —C(O)N(R$^{1b}$)$_2$, —NR$^{1b}$C(O)R$^{1c}$, and —OC(O)R$^{1c}$;

each $R^{1b}$ is independently selected from the group consisting of H and $C_{1-6}$ alkyl;

each $R^{1c}$ is independently selected from the group consisting of H, —OH, halogen, $C_{1-6}$ alkyl, $C_{1-6}$ alkoxy;

Y and Z are independently selected from the group consisting of CH, CR$^2$, and N;

each $R^2$ is independently selected from the group consisting of halogen, —OH, —CN, —N$_3$, —NO$_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N(R$^{2a}$)$_2$, —C(O)R$^{2b}$, —C(O)N(R$^{2a}$)$_2$, —NR$^{2a}$C(O)R$^{2b}$, and —OC(O)R$^{2b}$;

each $R^{2a}$ is independently selected from the group consisting of H and $C_{1-6}$ alkyl;

each $R^{2b}$ is independently selected from the group consisting of H, —OH, halogen, $C_{1-6}$ alkyl, $C_{1-6}$ alkoxy; and subscript n is 0, 1, 2, or 3.

For compounds of Formula II, $R^1$ is not unsubstituted isopropyl, unsubstituted n-butyl, unsubstituted n-pentyl, unsubstituted n-hexyl, (2-acetoxy)ethyl, (1-ethyl)propyl, or 3-methylbut-1-en-3-yl when the conditions: a) Y is CH, b) Z is CH, and c) subscript n is 0 are all met.

For compounds of Formula II, $R^1$ is not unsubstituted ethyl when the conditions: a) Y is CH, b) Z is CH, c) subscript n is 1 or 2, and d) $R^2$ is $C_{1-12}$ alkoxy are all met.

In some embodiments, Y is CH, Z is CH, subscript n is 0, and $R^1$ is not unsubstituted ethyl. In some embodiments, Y is CH, Z is CH, subscript n is 0, and $R^1$ is not unsubstituted n-propyl, (2-methoxy)ethyl, or (1-methyl)ethen-2-yl. In some embodiments, Y is $CCH_3$, Z is CH, subscript n is 0, and $R^1$ is not unsubstituted isopropyl.

In some embodiments, $R^4$ is not benzyl.

In some embodiments, Y and Z are independently selected from the group consisting of CH, $CCH_3$, and N. In some embodiments, Y is CH. In some embodiments, Z is CH In some embodiments, $R^1$ is optionally substituted ethyl, optionally substituted n-propyl, optionally substituted isopropyl, optionally substituted n-butyl, optionally substituted isobutyl, optionally substituted sec-butyl, optionally substituted tert-butyl, optionally substituted n-pentyl, optionally substituted isopentyl, optionally substituted n-hexyl, optionally substituted branched hexyl, optionally substituted n-heptyl, optionally substituted branched heptyl, optionally substituted n-octyl, and optionally substituted branched octyl. The $R^1$ groups can be substituted with one or more $R^{1a}$ groups as set forth above. In some embodiments, $R^1$ is selected from the group consisting of ethyl, n-propyl, isopropyl, n-butyl, isobutyl, sec-butyl, and tert-butyl. In some embodiments, $R^1$ is selected from the group consisting of ethyl and n-propyl, which are optionally substituted with one or more Iea. In some embodiments, $R^1$ is selected from the group consisting of unsubstituted ethyl and unsubstituted n-propyl.

In some embodiments, Y is selected from the group consisting of CH and N. In some embodiments, Y is CH and $R^1$ is selected from the group consisting of ethyl, n-propyl, isopropyl, n-butyl, isobutyl, sec-butyl, and tert-butyl, each of which is optionally substituted with $R^{1a}$. In some such embodiments, subscript n is 0, 1, or 2. In some embodiments, Y is N and $R^1$ is selected from the group consisting of ethyl, n-propyl, isopropyl, n-butyl, isobutyl, sec-butyl, and tert-butyl, each of which is optionally substituted with $R^{1a}$. In some such embodiments, subscript n is 0, 1, or 2. In some embodiments, subscript n is 0 or 1.

In some embodiments, $R^2$ is selected from the group consisting of halogen and $C_{1-6}$ alkyl. $R^2$ can be, for example, fluoro, chloro, bromo, methyl, ethyl, n-propyl, isopropyl, n-butyl, isobutyl, sec-butyl, tert-butyl, n-pentyl, isopentyl, n-hexyl, or branched hexyl. In some embodiments, subscript n is 1, 2, or 3, and $R^2$ is selected from fluoro, chloro, bromo, methyl, ethyl, n-propyl, isopropyl, n-butyl, isobutyl, sec-butyl, and tert-butyl. In some embodiments, subscript n is 1 or 2, and $R^2$ is selected from fluoro, chloro, bromo, methyl, ethyl, n-propyl, isopropyl, n-butyl, isobutyl, sec-butyl, and tert-butyl. In some embodiments, subscript n is 1 and $R^2$ is selected from fluoro, chloro, and methyl.

In some embodiments, $R^3$ and $R^4$ are H; that is, the compounds are unprotected β-substituted tryptophans. In some embodiments, the synthetic methods above further include protecting the β-substituted amino acids to provide protected tryptophan analogs. In some embodiments, $R^3$ and $R^4$ are independently selected amine protecting groups. For example, $R^3$ and $R^4$ can be 9-fluorenylmethoxycarbonyl (Fmoc), tert-butyloxycarbonyl (Boc), cyclohexyloxycarbonyl (Hoc), allyloxycarbonyl (Alloc), mesityl-2-sulfonyl (Mts), 4-(N-methylamino)butanoyl (Nmbu), or 2,4-dimethylpent-3-yloxycarbonyl (Doc). In some embodiments, $R^3$ is Fmoc and $R^4$ is Boc or Alloc. In some embodiments, $R^3$ is Fmoc and $R^4$ is Boc. Such protecting groups can be introduced via known techniques including, for example, those described by Green and Wuts, supra, and Isidro-Llobet, et al. (*Chem. Rev.* 2009, 109, 2455-2504).

The β-substituted tryptophan compounds may optionally contain further substituents. Suitable monovalent substituents on a substitutable carbon atom of an "optionally substituted" group are independently halogen; $-(CH_2)_{0-4}R^+$; $-(CH_2)_{0-4}OR^\alpha$; $-O(CH_2)_{0-4}R^+$, $-O-(CH_2)_{0-4}C(O)OR^\alpha$; $-(CH_2)_{0-4}CH(OR^\alpha)_2$; $-(CH_2)_{0-4}SR^\alpha$; $-(CH_2)_{0-4}Ph$, wherein Ph is phenyl which may be substituted with $R^\alpha$; $-(CH_2)_{0-4})(CH_2)_{0-1}$phenyl, which phenyl may be substituted with $R^\alpha$; —CH=CHPh, wherein Ph is phenyl which may be substituted with $R^\alpha$; $-(CH_2)_{0-4}O(CH_2)_{0-1}$-Py, wherein Py is pyridyl which may be substituted with $R^\alpha$; $-NO_2$; —CN; $-N_3$; $-(CH_2)_{0-4}N(R^\alpha)_2$; $-(CH_2)_{0-4}N(R^\alpha)C(O)R^\alpha$; $-N(R^\alpha)C(S)R^\alpha$; $-(CH_2)_{0-4}N(R^\alpha)C(O)NR^\alpha_2$; $-N(R^\alpha)C(S)NR^\alpha_2$; $-(CH_2)_{0-4}N(R^\alpha)C(O)OR^\alpha$; $-N(R^\alpha)N(R^\alpha)C(O)R^\alpha$; $-N(R^\alpha)N(R^\alpha)C(O)NR^\alpha_2$; $-N(R^\alpha)N(R^\alpha)C(O)OR^\alpha$; $-(CH_2)_{0-4}C(O)R^\alpha$; $-C(S)R^\alpha$; $-(CH_2)_{0-4}C(O)OR^\alpha$; $-(CH_2)_{0-4}C(O)SR^\alpha$; $-(CH_2)_{0-4}C(O)OSiR^\alpha_3$; $-(CH_2)_{0-4}OC(O)R^\alpha$; $-OC(O)(CH_2)_{0-4}SR-SC(S)SR^\alpha$; $-(CH_2)_{0-4}SC(O)R^\alpha$; $-(CH_2)_{0-4}C(O)NR^\alpha_2$; $-C(S)NR^\alpha_2$; $-C(S)SR^\alpha$; $-SC(S)SR^\alpha$, $-(CH_2)_{0-4}OC(O)NR^\alpha_2$; $-C(O)N(OR^\alpha)R^\alpha$; $-C(O)C(O)R^\alpha$; $-C(O)CH_2C(O)R^\alpha$; $-C(NOR^\alpha)R^\alpha$; $-(CH_2)_{0-4}SSR^\alpha$; $-(CH_2)_{0-4}S(O)_2R^\alpha$; $-(CH_2)_{0-4}S(O)_2OR^\alpha$; $-(CH_2)_{0-4}OS(O)_2R^\alpha$; $-S(O)_2NR^\alpha_2$; $-(CH_2)_{0-4}S(O)R^\alpha$; $-N(R^\alpha)S(O)_2NR^\alpha_2$; $-N(R^\alpha)S(O)_2R^\alpha$; $-N(OR^\alpha)R^\alpha$; $-C(NH)NR^\alpha_2$; $-P(O)_2R^\alpha$; $-P(O)R^\alpha_2$; $-OP(O)R^\alpha_2$; $-OP(O)(OR^\alpha)_2$; $SiR^\alpha_3$; $-(C_{1-4}$ straight or branched)alkylene)—O—$N(R^\alpha)_2$; or $-(C_{1-4}$ straight or branched)alkylene)—C(O)O—$N(R^\alpha)_2$. Each $R^\alpha$ is independently hydrogen; $C_{1-6}$ alkyl; $-CH_2Ph$, $-O(CH_2)_{0-1}Ph$; $-CH_2-$(5- to 6-membered heteroaryl); $C_{3-8}$ cycloalkyl; $C_{6-10}$ aryl; 4- to 10-membered heterocyclyl; or 6- to 10-membered heteroaryl; and each $R^\alpha$ may be further substituted as described below.

Suitable monovalent substituents on $R^\alpha$ are independently halogen, $-(CH_2)_{0-2}R^\beta$; $-(CH_2)_{0-2}OH$; $-(CH_2)_{0-2}OR^\beta$; $-(CH_2)_{0-2}CH(OR^\beta)_2$; —CN; $-N_3$; $-(CH_2)_{0-2}C(O)R^\beta$; $-(CH_2)_{0-2}C(O)OH$; $-(CH_2)_{0-2}C(O)OR^\beta$; $-(CH_2)_{0-2}SR^\beta$; $-(CH_2)_{0-2}SH$; $-(CH_2)_{0-2}NH_2$; $-(CH_2)_{0-2}NHR^\beta$; $-(CH_2)_{0-2}NR^\beta_2$; $-NO_2$; $SiR^\beta_3$; $-SiR^\beta_3$; $-C(O)SR^\beta$; $-(C_{1-4}$ straight or branched alkylene)-C(O)OR^\beta$; or $-SSR^\beta$; wherein each $R^1$ is independently selected from $C_{1-4}$ alkyl; $-CH_2Ph$; $-O(CH_2)_{0-1}Ph$; $C_{3-8}$ cycloalkyl; $C_{6-10}$ aryl; 4- to 10-membered heterocyclyl; or 6- to 10-membered heteroaryl. Suitable divalent substituents on a saturated carbon atom of $R^\alpha$ include =O and =S.

Suitable divalent substituents on a saturated carbon atom of an "optionally substituted" group include the following: =O; =S; =NNR$^\gamma_2$; =NNHC(O)R$^\gamma$; =NNHC(O)OR$^\gamma$; =NNHS(O)$_2$R$^\gamma$; =NR$^\gamma$; =NOR$^\gamma$; —O(C(R$^\gamma_2$))$_{2-3}$O—; or —S(C(R$^\gamma_2$))$_{2-3}$S—; wherein each independent occurrence of R$^\gamma$ is selected from hydrogen; $C_{1-6}$ alkyl, which may be substituted as defined below; $C_{3-8}$ cycloalkyl; $C_{6-10}$ aryl; 4- to 10-membered heterocyclyl; or 6- to 10-membered heteroaryl. Suitable divalent substituents that are bound to vicinal substitutable carbons of an "optionally substituted"

group include: —O(C$^β_2$)$_{2-3}$O—; wherein each independent occurrence of R$^β$ is selected from hydrogen; C$_{1-6}$ alkyl which may be substituted as defined below; C$_{3-8}$ cycloalkyl; C$_{6-10}$ aryl; 4- to 10-membered heterocyclyl; or 6- to 10-membered heteroaryl.

Suitable substituents on the alkyl group of RY include halogen; —R$^δ$; —OH; —OR$^δ$; —CN; —C(O)OH; —C(O)OR$^δ$; —NH$_2$; —NHR$^δ$; —NR$^δ_2$; or —NO$_2$; wherein each R$^δ$ is independently C$_{1-4}$ alkyl; —CH$_2$Ph; —O(CH$_2$)$_{0-1}$Ph; 4- to 10-membered heterocyclyl; or 6- to 10-membered heteroaryl.

Suitable substituents on a substitutable nitrogen of an "optionally substituted" group include —R$^ε$; —NR$^ε_2$; —C(O)R$^ε$; —C(O)OR$^ε$; —C(O)C(O)R$^ε$; —C(O)CH$_2$C(O)R$^ε$; —S(O)$_2$R$^ε$; —S(O)$_2$NR$^ε_2$; —C(S)NR$^ε_2$; —C(NH)NR$^ε_2$; or —N(R$^ε$)S(O)$_2$R$^ε$; wherein each R$^ε$ is independently hydrogen; C$_{1-6}$ alkyl which may be substituted as defined below; C$_{3-8}$ cycloalkyl; C$_{6-10}$ aryl; 4- to 10-membered heterocyclyl; or 6- to 10-membered heteroaryl.

Suitable substituents on the alkyl group of R$^ε$ are independently halogen; —R$^δ$; —OH; —OR$^δ$; —CN; —C(O)OH; —C(O)OR$^δ$; —NH$_2$; —NHR$^δ$; —NR$^δ_2$; or —NO$_2$; wherein each R$^δ$ is independently C$_{1-4}$ alkyl; —CH$_2$Ph; —O(CH$_2$)$_{0-1}$Ph; C$_{6-10}$ aryl; 4- to 10-membered heterocyclyl; or 6- to 10-membered heteroaryl.

In some embodiments, the β-substituted amino acid is selected from the group consisting of:

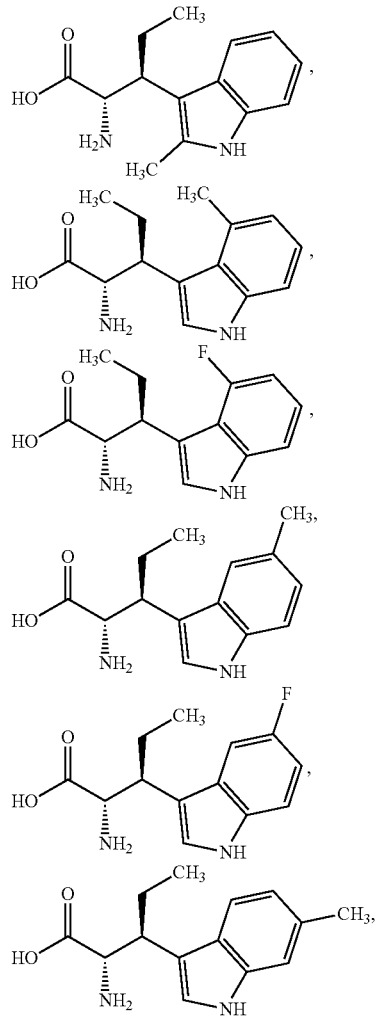

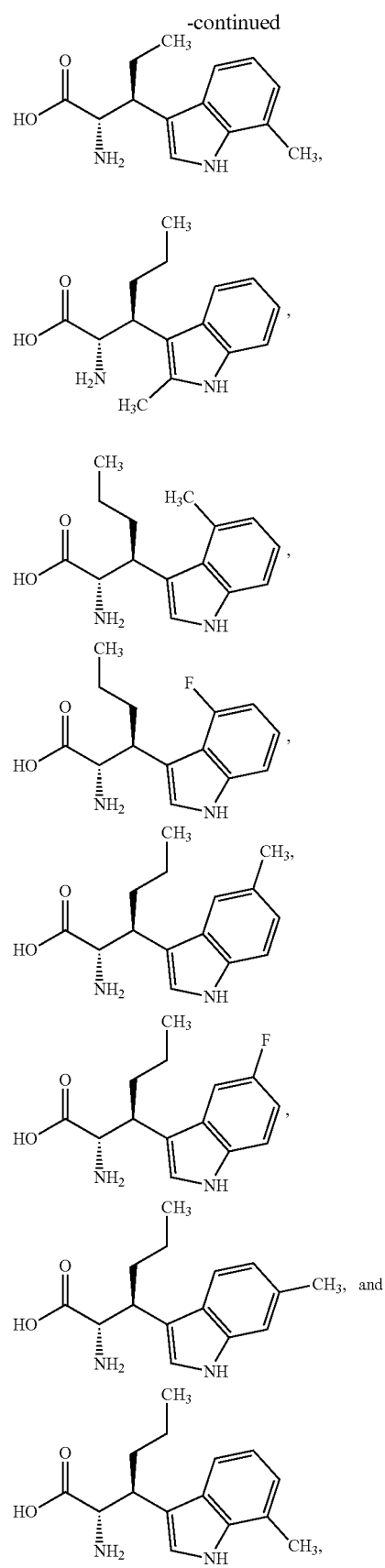

and salts and esters thereof.

VII. Examples

Example 1. Identification of Effective Trp-Forming Catalysts Via Enzyme Screening Mechanistic analysis has shown that PfTrpB's yield and substrate scope are limited by competing hydrolysis of the reactive amino-acrylate intermediate (E(A-A)) (FIG. 2A), resulting in abortive deamination that consumes the amino acid substrate (FIG. 2A). Deamination can be overcome with additional equivalents of Thr, but the reaction scope and yields (typically <50%) are still limited when compared to the native Ser substrate. Further, PfTrpB$^{2B9}$ is effective only for the synthesis of β-methyltryptophan analogs, while synthesis of other β-branched ncAAs remained elusive. To surmount these challenges, it was envisioned that increasing the persistence of the reactive intermediate would decrease deamination while simultaneously facilitating reactions with more challenging β-alkylated substrates. It was further speculated that active-site mutations would enhance activity with larger β-substituents that are sterically disfavored. The ideal synthase would be able to utilize diverse indole and amino acid analogs to produce an array of β-branched ncAAs, making these desirable molecules readily available for the first time.

Reported herein is such an engineered catalyst, PfTrpB$^{7E6}$, that integrates nine mutations from mechanism-guided engineering, random mutagenesis, and recombination. The utility of PfTrpB$^{7E6}$ as an ncAA synthase is demonstrated by producing 27 β-branched tryptophan analogs, 20 of which have not been previously reported. Mechanistic analysis indicates that the broad substrate scope of this catalyst is attributed to the increased steady-state population of E(A-A). The rate of the competing deamination reaction was also reduced, improving yield while necessitating only a single equivalent of substrate.

Directed evolution toward a β-branched ncAA synthase was initiated by searching for enzymes capable of producing the β-branched ncAA, (2S, 3S)-β-ethyltryptophan (β-EtTrp). A panel of PfTrpB variants was assayed as described below.

Small-scale analytical reactions. All analytical reactions were performed in 2-mL glass HPLC vials charged with nucleophile substrate, followed by addition of amino acid substrate and purified enzyme in 50 mM KPi buffer, pH 8.0 to a final volume of 150 µL. Reactions were incubated in a 75° C. water bath for 24 hours. The reaction was then diluted with 850 µL of 1:1 1-M aq. HCl/CH$_3$CN and vortexed thoroughly. The reaction mixture was then subjected to centrifugation at >20,000 g for 10 minutes and the supernatant analyzed by HPLC. Yields were determined at the relevant isosbestic point (Table 1) and calculated as area of the product peak divided by the sum of the integrated product and substrate peaks. All reactions were performed at least in duplicate.

TABLE 1

Isosbestic point of Trp analogs and the corresponding indole analog.

| Nucleophile substrate | Isosbestic point (nm) |
| --- | --- |
| Indole | 277 |
| 2-methylindole | 279 |
| 4-methylindole | 279 |
| 4-fluoroindole | 267 |
| 5-methylindole | 280 |
| 5-fluoroindole | 282 |
| 5-chloroindole | 260 |
| 6-methylindole | 273 |
| 7-methylindole | 272 |
| Indazole | 276 |
| 7-azaindole | 292 |

TTN determination. A 2-mL glass HPLC vial was charged with 20 mM nucleophile substrate as 6 µL of a 500-mM solution in DMSO. Next, 20 mM amino acid substrate and 2 µM purified enzyme (0.01% catalyst loading, 10,000 max TTN) were added as a solution in 50 mM KPi buffer, pH 8.0. The reactions were worked up and analyzed as described above. TTN were determined as yield times max TTN.

Coupling efficiency. A 2-mL glass HPLC vial was charged with 20 mM nucleophile substrate as 6 µL of a 500-mM solution in DMSO. Next, 20 mM amino acid substrate and 20 µM purified enzyme (0.1% catalyst loading, 1,000 max TTN) were added as a solution in 50 mM KPi buffer, pH 8.0. Coupling efficiency was described as the yield under reaction conditions with high catalyst loading and equimolar substrate equivalents.

UV-Vis Spectroscopy. Spectra were collected on a Shimadzu UV1800 spectrophotometer in a quartz cuvette with a 1 cm path length at 75° C.

Figure 3A:
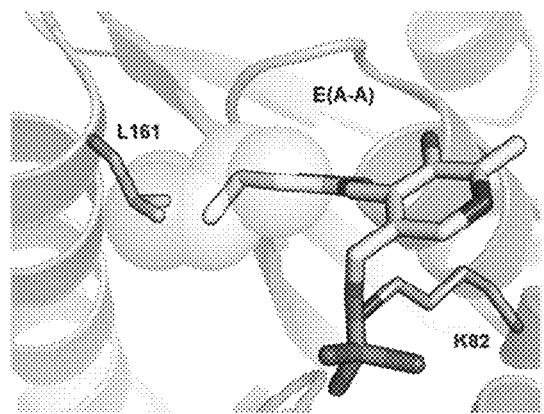
FIG. 3A shows β-EtSer as the amino-acrylate modeled in the PfTrpB$^{2B9}$ (PDB: 5VM5) active site. Spheres represent the Van der Waals radii.
Figure 3B:
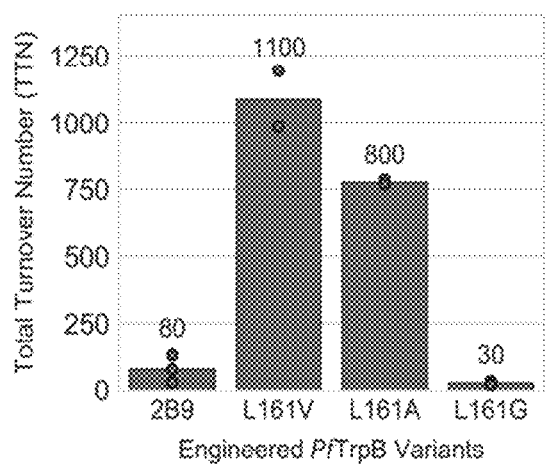
FIG. 3B shows β-EtTrp production by PfTrpB$^{2B9}$ with L161V, L161A, or L161G mutations.

It was determined that the previously evolved β-MeTrp synthase PfTrpB$^{2B9}$ was the most promising starting point for β-EtTrp production. However, PfTrpB$^{2B9}$ showed low product formation (80 total turnovers, TTN), which is insufficient for detection in high-throughput screening. A structure-guided approach was used to improve the enzyme's activity, using the previously determined structure of PfTrpB$^{2B9}$ (PDB: 5VM5). (2S, 3R)-β-Ethylserine (β-EtSer) was modeled into the PfTrpB$^{2B9}$ active site and found that formation of E(A-A) is likely impeded by a steric clash with L161 (FIG. 3A). Hypothesizing that steric constraints could be reduced by mutation to residues with smaller side chains, variants PfTrpB$^{2B9}$L161V, L161A, and L161G were expressed and analyzed. L161V and L161A increased the TTN 14-fold and 10-fold, respectively, whereas L161G decreased activity by a factor of 2.6 (FIG. 3B). Because an objective was to produce a catalyst that accommodates a range of β-branched alkyl chains, PfTrpB$^{2B9}$ L161A was selected as the parent enzyme for directed evolution, with the rationale that the smaller sidechain would minimize steric clashes with bulkier substrates.

Example 2. TrpB Engineering Provides Enhanced Catalyst Activity

Cloning. PfTrpB$^{WT}$ (UNIPROT ID Q8U093) was previously codon optimized for expression in *Escherichia coli*, and cloned into pET-22b(+) with a C-terminal 6× His tag. Parent variant PfTrpB$^{2B9}$ (E17G, I68V, T292S, F274S, T321A, F95L, 116V, V384A) was cloned and expressed as described previously (see, Herger, et al. *J. Am. Chem. Soc.* 138, 8388-8391 (2016)).

Construction of random mutagenesis libraries. Random mutagenesis libraries were generated with the appropriate PfTrpB gene as template by the addition of 200-400 µM MnCl$_2$ to a Taq PCR reaction as reported previously (see, Buller, et al. *Proc. Natl. Acad. Sci. U.S.A.* 112, 14599-14604 (2015)). PCR fragments were treated with DpnI for two hours at 37° C., purified by gel extraction, and then inserted into a pET-22b(+) vector via Gibson assembly (see, Gibson, et al. *Nat. Methods* 6, 343-345 (2009)). BL21(DE3) E. Cloni® Express cells were transformed with the Gibson assembly product.

TABLE 2

Primers for random mutagenesis

| Primer | Sequence (5' to 3') |
|---|---|
| Random mutagenesis forward (NdeI) | GAAATAATTTTGTTTAACTTTAAGAAGGAGATATACATATG (SEQ ID NO: 10) |
| Random mutagenesis reverse (XhoI) | GCCGGATCTCAGTGGTGGTGGTGGTGCTCGAG (SEQ ID NO: 11) |
| pET22-b(+) Forward | CATATGTATATCTCCTTCTTAAAGTTAAACAAAATTATTTC (SEQ ID NO: 12) |
| pET22-b(+) Reverse | CTCGAGCACCACCACCACCACCACTGAGATCCGGC (SEQ ID NO: 13) |

Construction of recombination libraries. Recombination libraries used primers with degenerate codons to cause an equal ratio of mutant and wild-type residues at a given site (I16V, E17G, I68V, V173E, F274S/L, T321A, and V384A). The library was prepared in two rounds of PCR. For the first round, a PCR with Phusion® polymerase produced four fragments of the PfTrpB$^{8C8}$ gene (NdeI to I16/E17, I16/E17 to V173, V173 to T321, T321 to XhoI). Fragments were treated with DpnI for one hour at 37° C. and purified by a preparative agarose gel. The individual fragments were used as template in an assembly PCR with pET22-specific flanking primers to generate the full-length insert. This assembled product was then used as template for the second round of PCR amplification, producing another four fragments of the PfTrpB$^{8C8}$ gene (NdeI to I68, I68 to F274, F274 to V384, V384 to XhoI). The fragments were treated as described above. The complete library was then inserted into pET-22b (+) via Gibson assembly. BL21(DE3) E. Cloni® Express cells were transformed with the library.

TABLE 3

Summary of the residues that were subjected to recombination.

| Variant | Screened Substrate | Mutations |
|---|---|---|
| PfTrpB$^{4D11}$ | Serine | E17G, I68V, F274S, T321A |
| PfTrpB$^{2B9}$ | Threonine | I16V, V384A |
| PfTrpB$^{8C8}$ | β-EtSer | V173E |

TABLE 4

Primers for cloning recombination libraries.

| Fragment | Forward primer (5' to 3') | Reverse primer (5' to 3') |
|---|---|---|
| NdeI to I16/E17 | GAAATAATTTTGTTTAACTTTAAGAAGGAGATATACATATG (SEQ ID NO: 14) | TTCAGGGGTYCTAYCAGCGTTTCTGG (SEQ ID NO: 22) |
| I16/E17 to V173 | CCAGAAACGCTGRTAGRACCCCTGAA (SEQ ID NO: 15) | TATTCAAAAGTAGCTWCCCAATCACGCAGAGCC (SEQ ID NO: 23) |
| V173 to T321 | GGCTCTGCGTGATTGGGWAGCTACTTTTGAATA (SEQ ID NO: 16) | TTCTTCATCGGTTACTGYCACGTATTCAGCAC (SEQ ID NO: 24) |
| T321 to XhoI | GTGCTGAATACGTGRCAGTAACCGATGAAGAA (SEQ ID NO: 17) | GCCGGATCTCAGTGGTGGTGGTGGTGCTCGAG (SEQ ID NO: 25) |
| NdeI to I68 | GAAATAATTTTGTTTAACTTTAAGAAGGAGATATACATATG (SEQ ID NO: 18) | CACGTTTCAGGTATAYTTTAGCACCACCG (SEQ ID NO: 26) |
| I68 to F274 | CGGTGGTGCTAAARTATACCTGAAACGTG (SEQ ID NO: 19) | GACAGCATGCCATGMRACACACCAACCTGACC (SEQ ID NO: 27) |
| F274 to V384 | GGTCAGGTTGGTGTGTYKCATGGCATGCTGTC (SEQ ID NO: 20) | GAGCACGTTGCCAGATRCTTTCAGGACAATATC (SEQ ID NO: 28) |
| V384 to XhoI | GATATTGTCCTGAAAGYATCTGGCAACGTGCTC (SEQ ID NO: 21) | GCCGGATCTCAGTGGTGGTGGTGGTGCTCGAG (SEQ ID NO: 29) |

Site-directed and site-saturation mutagenesis. Site-directed mutagenesis was performed with QuikChange® or Q5® kits per manufacturer's recommendations. Q5® primers were designed using the NEBASECHANGER® software. PCR with Phusion® polymerase was used to site-saturate L161 in PfTrpB$^{2B9}$. Primers were mixed as described previously (see, Kille, et al. ACS Synth. Biol. 2, 83-92 (2013)). Constructs were used to transform BL21 (DE3) E. Cloni® Express cells.

TABLE 5

Primers for site-directed and site-saturation mutagenesis.

| Target site | Forward primer (5' to 3') | Reverse primer (5' to 3') |
|---|---|---|
| PfTrpB$^{2B9}$ $^{L161G}$ | CCGGTTCTCGCACCGGGAAAG ACGCAATCAACG (SEQ ID NO: 30) | GGCCAAGAGCGTGCCCTTTCTG CGTTAGTTGC (SEQ ID NO: 33) |
| PfTrpB$^{2B9}$ $^{L161}$ site-saturation | CGTAATTCCAGTTAACTCCGG TTCTCGCACCXXXAAAGACGC AATCAACG (SEQ ID NO: 31, 36, 37) | GGTGCGAGAACCGGAGTTAACT GGAATTACGTTTGC (SEQ ID NO: 34) |
| PfTrpB$^{7E6}$ $^{A161V}$ | TTCTCGCACCGTGAAAGACGC AA (SEQ ID NO: 32) | CCGGAGTTAACTGGAATTACGT TTG (SEQ ID NO: 35) |

XXX in site saturation primers denotes NDT, VHG, or TGG.

Protein expression and purification. A single colony containing the appropriate PfTrpB gene was used to inoculate 5 mL Terrific Broth supplemented with 100 μg/mL ampicillin (TB$_{amp}$) and incubated overnight at 37° C. and 230 rpm. For expression, 2.5 mL of overnight culture were used to inoculate 250 mL TB$_{amp}$ in a 1-L flask and incubated at 37° C. and 250 rpm for three hours to reach OD$_{600}$ 0.6 to 0.8. Cultures were chilled on ice for 20 minutes and expression was induced with a final concentration of 1 mM isopropyl β-D-thiogalactopyranoside (IPTG). Expression proceeded at 25° C. and 250 rpm for approximately 20 hours. Cells were harvested by centrifugation at 5,000 g for five minutes at 4° C., and then the supernatant was decanted. The pellet was stored at −20° C. until further use.

Thawed cell pellets were resuspended in 9 mL of lysis buffer containing 25 mM potassium phosphate buffer, pH 8.0 (KPi buffer) with 100 mM NaCl, 20 mM imidazole, 1 mg/mL hen egg white lysozyme (HEWL), 200 μM pyridoxal phosphate (PLP), 2 mM MgCl$_2$, 0.02 mg/mL DNase I. Pellets were completely resuspended and then lysed with 1 mL BugBuster® according to manufacturer's recommendations. Lysate was heat treated at 75° C. for 15 minutes. The supernatant was collected from clarified lysate following centrifugation for 15 minutes at 15,000 g and 4° C. Purification was performed with an AKTA purifier FPLC system (GE Healthcare) and a 1-mL Ni-NTA column. Protein was eluted by applying a linear gradient of 100 mM to 500 mM imidazole in 25 mM KPi buffer, pH 8.0 and 100 mM NaCl. Fractions containing purified protein were dialyzed into 50 mM KPi buffer, pH 8.0, flash frozen in liquid nitrogen, and stored at −80° C. Protein concentrations were determined using the Bio-Rad Quick Start™ Bradford Protein Assay.

Library expression and screening. Single colonies from libraries containing the appropriate PfTrpB variant genes were expressed in 96-well deep-well plates containing 300 of TB$_{amp}$ and incubated overnight (approximately 20 hours) at 25° C. and 250 rpm with 80% humidity. For expression, 20 μL of overnight culture were transferred into 630 μL TB$_{amp}$ and incubated for three hours at 37° C. and 250 rpm with 80% humidity. Cells were then chilled on ice for 20 minutes and induced with 50 μL of IPTG in TB$_{amp}$ (0.5 mM-1 mM final concentration), followed by overnight incubation at 37° C. and 250 rpm. Cells were harvested by centrifugation at 4° C. and 4,000 g for 15 minutes and then stored at −20° C. for at least 24 hours. Cell plates were thawed and resuspended in 400 μL/well 50 mM KPi buffer, pH 8.0 with 1 mg/mL HEWL, 100 μM PLP, 2 mM MgCl$_2$, and 0.02 mg/mL DNase. Cells were lysed by a 30-60-min incubation at 37° C. and heat treatment in a 75° C. water bath for 20 min. Lysate was clarified by centrifugation at 5,000 g for 10 minutes.

Reactions were performed in a UV-transparent 96-well assay plate with a total volume of 200 μL/well comprised of 20-40 μL heat-treated lysate, 500 μM indole, and 5 mM β-DL-ethylserine in 50 mM KPi buffer, pH 8.0. Due to the racemic nature of the substrate, the effective concentration of β-L-ethylserine is 2.5 mM. Reactions proceeded in a 75° C. water bath and were assessed for product formation at multiple time points (0.5-4 hours). Prior to being measured, plates were cooled on ice and centrifuged briefly to collect condensation and assayed by measuring absorption at 290 nm.

Determination of T$_{50}$ values. A solution of 1 μM purified enzyme in 50 mM KPi buffer, pH 8.0 was aliquoted into 12 PCR tubes with a volume of 95 μL/tube. Ten of these samples were incubated in a thermocycler for 60 minutes with a temperature gradient from 75° C. to 95° C., while the two remaining samples were incubated at room temperature as controls. All 12 tubes were centrifuged for three minutes to pellet precipitated enzyme, and then 75 μL of the supernatant were transferred from each tube to a UV-transparent 96-well assay plate. Enzyme activity was determined by adding an additional 75 μL of 50 mM KPi buffer, pH 8.0 containing 1 mM indole and 1 mM serine to each well. Reactions were incubated for 10 minutes at 75° C. and then briefly centrifuged to collect condensation. Activity was determined by measuring product formation at 290 nm. Activity was correlated to incubation temperature, and thermostability is reported as the temperature at which half of the activity is lost (T$_{50}$) after 1-hour incubation. Measurements were conducted in duplicate.

Figure 3C:
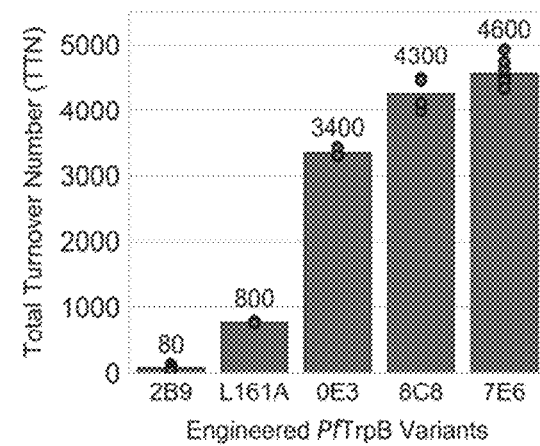
FIG. 3C shows β-EtTrp synthesis by engineered PfTrpB variants.

Results. Variants were assayed for increased production of β-EtTrp at 290 nm under saturating substrate conditions. Screening made use of starting materials containing a mixture of diastereomers, however only the (2S,3R) diastereomer undergoes a productive reaction with PfTrpB. Iterative mutagenesis and screening identified variants PfTrpB$^{0E3}$ (L91P) and PfTrpB$^{8C8}$ (V173E) that increased TTN an additional 4-fold and 1.3-fold, respectively (FIG. 3C). At this juncture, a third round of random mutagenesis failed to yield further improvements. Although the accumulated mutations increased activity, it was speculated that further improvements were hindered by deleterious mutations that reduced enzyme stability. Seven mutations, believed to be possibly destabilizing or superfluous (I16V, E17G, I68V, V173E, F274S, T321A, and V384A), were selected and recombination was conducted, allowing a 50% chance for a residue to retain the mutation or revert to wild type. Recombination also included F274L, which was previously identified as an activating mutation. Recombination revealed that I68V and T321A were non-essential, but that F274L was beneficial, yielding variant PfTrpB7E6 (Table 6).

TABLE 6

Engineering PfTrpB through directed evolution.

| Variant | Engineering Approach | Mutations Added | Mutations Removed | Fold Improvement |
|---|---|---|---|---|
| PfTrpB$^{2B9\ L161A}$ | Rational design | L161A | N/A | 10 |
| PfTrpB$^{0E3}$ | Random mutagenesis | L91P | N/A | 43 |
| PfTrpB$^{8C8}$ | Random mutagenesis | V173E | N/A | 54 |
| PfTrpB$^{7E6}$ | Recombination | F274L | I68V, T321A | 58 |

Fold improvements are β-EtTrp production relative to PfTrpB$^{2B9}$ (PfTrpB I16V, E17G, I68V, F95L, F274S, T292S, T321A, and V384A).

Though PfTrpB$^{7E6}$ did not show improved stability (Table 7), recombination did enhance activity; up to a 58-fold improvement relative to PfTrpB$^{2B9}$ (FIG. 3C). Due to its efficient synthesis of β-EtTrp, PfTrpB$^{7E6}$ was selected for subsequent characterization. In Table 7, Thermostability is reported as the temperature at which half the activity is lost ($T_{50}$) after 1-hour incubation.

TABLE 7

Thermostability of evolved PfTrpB variants

| PfTrpB Variant | $T_{50}$ (° C.) |
|---|---|
| PfTrpB$^{2B9}$ | 95.0 ± 0.2 |
| PfTrpB$^{2B9\ L161A}$ | 81.3 ± 0.7 |
| PfTrpB$^{0E3}$ | 86.0 ± 0.1 |
| PfTrpB$^{8C8}$ | 89.3 ± 0.8 |
| PfTrpB$^{7E6}$ | 86.6 ± 0.1 |

Example 3. Mechanistic Study of TrpB Catalysts

Newly evolved properties of PfTrpB that enabled activity with challenging β-branched substrates were then identified.

Steady-state distribution of catalytic intermediates. Spectra were collected between 250 nm and 500 nm immediately following substrate addition. Samples were prepared in a total volume of 400 μL with 20 μM purified enzyme and 20 mM substrate (threonine, β-L-ethylserine, β-L-propylserine) in 50-200 mM KPi buffer, pH 8.0. Data were baseline subtracted and normalized to the E(Ain) peak at 412 nm. Catalytic intermediates were assigned at the following wavelengths: E(Ain) at 412 nm, E(Aex$_1$) at 428 nm, and E(A-A) at 350 nm.

Deamination of the amino-acrylate. Spectra were collected between 250-550 nm immediately following substrate addition, and then once per minute for ten minutes. Samples were prepared in a total volume of 400 μL with 20 μM purified enzyme and 20 mM substrate (Threonine, β-L-ethylserine, β-L-propylserine) in 50-200 mM KPi buffer, pH 8.0. Data were baseline subtracted and plotted as absorbance over time where α-keto acid formation is represented by the slope. Deamination is described in AU/min as the extinction coefficient is unknown for β-L-ethylserine and β-L-propylserine.

Isosbestic points. Spectra were collected between 250 nm and 550 nm immediately following substrate addition, and then once per minute for ten minutes. Samples were prepared in a total volume of 400 μL with 1 μM of purified enzyme and 100 μM-1 mM nucleophile substrate in 50 mM KPi buffer, pH 8.0. The isosbestic point was defined as the overlapped position of the starting material and product UV peaks. The isosbestic point of some nucleophiles have been reported previously.

Figure 4A:
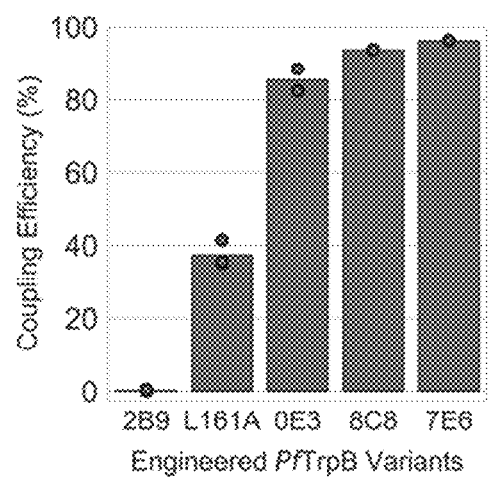
FIG. 4A shows that directed evolution stabilizes the amino-acrylate intermediate and improves coupling efficiency. Variant coupling efficiency with β-EtSer improves from 5% to 96% throughout directed evolution.

Results. As described above, the activity and substrate scope of the parent enzyme, PfTrpB$^{2B9}$, were limited by hydrolysis of the reactive E(A-A) intermediate. The coupling efficiency of each enzyme in the PfTrpB$^{7E6}$ lineage was assessed under reaction conditions with high catalyst loading and equimolar substrate equivalents, where product formation is limited only by the consumption of starting material through the competing deamination reaction. Under these conditions, an increase in product formation from 5% with PfTrpB$^{2B9}$ to 96% with PfTrpB$^{7E6}$ (FIG. 4A) was measured. Consistent with the improved coupling efficiency, a decrease in the competing deamination reaction during directed evolution was observed (Table 8). For Table 8, the change in absorption at 320 nm was monitored for 10 minutes. Deamination rate are reported in units of AU/min; N.R.=reaction, E(A-A) was not observed under these reaction conditions.

TABLE 8

Enzymatic formation of α-keto acids.

| | Substrate deamination (mAU/min) | | |
|---|---|---|---|
| Enzyme | Thr | β-EtSer | β-PrSer |
| PfTrpB$^{2B9}$ | 2.4 | N.R. | N.R. |
| PfTrpB$^{8C8}$ | 3.6 | 6.2 | 3.9 |
| PfTrpB$^{7E6}$ | 2.4 | 4.4 | 3.0 |

Figure 4B:
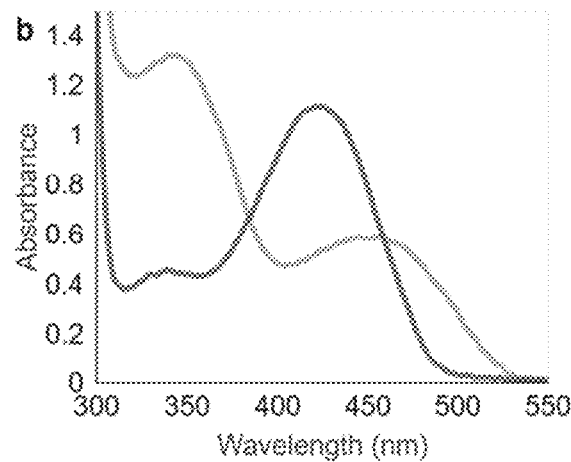
FIG. 4B shows that Directed evolution shifts the steady-state population of PfTrpB with β-EtSer. Substrate-bound PfTrpB$^{2B9}$ has E(Ain) the predominant population with $\lambda_{max}$=412 nm. E(A-A) ($\lambda_{max}$=350 nm) is the major species with substrate-bound PfTrpB$^{7E6}$.

To assess the abundance of E(A-A), the intrinsic spectroscopic properties of the PLP cofactor were leveraged to visualize the steady-state distribution of intermediates throughout the catalytic cycle (FIG. 2A). With the addition of β-EtSer to PfTrpB$^{7E6}$, the internal aldimine peak (E(Ain), 412 nm) decreases and E(A-A) (350 nm) is the major species (FIG. 4B). This is a notable change, as PfTrpB$^{2B9}$ was only poorly active with β-EtSer and E(Ain) remained the predominant species. Collectively, these data indicate that increased product formation was achieved by incorporating mutations that increase the lifetime of E(A-A). In turn, PfTrpB$^{7E6}$ shows reduced E(A-A) deamination, ultimately permitting productive β-substitution with challenging substrates.

Example 4. Structural Characterization of TrpB Catalysts

Figure 2:
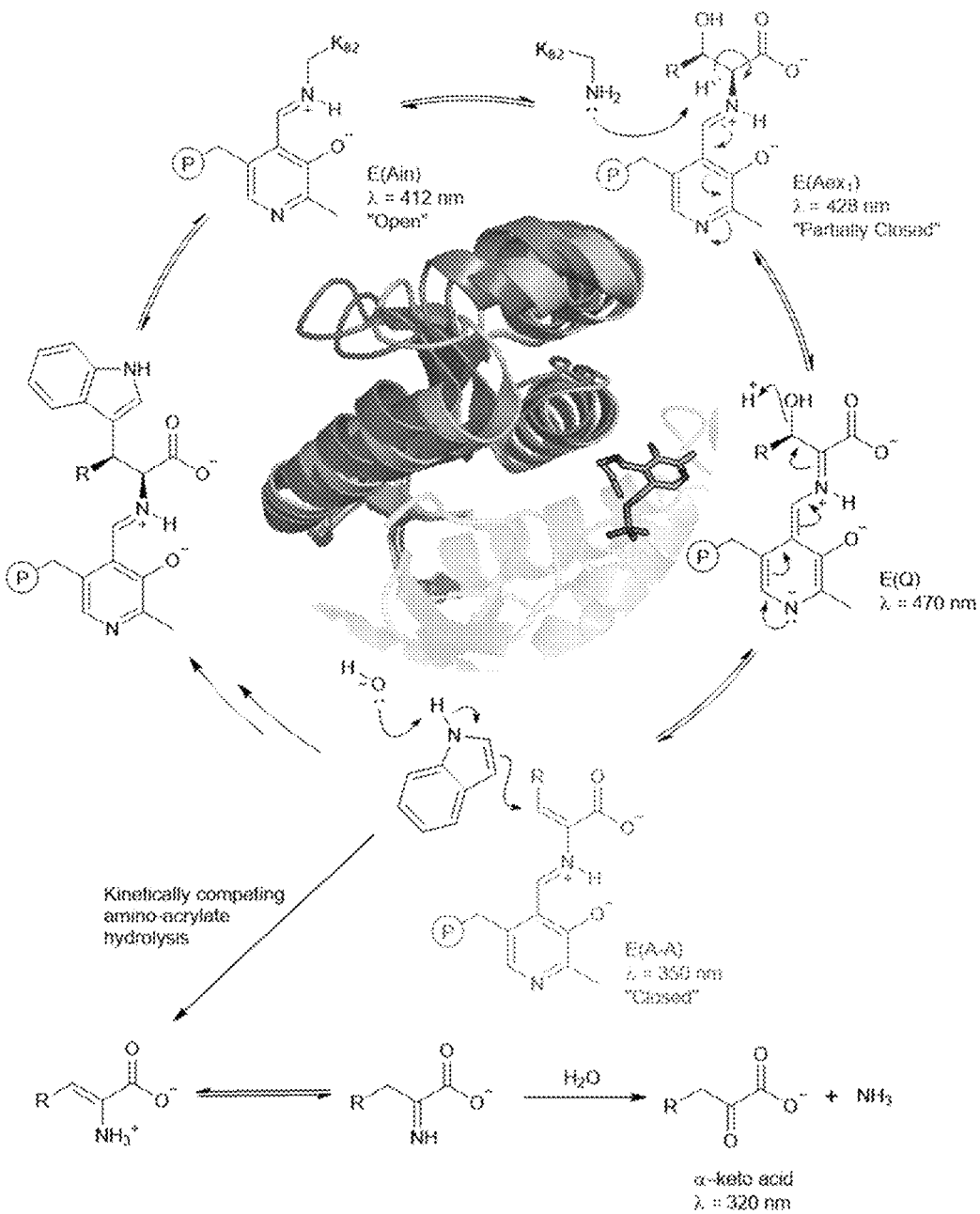
FIG. 2 shows the putative catalytic cycle for PfTrpB. Top: Catalysis initiates as E(Ain) with the mobile COMM domain predominantly in the open conformation. With the addition of substrate, the COMM domain undergoes rigid body motion, transitioning to a partially closed position through E(Aex$_1$) followed by full closure with formation of the reactive E(A-A) intermediate. Bottom: Kinetically competing amino-acrylate deamination may generate α-keto acids, observable at 320 nm. This side reaction consumes an equivalent of the amino acid substrate.
Figure 7A:
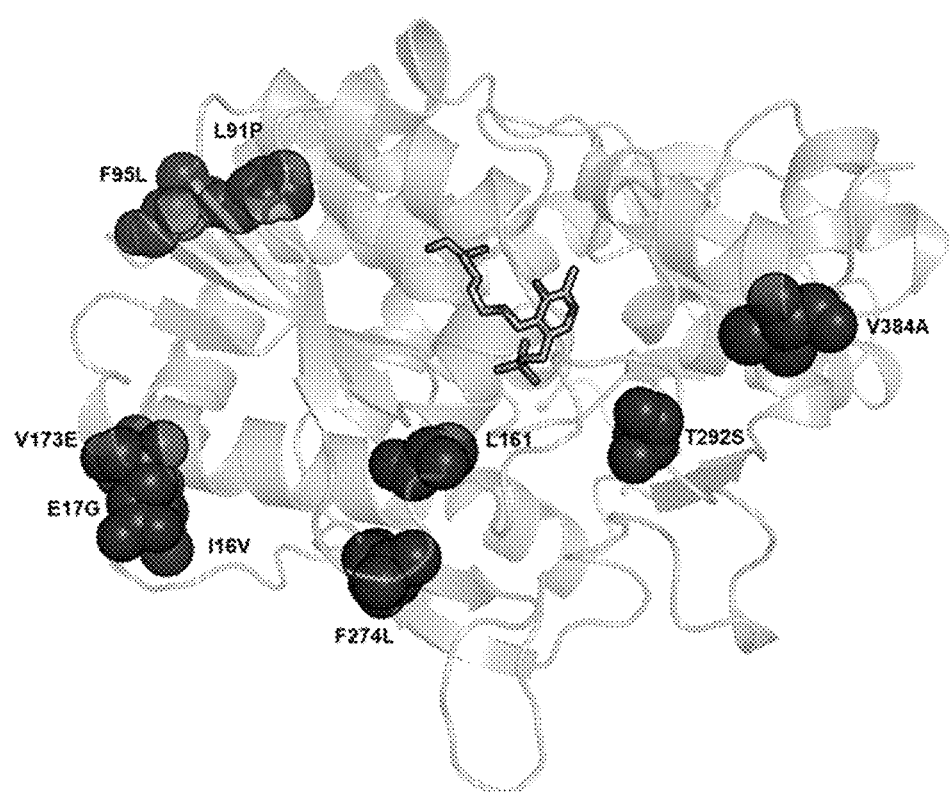
FIG. 7A shows that PfTrpB$^{7E6}$ contains nine mutations relative to wild-type PfTrpB (PDB: 6CUV). The mutations are distributed throughout the enzyme and are indicated in red.

During directed evolution, PfTrpB was altered by the introduction of nine mutations. Although PfTrpB$^{7E6}$ has only a single mutation in the active site (FIG. 7A); mutations governing enzyme activity are scattered throughout the protein. Remote mutations may be beneficial by affecting the enzyme's conformational dynamics, which are intrinsically linked to the catalytic cycle of PfTrpB (FIG. 2, top scheme). In its resting state, PfTrpB binds PLP as E(Ain) with the mobile communication (COMM) domain in a predominantly open conformation. Addition of an amino acid substrate induces formation of the external aldimine (E(Aex$_1$)), which is accompanied by a partially closed state. Dehydration to form the electrophilic E(A-A) species occurs when TrpB populates a fully closed conformation, where it remains until product is formed. To examine the state of the PfTrpB$^{7E6}$ active site and its connection to the COMM domain conformational cycling, high-resolution X-ray crystal structures of PfTrpB$^{7E6}$ in the E(Ain) state, as well as with β-EtSer bound in the active site as E(A-A), were determined.

Crystallography. Seed stocks of wild-type PfTrpB were used to seed crystallization of PfTrpB$^{7E6}$. The wild-type PfTrpB crystal was obtained from a sitting drop against a 1-mL reservoir containing 24% PEG3350 and 50 mM Na HEPES, pH 7.85. The seed stock was prepared according to the classical Seed Bead method (Hampton Research) using 24% PEG3350 and 50 mM Na HEPES, pH 7.85 as stabilization buffer. The seed stock was diluted 2,000× in stabilization buffer before use. PfTrpB$^{7E6}$ crystals were grown in sitting drops against a 1-mL reservoir of 14% PEG3350 and 0.1 M Na HEPES (pH 7.85) with mother liquor comprised of 1.5 μL of 18.8 mg/mL PfTrpB$^{7E6}$ and 1.5 μL of 2,000× diluted seed stock.

Ligand-bound structures were determined by soaking PfTrpB$^{7E6}$ crystals with the substrate of interest. From a 50/50% (v/v) mixture containing 0.5 M β-DL-ethylserine in 0.2 M KPi buffer, pH 8.0 and stabilization buffer, 0.5 μL were added to the sitting drop and incubated for 2 hours. (2S)-β-isopropylserine was soaked into PfTrpB$^{7E6}$ crystals by adding powdered substrate directly to the sitting drop, mixing gently, and incubating for one hour.

Crystals were cryoprotected through oil immersion in Fomblin Y (Sigma) and flash-frozen in liquid nitrogen until diffraction. Diffraction data were collected remotely at the Stanford Synchrotron Radiation Laboratories on beamline 12-2. Crystals routinely diffracted at or below 2.0 Å, and the data were integrated and scaled using XDS and AIMLESS. A resolution cutoff of CC1/2>0.3 was applied along the strongest axis of diffraction. These data contributed to model quality as judged by R$_{free}$ in the final bin <0.4. Structures were solved using molecular replacement with PHASER, as implemented in CCP4. The search model comprised a single monomer of PfTrpB$^{2B9}$ (holo and (2S, 3R)-β-EtSer, PDB: 5VM5) or PfTrpB$^{4D11}$ ((2S, 3S)-β-iPrSer) with the additional mutation L161A and subjected to ten cycles of geometric idealization in REFMACS and removal of all ligands. Model-building was performed in Coot beginning with data processed at 2.4 Å, followed by subsequent inclusion of increasingly higher-resolution shells of data with relaxed geometric constraints. This procedure was particularly important for the structures of 3-L-ethylserine and 3-L-isopropylserine-bound PfTrpB$^{7E6}$, which contained a large rigid body motion of the COMM domain. Refinement was performed using REFMACS. The MolProbity server was used to identify rotamer flips and to identify clashes. After the protein, ligand, and solvent atoms were built, TLS operators were added to refinement, which resulted in substantial improvements in R$_{free}$ for the models. Crystallographic and refinement statistics are reported in Table 9.

Coordinates are deposited in the Protein Data Bank with ID codes 6CUV (holo PfTrpB$^{7E6}$), 6CUZ ((2S, 3R)-β-ethylserine-bound PfTrpB$^{7E6}$), and 6CUT ((2S, 3S)-β-isopropylserine-bound PfTrpB$^{7E6}$). For Table 9, values in parenthesis are for the highest resolution shell. R$_{merge}$ is Σ|Io−⟨I⟩|/ΣIo, where Io is the intensity of an individual reflection, and ⟨I⟩ is the mean intensity for multiply recorded reflections. R$_{work}$ is Σ‖Fo−Fc‖/Fo, where Fo is an observed amplitude and Fc a calculated amplitude; R$_{free}$ is the same statistic calculated over a 5% subset of the data that has not been included. Ramachandran statistics calculated by the MolProbity server.

TABLE 9

Crystallographic data collection and refinement statistics.

| Protein | PfTrpB$^{7E6}$ | PfTrp$^{7E6}$ | PfTrpB$^{7E6}$ |
|---|---|---|---|
| PDB ID Code | 6CUV | 6CUZ | 6CUT |
| Ligand | None | (2S, 3R)-β-ethylserine | (2S, 3S)-β-isopropylserine |
| Space Group | P2$_1$2$_1$2$_1$ | P2$_1$2$_1$2$_1$ | P2$_1$2$_1$2$_1$ |
| Cell dimensions, Å | a, b, c = 83.6, 108.6, 159.3 | a, b, c = 84.2, 109.3, 159.9 | a, b, c = 82.2, 107.4, 159.3 |
| Cell angles | α = β = γ = 90° | α = β = γ = 90° | α = β = γ = 90° |
| Data Collection | | | |
| Wavelength, Å | 1.19499 | 1.19499 | 0.97946 |
| Beamline | SSRL 12.2 | SSRL 12.2 | SSRL 12.2 |
| Resolution, Å | 40-2.26 | 40-1.75 | 40-1.77 |
| Last bin (Å) | 2.31-2.26 | 1.78-1.75 | 1.80-1.77 |
| No. observations | 422,578 | 610,237 | 920,320 |
| Completeness (%) | 100.0 (100.0) | 100.0 (100.0) | 99.9 (99.9) |
| R$_{pim}$ (%) | 0.058 (0.719) | 0.050 (0.613) | 0.030 (1.25) |
| CC(1/2) | 0.990 (0.655) | 0.981 (0.753) | 0.998 (0.452) |
| I/σI | 8.9 (1.0) | 8.2 (0.8) | 12.0 (0.6) |
| Redundancy | 6.2 (6.2) | 4.1 (4.1) | 6.7 (6.7) |
| Refinement | | | |
| Total no. of reflections | 63,878 | 141,404 | 130,162 |
| Total no. of atoms | 11,687 | 11,996 | 11,972 |
| Final bin (Å) | 2.32-2.26 | 1.80-1.75 | 1.82-1.77 |
| R$_{work}$ (%) | 21.1 (36.3) | 23.5 (36.7) | 19.3 (39.5) |
| R$_{free}$ (%) | 25.9 (38.3) | 26.1 (38.0) | 22.5 (40.1) |
| Average B factor, Å$^2$ | 26.1 | 14.8 | 24.7 |
| Ramachandran plot favored, % | 97 | 98 | 98 |
| Allowed, % | 99.8 | 99.9 | 99.8 |
| Outliers, % | 0.2 | 0.1 | 0.2 |

Figure 5A:
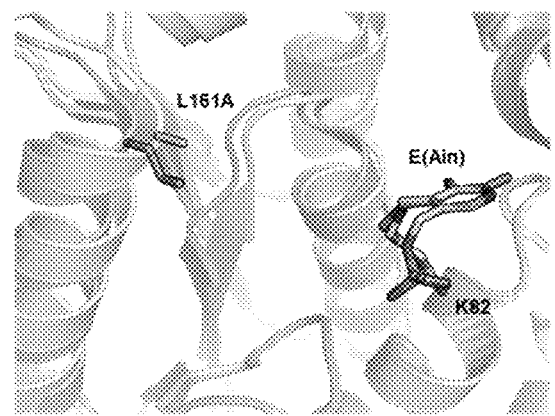
FIG. 5A shows substrate binding and conformational changes in PfTrpB$^{7E6}$. Holo PfTrpB$^{7E6}$ (PDB: 6CUV) shown as E(Ain) assumes a partially closed conformation when compared to wild-type PfTrpB (PDB: 5DVZ, gray).
Figure 5B:
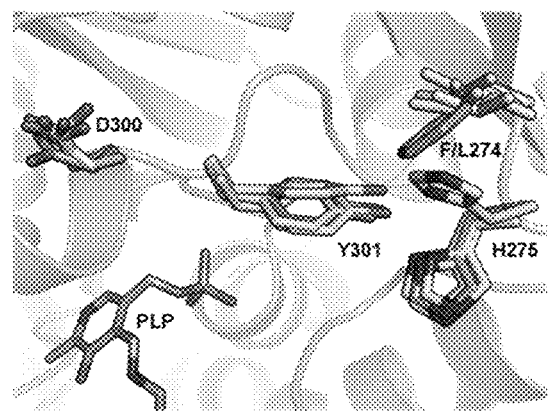
FIG. 5B shows that residues H275 and D300 undergo rotameric shifts toward the closed conformation.
Figure 7B:
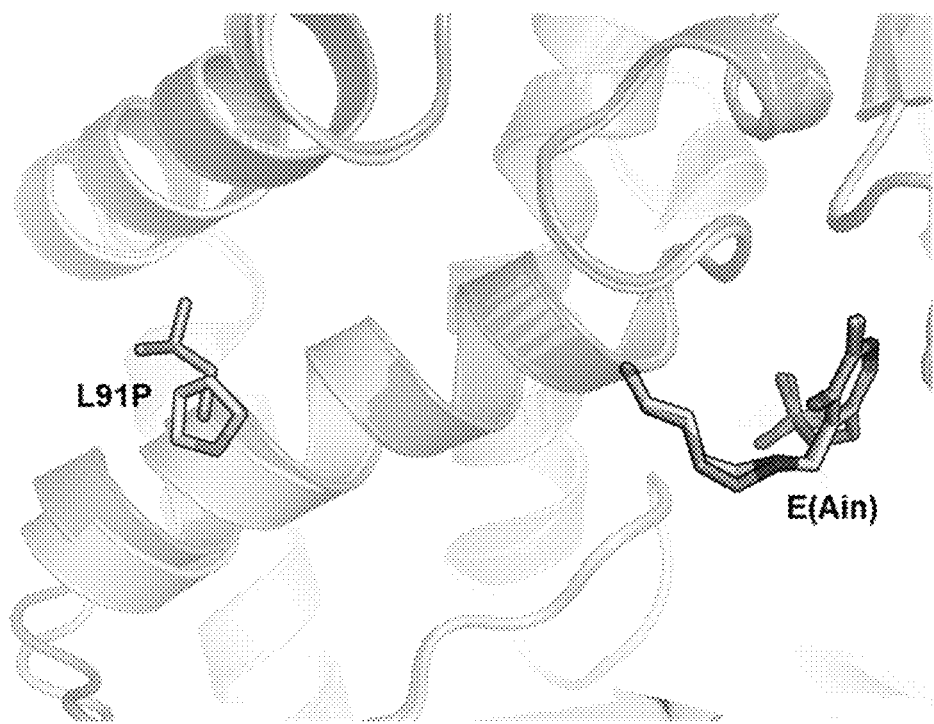
FIG. 7B shows that L91P kinks the α-helix adjacent to both the catalytic lysine and the COMM domain.

Discussion. Whereas ancestor enzymes were largely identical to wild-type PfTrpB (PDB: 5DVZ) in an open state, the COMM domain of PfTrpB$^{7E6}$ (2.26-Å, PDB: 6CUV) and key residues close to the active site showed preorganization toward more closed conformations. Specifically, in half of the protomers, the COMM domain has shifted into a partially closed conformation even in the absence of substrate (FIG. 5A). While many residues may be contributing to the stabilization of this state, it was hypothesized that the mutation L91P destabilizes open states; this residue lies on an α-helix immediately prior to the COMM domain in sequence space and causes a kink in the helix that shifts the structure toward more closed states (FIG. 7B). Within the active site, D300 has been previously observed to undergo a rotameric shift associated with E(A-A) formation and the closed state. Here, it was discovered that D300 was preorganized in the closed conformation in the absence of any substrate (FIG. 5B). It was also observed that one rotamer of H275 had shifted conformations, presumably to enable the diffusion of indole into the active site. Cumulatively, these structural changes strongly suggest that remote mutations increased activity by promoting the closed conformation and thereby increasing the persistence of the E(A-A) intermediate.

Figure 5C:
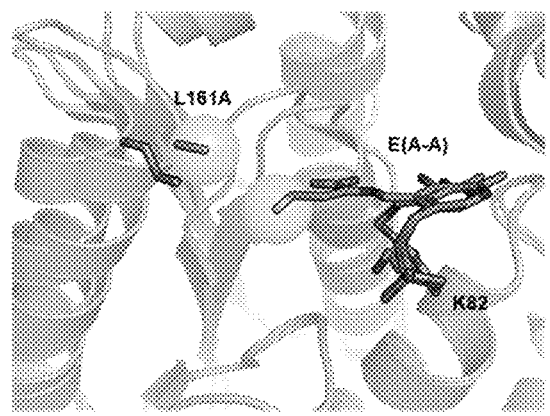
FIG. 5C shows substrate binding and conformational changes in PfTrpB$^{7E6}$. β-EtSer is found in PfTrpB$^{7E6}$ as E(A-A) (PDB: 6CUZ) and shows closure of the COMM domain. Spheres represent the Van der Waals radii.
Figure 5D:
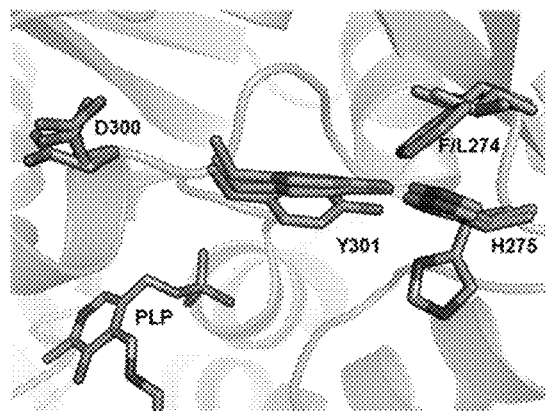
FIG. 5D shows that residues D300, Y301, and H275 undergo rotameric shifts associated with the closed conformation.

Next, PfTrpB[7E6] was soaked with β-EtSer and obtained a 1.75-Å structure with β-EtSer bound as E(A-A) in two protomers (PDB: 6CUZ) (FIG. 5C). As expected, the COMM domain undergoes rigid-body motion to the closed conformation where the steric complementarity between the longer β-alkyl chain and L161A becomes apparent. Notably, the L161A mutation does not appear to induce significant alterations elsewhere in the active site (FIG. 5D) and there is space to accommodate even longer β-branched substituents as well as a range of indole nucleophiles in the active site.

Example 5. Preparation of Non-Canonical Tryptophan Analogs Using TrpB Catalysts

Because one goal of the present study was to evolve a versatile β-branched ncAA synthase, the PfTrpB[7E6] substrate scope was explored.

General methods. Chemicals and reagents were purchased from commercial sources and used without further purification. Proton and carbon NMR spectra were recorded on a Bruker 400 MHz (100 MHz) spectrometer equipped with a cryogenic probe. Proton chemical shifts are reported in ppm (δ) relative to tetramethylsilane and calibrated using the residual solvent resonance (DMSO, δ 2.50 ppm). Data are reported as follows: chemical shift (multiplicity [singlet (s), doublet (d), doublet of doublets (dd), doublet of doublets of doublets (ddd), triplet (t), triplet of doubles (td), multiplet (m)], coupling constants [Hz], integration). Carbon NMR spectra were recorded with complete proton decoupling. Carbon chemical shifts are reported in ppm relative to tetramethylsilane and calibrated using the residual solvent proton resonance as an absolute reference. All NMR spectra were recorded at ambient temperature (about 25° C.). Preparative reversed-phase chromatography was performed on a Biotage Isolera One purification system, using C-18 silica as the stationary phase, with $CH_3OH$ as the strong solvent and $H_2O$ (0.1% HCl by weight) as the weak solvent. Liquid chromatography/mass spectrometry (LCMS) was performed on an Agilent 1290 UPLC-LCMS equipped with a C-18 silica column (1.8 µm, 2.1×50 mm) using $CH_3CN/H_2O$ (0.1% acetic acid by volume): 5% to 95% $CH_3CN$ over 4 min; 1 mL/min.

Synthesis and characterization of tryptophan analogs. Preparative reactions were carried out by adding 100 µmol of nucleophile substrate and 200 µmol L-amino acid substrate to a 40-mL reaction vial. Following substrate addition, 10 mL of 50 mM KPi buffer, pH 8.0 containing purified PfTrpB[2G8] at 0.01-0.4% catalyst loading. PfTrpB[2G8] (PfTrpB[7E6]+M139L, N166D, S335N-L91P) is a variant with activity and expression levels comparable to PfTrpB[7E6]. The reaction mixture was incubated in a 75° C. water bath for 24 hours, frozen on dry ice, and then the water was removed by lyophilization. Approximately 4 mL of 1:1 $CH_3CN$/1 M aq. HCl were added to the remaining solid and the volume was reduced in vacuo. The sample was resuspended in water and loaded onto a 12 g C-18 column equilibrated with 1% methanol/water (0.1% HCl by mass) on a Biotage Isolera One purification system. The column was washed with three column volumes (CV) of 1% methanol/water mixture. The product was the eluted with a gradient from 1% to 100% methanol over 10 CV. The fractions containing the UV-active product were combined and the volume reduced in vacuo. The product was then suspended in water (0.1% HCl by mass) and transferred to a tared vial before being frozen on dry ice and lyophilized. Yields were determined by product mass following lyophilization relative to theoretical yield with indole analog as the limiting reagent. Products were obtained as hydrochloride salts and product identities were confirmed by $^1$H- and $^{13}$C-NMR and high-resolution mass spectrometry.

Determination of Optical Purity. Product optical purity was estimated by derivatization with FDNP-alanamide. Approximately 0.5 µmol of purified β-MeTrp, β-MeTrp, or β-MeTrp were added to a 2-mL vial. The product was resuspended in 100 µL of 1 M aq. $NaHCO_3$. FDNP-alanamide (10 µL of a 33-mM solution in acetone, 0.33 µmol) was added to each vial, followed by a two-hour incubation at 37° C. and 230 rpm. The reaction mixture was then cooled to room temperature and diluted with 1:1 $CH_3CN$/1-M aq. HCl (600 µL). The resulting solution was analyzed directly by LCMS at 330 nm. Each amino acid was derivatized with both racemic and enantiopure FDNP-alanamide for comparison. Absolute stereochemistry was inferred by analogy to L-tryptophan. All products were >99% ee.

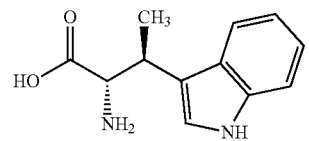 [SMILES: C[C@@H](c1c[nH]c2ccccc12)[C@H](N)C(=O)O]

β-Methyltryptophan. $^1$H NMR (400 MHz, $D_2O$) δ7.66 (dt, J=8.0, 0.9 Hz, 1H), 7.49 (dt, J=8.2, 0.9 Hz, 1H), 7.32 (s, 1H), 7.23 (ddd, J=8.3, 6.8, 1.1 Hz, 1H), 7.13 (ddt, J=7.9, 7.0, 0.8 Hz, 1H), 4.23 (d, J=5.5 Hz, 1H), 3.85 (qd, J=7.3, 5.4 Hz, 1H), 1.53 (d, J=7.3 Hz, 3H). $^{13}$C NMR (101 MHz, $D_2O$) δ171.87, 136.35, 125.56, 124.20, 122.28, 119.49, 118.67, 112.08, 57.91, 32.26, 17.29. HRMS (FAB+) (m/z) for [M+H]$^+$ $C_{12}H_{15}N_2O_2$ requires 219.1134, observed 219.1113.

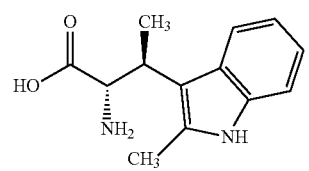 [SMILES: Cc1[nH]c2ccccc2c1[C@H](C)[C@H](N)C(=O)O]

β-Methyl-2-methyltryptophan. $^1$H NMR (400 MHz, $D_2O$) δ7.61 (dt, J=7.8, 1.0 Hz, 1H), 7.39 (dt, J=8.1, 0.9 Hz, 1H), 7.14 (ddd, J=8.1, 7.0, 1.2 Hz, 1H), 7.07 (ddd, J=8.1, 7.0, 1.2 Hz, 1H), 4.28 (d, J=9.4 Hz, 1H), 3.49 (dq, J=9.4, 7.1 Hz, 1H), 2.35 (s, 3H), 1.51 (d, J=7.2 Hz, 3H). $^{13}$C NMR (101 MHz, $D_2O$) δ171.89, 135.64, 134.86, 125.73, 121.22, 119.31, 118.27, 111.41, 107.25, 57.63, 33.00, 16.77, 10.88. HRMS (FAB+) (m/z) for [M+H]$^+$ $C_{13}H_{17}N_2O_2$ requires 233.1290, observed 233.1278.

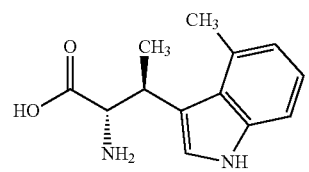 [SMILES: Cc1cccc2[nH]cc([C@H](C)[C@H](N)C(=O)O)c12]

β-Methyl-4-methyltryptophan. ¹H NMR (400 MHz, D₂O) δ 7.33 (d, J=7.3 Hz, 2H), 7.10 (dd, J=8.2, 7.1 Hz, 1H), 6.89 (dt, J=7.1, 1.0 Hz, 1H), 4.24 (d, J=7.0 Hz, 1H), 4.08-3.98 (m, 1H), 2.64 (s, 3H), 1.44 (d, J=7.1 Hz, 3H). ¹³C NMR (101 MHz, D₂O) δ 171.29, 136.31, 130.16, 124.17, 123.11, 122.22, 121.29, 114.44, 109.96, 58.50, 32.59, 19.56, 18.53. HRMS (FAB+) (m/z) for [M+H]⁺C₁₃H₁₇N₂O₂ requires 233.1290, observed 233.1297.

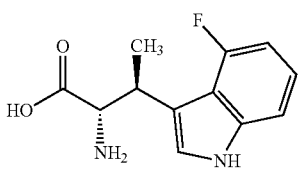 [SMILES: C[C@@H](c1c[nH]c2cccc(F)c12)[C@H](N)C(=O)O]

β-Methyl-4-fluorotryptophan. ¹H NMR (400 MHz, D₂O) δ 7.24 (d, J=8.1 Hz, 2H), 7.11 (td, J=8.0, 5.2 Hz, 1H), 6.78 (ddd, J=12.0, 7.9, 0.7 Hz, 1H), 4.21 (d, J=6.7 Hz, 1H), 3.71 (p, J=7.0 Hz, 1H), 1.47-1.40 (m, 3H). ¹³C NMR (101 MHz, D₂O) δ 171.57, 157.25, 154.84, 139.42, 139.30, 124.56, 122.70, 122.62, 114.00, 113.80, 111.18, 111.15, 108.28, 108.24, 104.53, 104.33, 58.14, 58.11, 33.21, 16.85, 16.83. FIRMS (FAB+) (m/z) for [M+H]⁺ C₁₂H₁₄FN₂O₂ requires 237.1039, observed 237.1011.

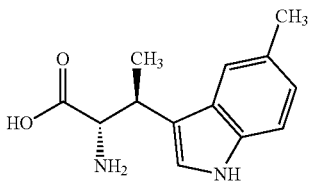 [SMILES: Cc1ccc2[nH]cc([C@H](C)[C@H](N)C(=O)O)c2c1]

β-Methyl-5-methyltryptophan. ¹H NMR (400 MHz, D₂O) δ 7.40 (dt, J=1.8, 0.9 Hz, 1H), 7.32 (d, J=8.3 Hz, 1H), 7.19 (s, 1H), 7.01 (dd, J=8.3, 1.5 Hz, 1H), 4.11 (d, J=6.1 Hz, 1H), 3.42 (dt, J=10.1, 5.9 Hz, 1H), 2.31 (s, 3H), 1.93-1.75 (m, 2H), 0.75 (t, J=7.3 Hz, 3H). ¹³C NMR (101 MHz, D₂O) δ 172.63, 134.73, 129.20, 126.51, 124.96, 123.75, 118.11, 111.90, 109.50, 57.49, 39.87, 24.60, 20.48, 11.41. HRMS (FAB+) (m/z) for [M+H]⁺ C₁₃H₁₇N₂O₂ requires 233.1290, observed 233.1291.

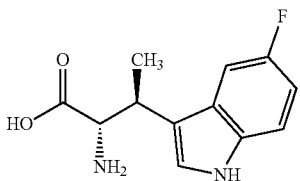 [SMILES: C[C@@H](c1c[nH]c2ccc(F)cc12)[C@H](N)C(=O)O]

β-Methyl-5-fluorotryptophan. ¹H NMR (400 MHz, D₂O) δ 7.41-7.29 (m, 2H), 7.25 (dd, J=10.3, 2.5 Hz, 1H), 6.95 (td, J=9.3, 2.5 Hz, 1H), 4.18 (d, J=5.2 Hz, 1H), 3.72 (qd, J=7.3, 5.0 Hz, 1H), 1.44 (d, J=7.3 Hz, 3H). ¹³C NMR (101 MHz, D₂O) δ 171.62, 158.54, 156.24, 132.85, 125.83, 125.74, 112.82, 112.72, 112.07, 112.03, 110.52, 110.26, 103.33, 103.09, 57.69, 32.05, 17.06. HRMS (FAB+) (m/z) for [M+H]⁺ C₁₂H₁₃FN₂O₂ requires 237.1039, observed 237.1031.

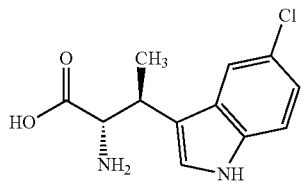 [SMILES: C[C@@H](c1c[nH]c2ccc(Cl)cc12)[C@H](N)C(=O)O]

β-Methyl-5-chlorotryptophan. ¹H NMR (400 MHz, D₂O) δ 7.66 (d, J=1.9 Hz, 1H), 7.43 (d, J=8.7 Hz, 1H), 7.35 (s, 1H), 7.19 (dd, J=8.7, 1.9 Hz, 1H), 4.17 (d, J=5.5 Hz, 1H), 3.85-3.73 (m, 1H), 1.52 (d, J=7.3 Hz, 3H). ¹³C NMR (101 MHz, D₂O) δ 172.11, 134.79, 126.68, 125.55, 124.56, 122.22, 117.95, 113.18, 112.04, 58.15, 32.20, 17.22. HRMS (FAB+) (m/z) for [M+H]⁺ C₁₂H₁₄ClN₂O₂ requires 253.0744, observed 253.0740.

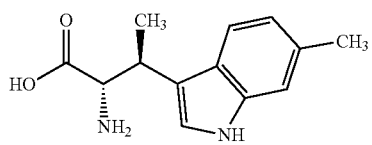 [SMILES: Cc1ccc2c([C@H](C)[C@H](N)C(=O)O)c[nH]c2c1]

β-Methyl-6-methyltryptophan. ¹H NMR (400 MHz, D₂O) δ 7.53 (d, J=8.2 Hz, 1H), 7.29 (dt, J=1.6, 0.8 Hz, 1H), 7.23 (s, 1H), 6.98 (dd, J=8.2, 1.4 Hz, 1H), 4.21 (d, J=5.5 Hz, 1H), 3.80 (qd, J=7.2, 5.3 Hz, 1H), 2.39 (s, 3H), 1.50 (d, J=7.3 Hz, 3H). ¹³C NMR (101 MHz, D₂O) δ 171.80, 136.87, 132.59, 123.57, 123.41, 121.14, 118.49, 111.89, 111.71, 57.83, 32.31, 20.58, 17.29. HRMS (FAB+) (m/z) for [M+H]⁺ C₁₃H₁₇N₂O₂ requires 233.1290 observed 233.1283.

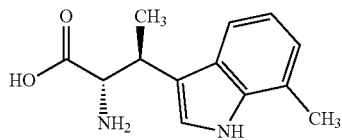 [SMILES: Cc1cccc2c([C@H](C)[C@H](N)C(=O)O)c[nH]c12]

β-Methyl-7-methyltryptophan. ¹H NMR (400 MHz, D₂O) δ 7.50-7.43 (m, 1H), 7.31 (s, 1H), 7.07-6.98 (m, 2H), 4.22 (d, J=5.4 Hz, 1H), 3.86-3.74 (m, 1H), 2.43 (d, J=0.9 Hz, 3H), 1.49 (d, J=7.3 Hz, 3H). ¹³C NMR (101 MHz, D₂O) δ 171.63, 135.84, 125.23, 123.98, 122.45, 122.06, 119.79, 116.26, 112.47, 57.74, 32.28, 17.21, 15.85. HRMS (FAB+) (m/z) for [M+H]⁺ C₁₃H₇N₂O₂ requires 233.1290, observed 233.1281.

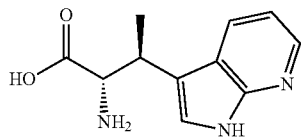 [SMILES: C[C@@H](c1c[nH]c2ncccc12)[C@H](N)C(=O)O]

β-Methyl-7azatryptophan. ¹H NMR (400 MHz, D₂O) δ 8.68 (dd, J=8.1, 1.2 Hz, 1H), 8.35 (dd, J=6.1, 1.1 Hz, 1H), 7.68 (s, 1H), 7.55 (dd, J=8.1, 6.0 Hz, 1H), 4.32 (d, J=4.8 Hz, 1H), 4.06-3.94 (m, 1H), 1.56 (d, J=7.4 Hz, 3H). ¹³C NMR (101 MHz, D₂O) δ 171.07, 138.47, 136.99, 132.90, 127.86, 124.76, 115.43, 114.35, 57.55, 31.33, 16.30. HRMS (FAB+) (m/z) for [M+H]⁺ C₁₁H₁₁N₃O₂²H₂ requires 221.1133, observed 221.1144.

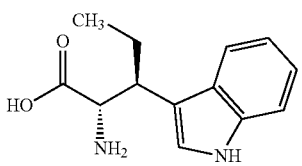 [SMILES: CC[C@@H](c1c[nH]c2ccccc12)[C@H](N)C(=O)O]

β-Ethyltryptophan. $^1$H NMR (400 MHz, D$_2$O) δ 7.66 (dt, J=8.0, 1.0 Hz, 1H), 7.50 (dt, J=8.2, 0.9 Hz, 1H), 7.31 (s, 1H), 7.23 (ddd, J=8.2, 7.0, 1.2 Hz, 1H), 7.13 (ddd, J=8.1, 7.1, 1.1 Hz, 1H), 4.28 (d, J=5.5 Hz, 1H), 3.61 (dt, J=9.8, 5.8 Hz, 1H), 2.03-1.83 (m, 2H), 0.84 (t, J=7.3 Hz, 3H). $^{13}$C NMR (101 MHz, D$_2$O) δ 172.00, 136.36, 126.28, 124.75, 122.27, 119.49, 118.63, 112.07, 109.76, 56.92, 39.52, 24.61, 11.38. HRMS (FAB+) (m/z) for [M+H]$^+$ C$_{13}$H$_{17}$N$_2$O$_2$ requires 233.1290, observed 233.1293.

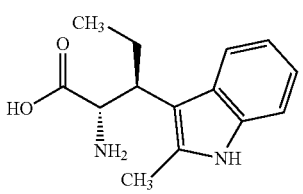 [SMILES: CC[C@@H](c1c(C)[nH]c2ccccc12)[C@H](N)C(=O)O]

β-Ethyl-2-methyltryptophan. $^1$H NMR (400 MHz, D$_2$O) δ 7.62-7.56 (m, 1H), 7.41 (dt, J=8.1, 0.9 Hz, 1H), 7.14 (ddd, J=8.1, 7.0, 1.1 Hz, 1H), 7.07 (ddd, J=8.2, 7.1, 1.2 Hz, 1H), 4.32 (d, J=9.2 Hz, 1H), 3.31-3.20 (m, 1H), 2.36 (s, 3H), 2.10-1.96 (m, 1H), 1.96-1.84 (m, 1H), 0.65 (t, J=7.3 Hz, 3H). $^{13}$C NMR (101 MHz, D$_2$O) δ 172.18, 136.36, 135.67, 125.90, 121.19, 119.30, 118.14, 111.40, 104.83, 57.21, 40.33, 23.45, 11.21, 10.94. HRMS (FAB+) (m/z) for [M+H]$^+$ C$_{14}$H$_{19}$N$_2$O$_2$ requires 247.1447, observed 247.1445.

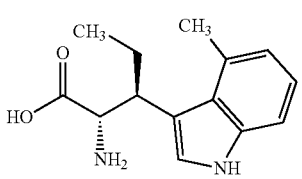 [SMILES: CC[C@@H](c1c[nH]c2cccc(C)c12)[C@H](N)C(=O)O]

β-Ethyl-4-methyltryptophan. $^1$H NMR (400 MHz, D$_2$O) δ 7.40-7.29 (m, 2H), 7.12 (dd, J=8.2, 7.1 Hz, 1H), 6.90 (dt, J=7.1, 1.0 Hz, 1H), 4.18 (d, J=6.7 Hz, 1H), 3.91 (s, 1H), 2.66 (s, 3H), 1.99-1.86 (m, 1H), 1.86-1.71 (m, 1H), 0.85 (t, J=7.3 Hz, 3H). $^{13}$C NMR (101 MHz, D$_2$O) δ172.08, 136.22, 130.38, 125.44, 123.61, 122.16, 121.50, 111.88, 110.10, 58.37, 39.19, 26.73, 20.00, 10.92. HRMS (FAB+) (m/z) for [M+H]$^+$ C$_{14}$H$_{19}$N$_2$O$_2$ requires 247.1447, observed 247.1448.

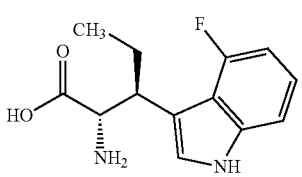 [SMILES: CC[C@@H](c1c[nH]c2cccc(F)c12)[C@H](N)C(=O)O]

β-Ethyl-4-fluorotryptophan. $^1$H NMR (400 MHz, D$_2$O) δ 7.30-7.23 (m, 2H), 7.11 (td, J=8.0, 5.2 Hz, 1H), 6.78 (ddd, J=12.0, 7.9, 0.8 Hz, 1H), 4.21 (d, J=7.1 Hz, 1H), 3.52-3.41 (m, 1H), 1.90-1.75 (m, 2H), 0.71 (t, J=7.3 Hz, 3H). $^{13}$C NMR (101 MHz, D$_2$O) δ 171.95, 157.32, 154.91, 139.54, 139.42, 125.66, 122.63, 122.55, 114.47, 114.27, 108.42, 108.38, 108.31, 108.28, 104.59, 104.39, 57.50, 57.47, 40.66, 24.50, 24.47, 11.31. HRMS (FAB+) (m/z) for [M+H]$^+$ C$_{13}$H$_{16}$FN$_2$O$_2$ requires 251.1196, observed 251.1186.

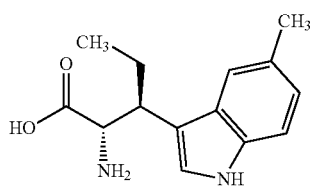 [SMILES: CC[C@@H](c1c[nH]c2ccc(C)cc12)[C@H](N)C(=O)O]

β-Ethyl-5-methyltryptophan. $^1$H NMR (400 MHz, D$_2$O) δ 7.40 (dt, J=1.8, 0.9 Hz, 1H), 7.32 (d, J=8.3 Hz, 1H), 7.19 (s, 1H), 7.01 (dd, J=8.3, 1.5 Hz, 1H), 4.11 (d, J=6.1 Hz, 1H), 3.42 (dt, J=10.1, 5.9 Hz, 1H), 2.31 (s, 3H), 1.93-1.75 (m, 2H), 0.75 (t, J=7.3 Hz, 3H). $^{13}$C NMR (101 MHz, D$_2$O) δ 172.63, 134.73, 129.20, 126.51, 124.96, 123.75, 118.11, 111.90, 109.50, 57.49, 39.87, 24.60, 20.48, 11.41. HRMS (FAB+) (m/z) for [M+H]$^+$ C$_{14}$H$_{19}$N$_2$O$_2$ requires 247.1447, observed 247.1451.

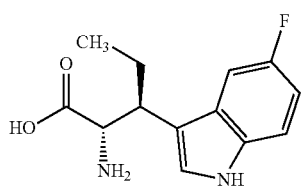 [SMILES: CC[C@@H](c1c[nH]c2ccc(F)cc12)[C@H](N)C(=O)O]

β-Ethyl-5-fluorotryptophan. $^1$H NMR (400 MHz, D$_2$O) δ 7.40 (dd, J=8.9, 4.6 Hz, 1H), 7.34-7.24 (m, 2H), 6.97 (td, J=9.3, 2.5 Hz, 1H), 4.24 (d, J=5.3 Hz, 1H), 3.51 (td, J=7.9, 5.3 Hz, 1H), 1.87 (p, J=7.4 Hz, 2H), 0.80 (t, J=7.3 Hz, 3H). $^{13}$C NMR (101 MHz, D$_2$O) δ 171.94, 158.60, 156.30, 132.90, 126.59, 126.49, 126.31, 112.83, 112.73, 110.54, 110.28, 109.94, 109.89, 103.35, 103.11, 56.78, 39.37, 24.47, 11.32. HRMS (FAB+) (m/z) for [M+H]$^+$ C$_{13}$H$_{16}$FN$_2$O$_2$ requires 251.1196, observed 251.1186.

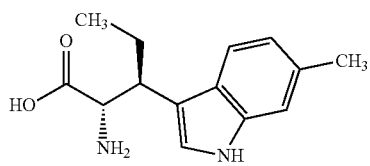 [SMILES: CC[C@@H](c1c[nH]c2cc(C)ccc12)[C@H](N)C(=O)O]

β-Ethyl-6-methyltryptophan. $^1$H NMR (400 MHz, D$_2$O) δ 7.54 (d, J=8.2 Hz, 1H), 7.31 (s, 1H), 7.22 (s, 1H), 6.99 (d, J=8.2 Hz, 1H), 4.23 (d, J=5.7 Hz, 1H), 3.54 (dt, J=9.7, 5.9 Hz, 1H), 2.40 (s, 3H), 2.02-1.82 (m, J=6.7 Hz, 2H), 0.83 (t, J=7.2 Hz, 3H). $^{13}$C NMR (101 MHz, D$_2$O) δ 172.23, 136.89, 132.57, 124.13, 124.10, 121.13, 118.50, 111.71, 109.74, 57.11, 39.70, 24.61, 20.58, 11.40. HRMS (FAB+) (m/z) for [M+H]$^+$ C$_{14}$H$_{19}$N$_2$O$_2$ requires 247.1447, observed 247.1444.

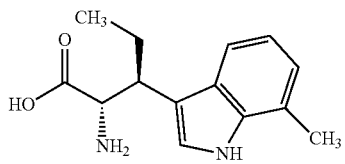 [SMILES: CC[C@@H](c1c[nH]c2c(C)cccc12)[C@H](N)C(=O)O]

β-Ethyl-7-methyltryptophan. ¹H NMR (400 MHz, D$_2$O) δ 7.49-7.39 (m, 1H), 7.28 (d, J=4.4 Hz, 1H), 7.05-6.93 (m, 2H), 4.23 (t, J=4.0 Hz, 1H), 3.52 (td, J=8.7, 4.1 Hz, 1H), 2.42 (d, J=5.7 Hz, 3H), 1.86 (dtd, J=13.5, 7.8, 5.4 Hz, 2H), 0.82-0.71 (m, 3H). ¹³C NMR (101 MHz, D$_2$O) δ 171.90, 135.85, 125.96, 124.48, 122.43, 121.99, 119.77, 116.25, 110.19, 56.85, 39.60, 24.60, 15.87, 11.38. HRMS (FAB+) (m/z) for [M+H]$^+$ C$_{14}$H$_{19}$N$_2$O$_2$ requires 247.1447, observed 247.1448.

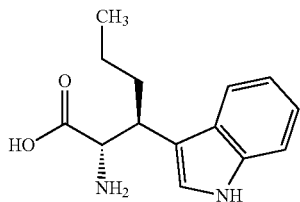

β-Propyltryptophan. ¹H NMR (400 MHz, D$_2$O) δ 7.65 (dt, J=8.1, 1.0 Hz, 1H), 7.49 (dt, J=8.0, 0.8 Hz, 1H), 7.29 (s, 1H), 7.22 (ddd, J=8.1, 6.9, 1.1 Hz, 1H), 7.12 (ddd, J=8.1, 7.1, 1.1 Hz, 1H), 4.23 (d, J=5.7 Hz, 1H), 3.69 (dt, J=10.8, 5.4 Hz, 1H), 2.00-1.87 (m, 1H), 1.86-1.76 (m, 1H), 1.26-1.14 (m, 2H), 0.81 (t, J=7.4 Hz, 3H). ¹³C NMR (101 MHz, D$_2$O) δ 172.05, 136.35, 126.21, 124.74, 122.24, 119.48, 118.63, 112.07, 109.92, 57.26, 37.36, 33.31, 20.01, 12.84. HRMS (FAB+) (m/z) for [M+H]$^+$ C$_{14}$H$_{19}$N$_2$O$_2$ requires 247.1447, observed 247.1456.

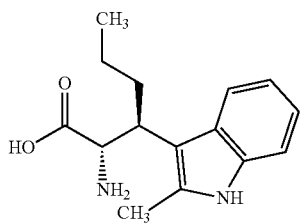 [SMILES: CCC[C@@H](c1c(C)[nH]c2ccccc12)[C@H](N)C(=O)O]

β-Propyl-2-methyltryptophan. ¹H NMR (400 MHz, D$_2$O) δ 7.65 (d, J=7.9 Hz, 1H), 7.42 (dt, J=8.1, 1.0 Hz, 1H), 7.17 (ddd, J=8.2, 7.1, 1.2 Hz, 1H), 7.10 (ddd, J=8.1, 7.1, 1.2 Hz, 1H), 4.27 (d, J=9.2 Hz, 1H), 3.34 (d, J=15.7 Hz, 1H), 2.38 (s, 3H), 2.11 (tt, J=13.2, 7.0 Hz, 1H), 1.80 (dtd, J=12.6, 8.0, 4.4 Hz, 1H), 1.07 (h, J=7.4 Hz, 2H), 0.77 (t, J=7.3 Hz, 3H). ¹³C NMR (101 MHz, D$_2$O) δ 172.66, 135.67, 121.21, 119.30, 118.23, 111.38, 105.31, 57.76, 38.31, 32.23, 30.23, 30.23, 20.04, 12.89, 10.82. HRMS (FAB+) (m/z) for [M+H]$^+$ C$_{15}$H$_{21}$N$_2$O$_2$ requires 261.1603, observed 261.1611.

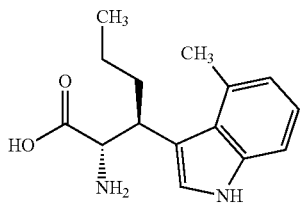 [SMILES: CCC[C@@H](c1c[nH]c2cccc(C)c12)[C@H](N)C(=O)O]

β-Propyl-4-methyltryptophan. ¹NMR (400 MHz, D$_2$O) δ 7.39-7.30 (m, 2H), 7.11 (dd, J=8.2, 7.1 Hz, 1H), 6.89 (d, J=7.0 Hz, 1H), 4.13 (d, J=6.4 Hz, 1H), 3.94 (d, J=37.8 Hz, 1H), 2.66 (s, 3H), 1.89-1.72 (m, 2H), 1.25 (p, J=7.3 Hz, 2H), 0.82 (t, J=7.3 Hz, 3H). ¹³C NMR (101 MHz, D$_2$O) δ 172.15, 136.13, 130.27, 125.22, 123.58, 122.04, 121.42, 112.06, 110.00, 58.66, 37.26, 35.62, 19.75, 13.03, 12.76. HRMS (FAB+) (m/z) for [M+H]$^+$ C$_{15}$H$_{16}$N$_2$O$_2$²H$_3$ requires 262.1640, observed 262.1635.

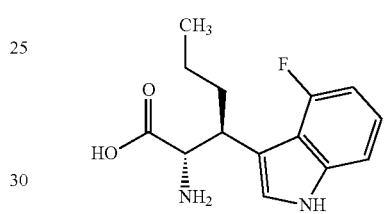

β-Propyl-4-fluorotryptophan. ¹H NMR (400 MHz, D$_2$O) δ 7.34-7.26 (m, 2H), 7.15 (td, J=8.0, 5.2 Hz, 1H), 6.83 (dd, J=12.1, 7.8 Hz, 1H), 4.20 (d, J=7.3 Hz, 1H), 3.59 (dd, J=10.6, 5.6 Hz, 1H), 1.99-1.87 (m, 1H), 1.84-1.73 (m, 1H), 1.23-1.07 (m, 2H), 0.80 (t, J=7.4 Hz, 3H). ¹³C NMR (101 MHz, D$_2$O) δ 172.19, 157.32, 154.90, 139.55, 139.43, 125.67, 122.68, 122.60, 108.76, 108.73, 108.32, 108.29, 104.63, 104.43, 94.96, 57.93, 38.54, 38.18, 33.24, 19.97, 12.78. HRMS (FAB+) (m/z) for [M+H]$^+$ C$_{14}$H$_{15}$FN$_2$O$_2$²H$_3$ requires 268.1541, observed 268.1531.

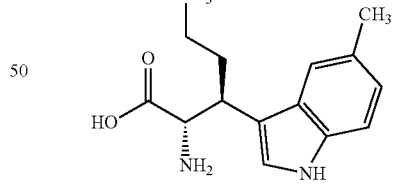

β-Propyl-5-methyltryptophan. ¹H NMR (400 MHz, D$_2$O) δ 7.50 (dt, J=1.7, 0.9 Hz, 1H), 7.47-7.37 (m, 1H), 7.27 (s, 1H), 7.09 (dd, J=8.3, 1.6 Hz, 1H), 4.13 (d, J=6.4 Hz, 1H), 3.57 (dt, J=11.2, 5.9 Hz, 1H), 2.40 (s, 3H), 1.97 (dddd, J=13.8, 11.0, 8.7, 5.5 Hz, 1H), 1.80 (td, J=13.4, 7.7 Hz, 1H), 1.27-1.14 (m, 2H), 0.82 (t, J=7.4 Hz, 3H). ¹³C NMR (101 MHz, D$_2$O) δ 172.93, 134.74, 129.18, 126.43, 124.96, 123.72, 118.16, 111.91, 109.80, 58.17, 37.76, 33.36, 20.48, 20.03, 12.85. HRMS (FAB+) (m/z) for [M+H]$^+$ C$_{15}$H$_{18}$N$_2$O$_2$²H$_3$ requires 264.1791, observed 264.1799.

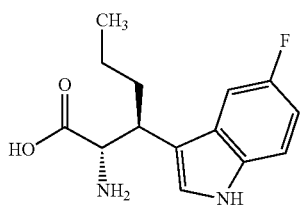 [SMILES: CCC[C@@H](c1c[nH]c2ccc(F)cc12)[C@H](N)C(=O)O]

β-Propyl-5-fluorotryptophan. $^1$H NMR (400 MHz, D$_2$O) δ 7.42 (dd, J=8.9, 4.6 Hz, 1H), 7.33 (d, J=10.4 Hz, 2H), 7.00 (td, J=9.3, 2.5 Hz, 1H), 4.21 (d, J=5.6 Hz, 1H), 3.64 (dt, J=10.8, 5.5 Hz, 1H), 2.00-1.71 (m, 2H), 1.22 (dddt, J=13.6, 11.7, 9.4, 7.0 Hz, 2H), 0.82 (t, J=7.3 Hz, 3H). $^{13}$C NMR (101 MHz, D$_2$O) δ 172.13, 158.62, 156.31, 132.91, 126.51, 126.41, 126.37, 112.85, 112.75, 110.56, 110.30, 110.18, 110.14, 103.39, 103.15, 57.28, 37.30, 33.20, 25.06, 24.68, 21.95, 21.53, 19.98, 12.83. HRMS (FAB+) (m/z) for [M+H]$^+$ C$_{14}$H$_{13}$FN$_2$O$_2$$^2$H$_3$ requires 266.1390, observed 266.1384.

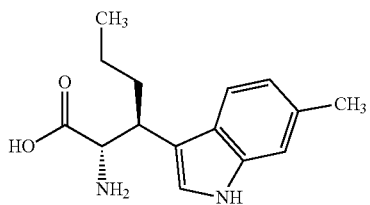 [SMILES: CCC[C@@H](c1c[nH]c2cc(C)ccc12)[C@H](N)C(=O)O]

β-Propyl-6-methyltryptophan. $^1$H NMR (400 MHz, D$_2$O) δ7.58 (d, J=8.2 Hz, 1H), 7.32 (td, J=1.4, 0.7 Hz, 1H), 7.23 (s, 1H), 7.00 (dd, J=8.3, 1.4 Hz, 1H), 4.14 (dd, J=6.2, 1.7 Hz, 1H), 3.70-3.56 (m, 1H), 2.41 (s, 3H), 1.96 (dddd, J=13.9, 10.8, 8.6, 5.6 Hz, 1H), 1.87-1.74 (m, 1H), 1.31-1.11 (m, 2H), 0.96-0.79 (m, 3H). $^{13}$C NMR (101 MHz, D$_2$O) δ172.80, 136.84, 132.46, 124.06, 123.94, 121.03, 118.53, 111.63, 110.10, 57.89, 37.63, 33.33, 20.50, 19.95, 12.78. HRMS (FAB+) (m/z) for [M+H]$^+$ C$_{15}$H$_{18}$N$_2$O$_2$$^2$H$_3$ requires 264.1791, observed 264.1800.

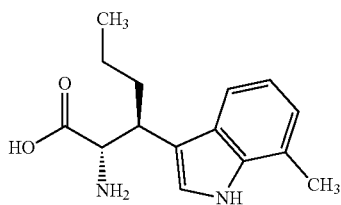 [SMILES: CCC[C@@H](c1c[nH]c2c(C)cccc12)[C@H](N)C(=O)O]

β-Propyl-7-methyltryptophan. $^1$H NMR (400 MHz, D$_2$O) δ7.54-7.45 (m, 1H), 7.31 (s, 1H), 7.09-6.99 (m, 2H), 4.20 (d, J=5.8 Hz, 1H), 3.65 (dt, J=10.8, 5.4 Hz, 1H), 2.45 (s, 3H), 1.93 (dddd, J=13.8, 10.7, 8.6, 5.6 Hz, 1H), 1.86-1.72 (m, 1H), 1.27-1.09 (m, 2H), 0.79 (t, J=7.4 Hz, 3H). $^{13}$C NMR (101 MHz, D$_2$O) δ172.18, 135.85, 125.90, 124.54, 122.43, 122.05, 119.80, 116.30, 110.47, 57.42, 37.50, 33.34, 20.00, 15.86, 12.83. HRMS (FAB+) (m/z) for [M+H]$^+$ C$_{15}$H$_{19}$N$_2$O$_2$$^2$H$_2$ requires 263.1729, observed 263.1723.

Figure 6A:
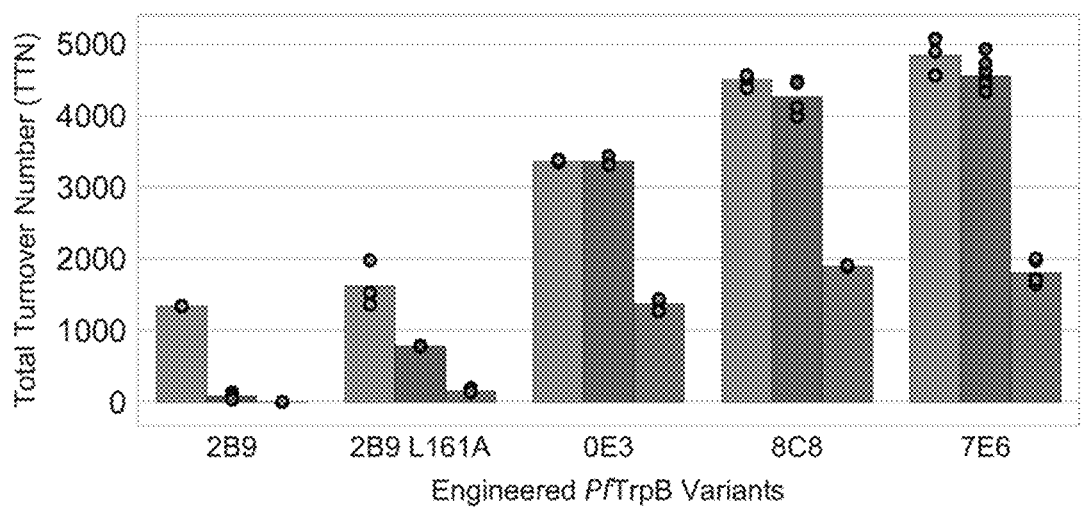
FIG. 6A shows that directed evolution of PfTrpB improves yields of β-MeTrp, β-EtTrp, and β-PrTrp simultaneously.
Figure 6B:
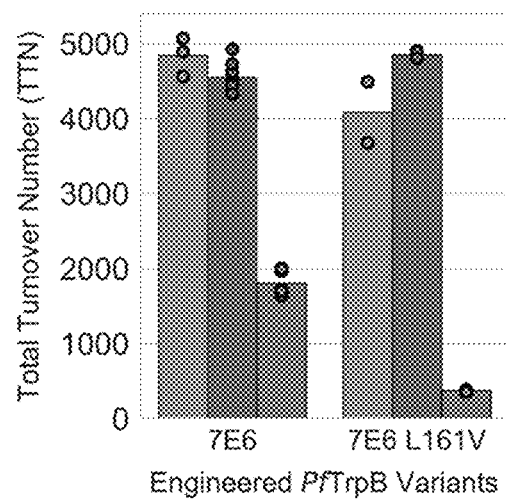
FIG. 6B shows that PfTrpB$^{7E6}$ L161V is detrimental for reactions with larger substrates, such as β-PrSer. The active site mutations L161A and L161V give comparable TTNs for reactions with Thr and β-EtSer, but TTNs are diminished 5-fold with β-PrSer.
Figure 6C:
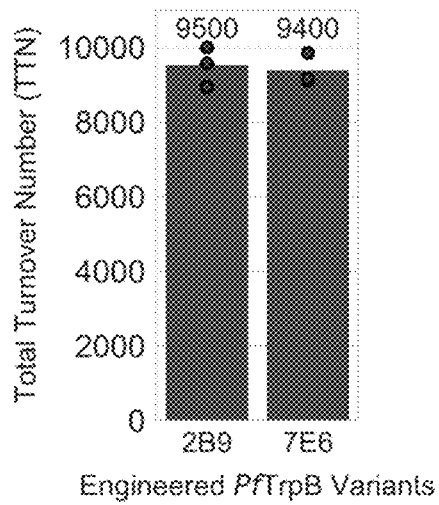
FIG. 6C shows that PfTrpB$^{7E6}$ retains activity with the native Ser substrate.

Discussion. It was hypothesized that enhanced stability of E(A-A) should confer activity with other amino acid substrates as well. Indeed, it was found that although the screen was conducted with respect to β-EtTrp synthesis, the TTN for β-MeTrp and (2S, 3S)-β-propyltryptophan (β-PrTrp) synthesis were simultaneously improved 3.6-fold and 36-fold, respectively (FIG. 6A). The earlier hypothesis that L161A would reduce steric clashes with larger substrates was also revisited by assaying PfTrpB$^{7E6}$ L161V. It was observed that whereas PfTrpB$^{7E6}$L161V is viable for synthesis of β-MeTrp and β-EtTrp, yields of β-PrTrp are reduced 5-fold (FIG. 6B). In addition to enhanced β-branched ncAA synthesis, PfTrpB$^{7E6}$ retained the robust Trp activity that is the hallmark of the wild-type enzyme (FIG. 6C).

Figure 8A:
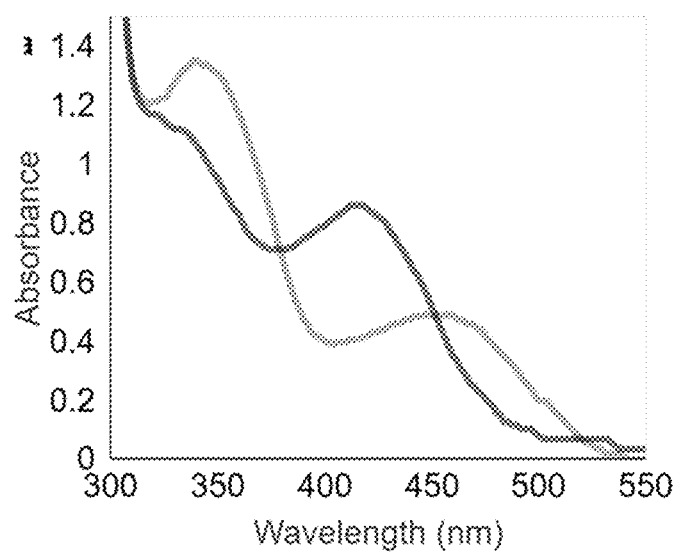
FIG. 8A shows the steady-state population of PfTrpB with substrate bound, as observed by UV-vis spectroscopy. PfTrpB$^{2B9}$ (dark grey) and PfTrpB$^{7E6}$ (light grey) are shown with Thr addition. b, β-PrSer addition. c, Engineering improves coupling efficiency with Thr, β-EtSer, and β-PrSer.
Figure 8B:
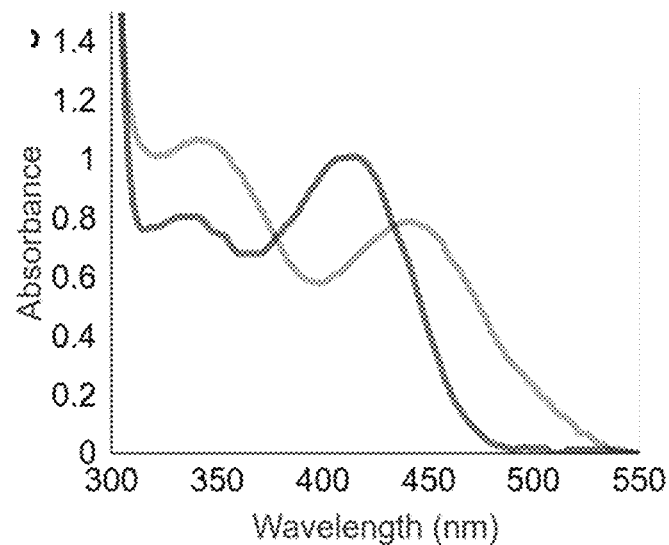
FIG. 8B shows the steady-state population of PfTrpB with substrate bound, as observed by UV-vis spectroscopy. PfTrpB$^{2B9}$ (dark grey) and PfTrpB$^{7E6}$ (light grey) are shown with β-PrSer addition.
Figure 8C:
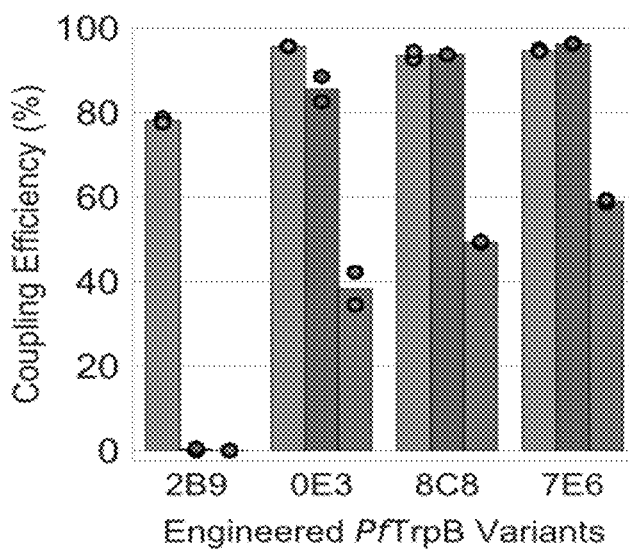
FIG. 8C shows that engineering improves coupling efficiency with Thr, β-EtSer, and β-PrSer.
Figure 9A:
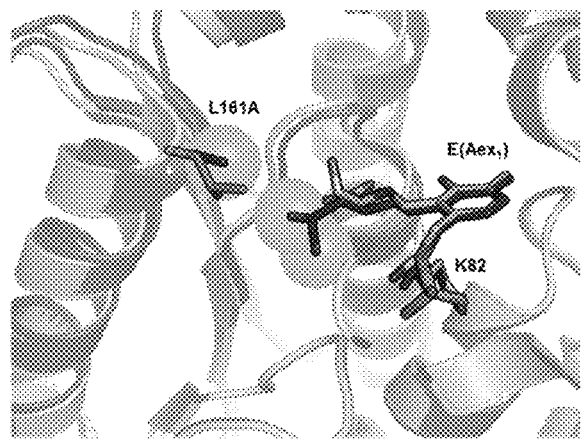
FIG. 9A shows that (2S, 3S)-β-iPrSer is bound to PfTrpB$^{7E6}$ as E(Aex$_1$) (PDB: 6CUT). The PfTrpB$^{7E6}$ COMM domain assumes a more closed conformation when compared to wild-type PfTrpB (PDB: 5DW0). L161A does not clash with the --alkyl chain of β-iPrSer.
Figure 9B:
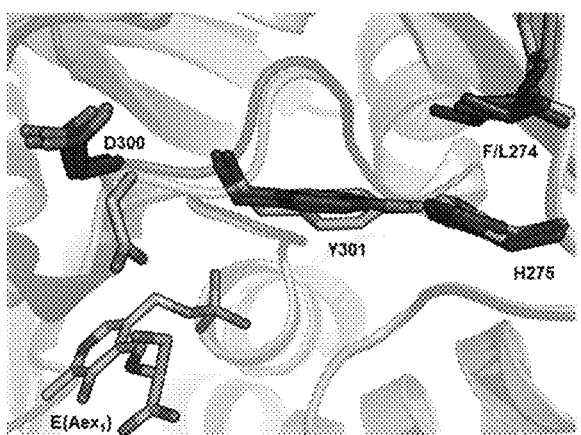
FIG. 9B shows that active site residues D300, Y301, and H275 undergo rotameric shifts associated with the closed conformation.
Figure 10A:
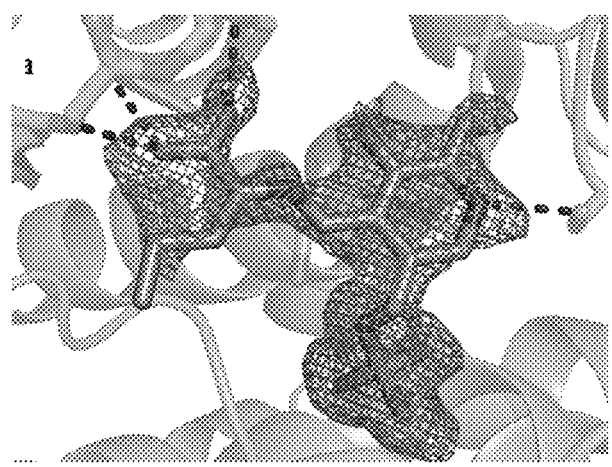
FIG. 10A shows that the structure of (2S, 3R)-β-EtSer bound to PfTrpB$^{7E6}$ as E(A-A) (PDB: 6CUZ) with $F_o$-$F_c$ map contoured at 2.0σ. The gamma carbon of the amino-acrylate is not well resolved.
Figure 10B:
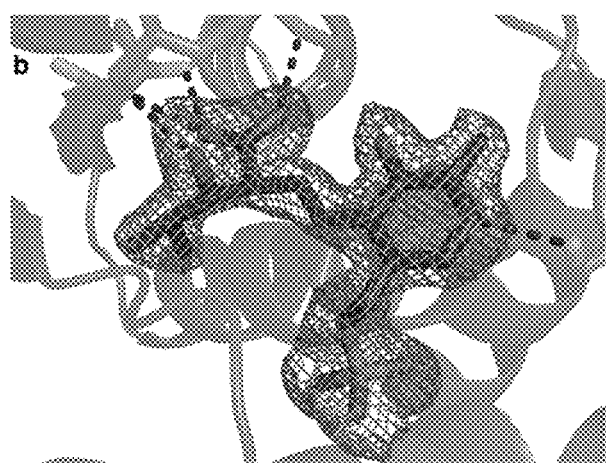
FIG. 10B shows that the structure of (2S, 3S)-β-iPrSer bound to PfTrpB$^{7E6}$ as E(Aex$_1$) (PDB: 6CUT) with $F_o$-$F_c$ map contoured at 2.5σ.

Consistent with the observations described above, directed evolution improved the enzyme's coupling efficiency and amino-acrylate persistence with all substrates (FIG. 8). The decreased yield of β-PrTrp is consistent with the less stable (2S, 3R)-β-propylserine (β-PrSer) E(A-A) species. However, reactions with (2S)-β-isopropylserine (β-iPrSer) showed only trace reactivity. To understand why catalysis did not proceed with this bulkier sidechain, β-iPrSer was soaked into PfTrpB$^{7E6}$ crystals and obtained a 1.77-Å structure (PDB: 6CUT), which shows the catalytically unreactive (2S, 3S) diastereomer of β-iPrSer bound as E(Aex$_1$) (FIG. 9). Though (2S, 3S)-β-iPrSer can form E(Aex$_1$), to dehydrate across the C$_\alpha$-C$_\beta$ bond the side chain must undergo a rotameric shift that is hindered by steric interactions with an adjacent loop. The poor activity of PfTrpB$^{7E6}$ with (2S, 3R)-β-iPrSer may reflect inhibition by an isomeric analog or may indicate increased allylic strain of the amino-acrylate that hinders productive catalysis.

Previously, PfTrpB was found to accept a broad array of indole analogs when Ser is the electrophile. It was hypothesized that PfTrpB$^{7E6}$ would retain this catalytic breadth even in the presence of unnatural amino acid substrates. Biotransformations with 11 representative nucleophiles were conducted in conjunction with β-branched substrates, yielding 27 tryptophan analogs, 20 of which are previously unreported (Table 10). Each reaction was analyzed by liquid-chromatography/mass spectrometry (LCMS), and TTN were calculated by comparing product and substrate absorption at the isosbestic wavelength (Table 1). Indole analogs were found to remain broadly tolerated and that PfTrpB$^{7E6}$ showed little steric preference with respect to the position of substituents around the indole ring. Notably, the enzyme demonstrated higher activity with fluoroindoles in conjunction with bulkier electrophiles. Activity with 5-chloroindole and Thr was also observed, a reaction that was undetectable for the parent enzyme, TrpB$^{2B9}$. In addition, undesirable N-alkylation that was previously seen in reactions with 7-azaindole and 4-fluoroindole was completely abolished. However, yields with N-nucleophilic substrates such as indazole remained low relative to their Ser counterparts.

Product identities were confirmed by $^1$H- and $^{13}$C-NMR as well as high-resolution mass spectrometry from 100-μmol preparative reactions using two equivalents of electrophilic substrate with 0.01 to 0.4 mol % catalyst loading (Table 11). Preparative reactions maintained robust activity when compared to their analytical counterparts: β-MeTrp gave 5,400 TTN (72% yield), β-EtTrp gave 5,300 TTN (88% yield), and β-PrTrp gave 1,900 TTN (77% yield).

TABLE 11

| Nucleophile \ Electrophile | Threonine (HO-CO-CH(NH₂)-CH(OH)-CH₃) | (HO-CO-CH(NH₂)-CH(OH)-CH₂CH₃) | (HO-CO-CH(NH₂)-CH(OH)-CH₂CH₂CH₃) |
|---|---|---|---|
| indole | 5400 (72%)[a] | 5300 (88%)[b] | 1900 (77%)[d] |
| 2-methylindole | 3700 (92%)[c] | 2800 (94%)[c] | 200 (21%)[g] |
| 4-methylindole | 1600 (47%)[c] | 600 (30%)[e] | 100 (23%)[h] |
| 4-fluoroindole | 2600 (87%)[c] | 1800 (89%)[e] | 200 (39%)[h] |
| 5-methylindole | 1800 (45%)[c] | 100 (20%)[h] | 20 (7%)[i] |
| 5-fluoroindole | 3200 (91%)[c] | 2900 (97%)[c] | 400 (44%)[g] |
| 5-chloroindole | 100 (20%)[h] | Not Tested | Not Tested |
| 6-methylindole | 1200 (78%)[f] | 500 (35%)[f] | 20 (10%)[i] |
| 7-methylindole | 3200 (63%)[b] | 1900 (97%)[e] | 1100 (56%)[e] |
| 7-azaindole | 3900 (77%)[b] | Not Tested | Not Tested |

TTN are reported with yields in parenthesis. Catalyst loading (%); [a]0.01%; [b]0.02%; [c]0.03%; [d]0.04%; [e]0.05%; [f]0.07%; [g]0.1%; [h]0.2%; [i]0.4%

For future applications, reaction conditions may be further optimized by tuning catalyst loading and increasing substrate equivalents (Table 12). In conjunction with the high expression levels of PfTrpB$^{7E6}$ (~300 mg enzyme per L culture), a range of β-branched ncAAs is now accessible on a preparative scale. Table 12 shows that reaction yields can be improved by increasing the equivalents of electrophilic substrate or increasing catalyst loading. LCMS reactions with PfTrpB2B9 and PfTrpB7E6 were conducted with 20 mM indole, 1 or 10 equivalents of electrophilic substrate, and varied catalyst loading (0.01%-0.1%). Reactions were incubated for 24 hours at 75° C. and analyzed by LCMS.

TABLE 12

| Enzyme | Catalyst product Loading (%) | Electrophilic Substrate | Equivalents | HPLC yield (%) |
|---|---|---|---|---|
| PfTrpB$^{2B9}$ | 0.01 | β-MeTrp | 1 | 13 |
|  | 0.01 | β-MeTrp | 10 | 24 |
| PfTrpB$^{7E6}$ | 0.01 | β-MeTrp | 1 | 48 |
|  | 0.01 | β-MeTrp | 10 | 97 |
|  | 0.05 | β-MeTrp | 1 | 95 |
|  | 0.1 | β-MeTrp | 1 | 95 |
|  | 0.01 | β-EtTrp | 1 | 46 |
|  | 0.01 | β-EtTrp | 10 | 62 |
|  | 0.05 | β-EtTrp | 1 | 91 |
|  | 0.1 | β-EtTrp | 1 | 96 |
|  | 0.01 | β-PrTrp | 1 | 18 |
|  | 0.01 | β-PrTrp | 10 | 14 |
|  | 0.05 | β-PrTrp | 1 | 52 |
|  | 0.1 | β-PrTrp | 1 | 59 |

Example 6. Preparation of Non-Canonical Tryptophan Analogs Using an Enzyme Cascade Variants TrpB$^{8C8}$ and TrpB$^{2G8}$ were assessed in a cascade reaction using glycine, aldehydes, indoles, and TmTA. Master mixes for both substrates and enzymes were made in Kpi buffer and subsequently mixed together in screw top glass 2-mL HPLC vials to a final volume of 200 μL. Standard cascade reactions were typically done with 10 mM aldehyde, 5 mM indole, 100 mM glycine, 5 μM TmTA, and 20 μM PfTrpB. Coupling reactions were typically done with 5 mM of L-β-(Me/Et/Pr/iPr)-serine, 5 mM indole, and 20 μM PfTrpB. The vials containing the reaction mixtures were incubated overnight at 75° C. The reaction mixtures were quenched to a final mixture of 50% (v/v) acetonitrile. The samples were transferred to 1.5-mL tubes and spun down (14,000 rpm, 5 min). From the supernatant, 150 μL were transferred to HPLC insert vials and screened by LC-MS.

Figure 11:
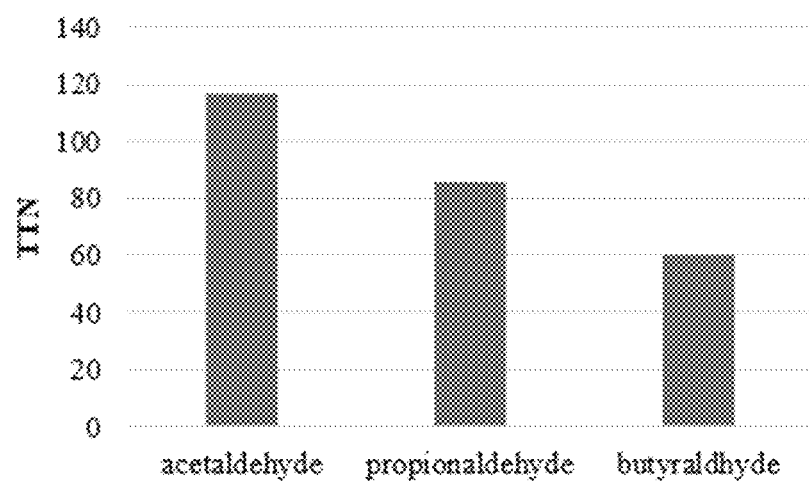
FIG. 11 shows the total turnover number for an enzymatic cascade starting with either acetaldehyde to produce β-Me-Trp, propionaldehyde to produce β-Et-Trp, or butyraldehyde to produce β-Pr-Trp. Reaction conditions: 100 mM glycine, 10 mM aldehyde, 10 mM indole, 5 μM TmTA and 10 μM TrpB$^{2G8}$ in 0.2 M kPi buffer (pH 8.0) were combined in a glass vial and left to react overnight for 24 hours at 75° C.

As shown in FIG. 11, TrpB$^{2G8}$ yielded approximately 80 TTN, which was a 2-fold improvement over TrpB$^{8C8}$. In addition, the utility of the cascade was further expanded by producing β-Me-Trp (120 TTN) and β-Pr-Trp (60 TTN) from respectively acetaldehyde or butyraldehyde in combination with indole and glycine.

Although the foregoing has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

INFORMAL SEQUENCE LISTING:

SEQ ID NO: 1 (PfTrp$^{2B9}$)
```
Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
                35                  40                  45

Arg Pro Thr Pro Leu Tyr Tyr Ala Lys Arg Leu Thr Glu Lys Ile Gly
        50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Leu Leu Ala Lys Leu Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
            115                 120                 125

Met Gly Ala Glu Asp Val Glu Arg Gln Lys Met Asn Val Phe Arg Met
130                 135                 140

Lys Leu Leu Gly Ala Asn Val Ile Pro Val Asn Ser Gly Ser Arg Thr
145                 150                 155                 160

Leu Lys Asp Ala Ile Asn Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190
```

| INFORMAL SEQUENCE LISTING: |
|---|

```
Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
        210                 215                 220

Cys Val Gly Gly Gly Ser Asn Ala Met Gly Ile Phe Tyr Pro Phe Val
225                     230                 235                 240

Asn Asp Lys Lys Val Lys Leu Val Gly Val Glu Ala Gly Gly Lys Gly
                    245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
        275                 280                 285

Ile Lys Pro Ser His Ser Ile Ala Pro Gly Leu Asp Tyr Pro Gly Val
        290                 295                 300

Gly Pro Glu His Ala Tyr Leu Lys Lys Ile Gln Arg Ala Glu Tyr Val
305                     310                 315                 320

Ala Val Thr Asp Glu Glu Ala Leu Lys Ala Phe His Glu Leu Ser Arg
                    325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Ala
        370                 375                 380

Ser Gly Asn Val
385

SEQ ID NO: 2 (PfTrpB^OE3)
Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
        50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Pro Leu Ala Lys Leu Met
            85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Met
        130                 135                 140

Lys Leu Leu Gly Ala Asn Val Ile Pro Val Asn Ser Gly Ser Arg Thr
145                 150                 155                 160

Ala Lys Asp Ala Ile Asn Glu Ala Leu Arg Asp Trp Val Ala Thr Phe
            165                 170                 175

Glu Tyr Thr His Tyr Leu Ile Gly Ser Val Val Gly Pro His Pro Tyr
        180                 185                 190
```

INFORMAL SEQUENCE LISTING:

Pro Thr Ile Val Arg Asp Phe Gln Ser Val Ile Gly Arg Glu Ala Lys
            195                 200                 205

Ala Gln Ile Leu Glu Ala Glu Gly Gln Leu Pro Asp Val Ile Val Ala
        210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
        275                 280                 285

Ile Lys Pro Ser His Ser Ile Ala Pro Gly Leu Asp Tyr Pro Gly Val
        290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
            325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
            355                 360                 365

Asn Leu Ser Gly Arg Gly Asp Lys Asp Leu Asp Ile Val Leu Lys Ala
        370                 375                 380

Ser Gly Asn Val
385

SEQ ID NO: 3 (PfTrpB$^{8C8}$)
Met Trp Phe Gly Gly Phe Gly Gly Gln Tyr Val Pro Glu Thr Leu Val
1                   5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
            35                  40                  45

Arg Pro Thr Pro Leu Tyr Tyr Ala Lys Arg Leu Thr Glu Lys Ile Gly
        50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Pro Leu Ala Lys Leu Met
            85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
            115                 120                 125

Met Gly Ala Glu Asp Val Glu Arg Gln Lys Met Asn Val Phe Arg Met
            130                 135                 140

Lys Leu Leu Gly Ala Asn Val Ile Pro Val Asn Ser Gly Ser Arg Thr
145                 150                 155                 160

Ala Lys Asp Ala Ile Asn Glu Ala Leu Arg Asp Trp Glu Ala Thr Phe
            165                 170                 175

Glu Tyr Thr His Tyr Leu Ile Gly Ser Val Val Gly Pro His Pro Tyr
            180                 185                 190

-continued

INFORMAL SEQUENCE LISTING:

Pro Thr Ile Val Arg Asp Phe Gln Ser Val Ile Gly Arg Glu Ala Lys
            195                 200                 205

Ala Gln Ile Leu Glu Ala Glu Gly Gln Leu Pro Asp Val Ile Val Ala
            210                 215                 220

Cys Val Gly Gly Gly Ser Asn Ala Met Gly Ile Phe Tyr Pro Phe Val
225                     230                 235                 240

Asn Asp Lys Lys Val Lys Leu Val Gly Val Glu Ala Gly Gly Lys Gly
                    245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
            275                 280                 285

Ile Lys Pro Ser His Ser Ile Ala Pro Gly Leu Asp Tyr Pro Gly Val
            290                 295                 300

Gly Pro Glu His Ala Tyr Leu Lys Lys Ile Gln Arg Ala Glu Tyr Val
305                     310                 315                 320

Ala Val Thr Asp Glu Glu Ala Leu Lys Ala Phe His Glu Leu Ser Arg
            325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
            355                 360                 365

Asn Leu Ser Gly Arg Gly Asp Lys Asp Leu Asp Ile Val Leu Lys Ala
            370                 375                 380

Ser Gly Asn Val
385

SEQ ID NO: 4 (PfTrpB$^{7E6}$)
Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
            35                  40                  45

Arg Pro Thr Pro Leu Tyr Tyr Ala Lys Arg Leu Thr Glu Lys Ile Gly
            50                  55                  60

Gly Ala Lys Ile Tyr Leu Lys Arg Glu Asp Leu Val His Gly Gly Ala
65                      70                  75                  80

His Lys Thr Asn Asn Ala Ile Gly Gln Ala Pro Leu Ala Lys Leu Met
                    85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
            115                 120                 125

Met Gly Ala Glu Asp Val Glu Arg Gln Lys Met Asn Val Phe Arg Met
            130                 135                 140

Lys Leu Leu Gly Ala Asn Val Ile Pro Val Asn Ser Gly Ser Arg Thr
145                 150                 155                 160

Ala Lys Asp Ala Ile Asn Glu Ala Leu Arg Asp Trp Glu Ala Thr Phe
            165                 170                 175

Glu Tyr Thr His Tyr Leu Ile Gly Ser Val Val Gly Pro His Pro Tyr
            180                 185                 190

INFORMAL SEQUENCE LISTING:

Pro Thr Ile Val Arg Asp Phe Gln Ser Val Ile Gly Arg Glu Ala Lys
            195                 200                 205

Ala Gln Ile Leu Glu Ala Glu Gly Gln Leu Pro Asp Val Ile Val Ala
            210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
            245                 250                 255

Leu Glu Ser Gly Lys His Ser Ala Ser Leu Asn Ala Gly Gln Val Gly
            260                 265                 270

Val Leu His Gly Met Leu Ser Tyr Phe Leu Gln Asp Glu Glu Gly Gln
            275                 280                 285

Ile Lys Pro Ser His Ser Ile Ala Pro Gly Leu Asp Tyr Pro Gly Val
            290                 295                 300

Gly Pro Glu His Ala Tyr Leu Lys Lys Ile Gln Arg Ala Glu Tyr Val
305                 310                 315                 320

Thr Val Thr Asp Glu Glu Ala Leu Lys Ala Phe His Glu Leu Ser Arg
            325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
            355                 360                 365

Asn Leu Ser Gly Arg Gly Asp Lys Asp Leu Asp Ile Val Leu Lys Ala
            370                 375                 380

Ser Gly Asn Val
385

SEQ ID NO: 5 (PfTrpB$^{2G8}$)
Met Trp Phe Gly Gly Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
            35                  40                  45

Arg Pro Thr Pro Leu Tyr Tyr Ala Lys Arg Leu Thr Glu Lys Ile Gly
            50                  55                  60

Gly Ala Lys Ile Tyr Leu Lys Arg Glu Asp Leu Val His Gly Gly Ala
65                  70                  75                  80

His Lys Thr Asn Asn Ala Ile Gly Gln Ala Leu Leu Ala Lys Leu Met
            85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
            115                 120                 125

Met Gly Ala Glu Asp Val Glu Arg Gln Lys Leu Asn Val Phe Arg Met
            130                 135                 140

Lys Leu Leu Gly Ala Asn Val Ile Pro Val Asn Ser Gly Ser Arg Thr
145                 150                 155                 160

Ala Lys Asp Ala Ile Asp Glu Ala Leu Arg Asp Trp Glu Ala Thr Phe
            165                 170                 175

Glu Tyr Thr His Tyr Leu Ile Gly Ser Val Val Gly Pro His Pro Tyr
            180                 185                 190

-continued

INFORMAL SEQUENCE LISTING:

Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
        210                 215                 220

Cys Val Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
                260                 265                 270

Val Leu His Gly Met Leu Ser Tyr Phe Leu Gln Asp Glu Glu Gly Gln
        275                 280                 285

Ile Lys Pro Ser His Ser Ile Ala Pro Gly Leu Asp Tyr Pro Gly Val
        290                 295                 300

Gly Pro Glu His Ala Tyr Leu Lys Lys Ile Gln Arg Ala Glu Tyr Val
305                 310                 315                 320

Thr Val Thr Asp Glu Glu Ala Leu Lys Ala Phe His Glu Leu Asn Arg
                325                 330                 335

Thr Glu Gly Ile Ile Pro Ala Leu Glu Ser Ala His Ala Val Ala Tyr
                340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Ala
        370                 375                 380

Ser Gly Asn Val
385

SEQ ID NO: 6 (TmTA)
Met Ile Asp Leu Arg Ser Asp Thr Val Thr Lys Pro Thr Glu Glu Met
1               5                   10                  15

Arg Lys Ala Met Ala Gln Ala Glu Val Gly Asp Asp Val Tyr Gly Glu
                20                  25                  30

Asp Pro Thr Ile Asn Glu Leu Glu Arg Leu Ala Ala glu Thr Phe Gly
                35                  40                  45

Lys Glu Ala Ala Leu Phe Val Pro Ser Gly Thr Met Gly Asn Gln Val
        50                  55                  60

Ser Ile Met Ala His Thr Gln Arg Gly Asp Glu Val Ile Leu Glu Ala
65                  70                  75                  80

Asp Ser His Ile Phe Trp Tyr Glu Val Gly Ala Met Ala Val Leu Ser
                85                  90                  95

Gly Val Met Pro His Pro Val Pro Gly Lys Asn Gly Ala Met Asp Pro
                100                 105                 110

Asp Asp Val Arg Lys Ala Ile Arg Pro Arg Asn Ile His Phe Pro Arg
        115                 120                 125

Thr Ser Leu Ile Ala Ile Glu Asn Thr His Asn Arg Ser Gly Gly Arg
        130                 135                 140

Val Val Pro Leu Glu Asn Ile Lys Glu Ile Cys Thr Ile Ala Lys Glu
145                 150                 155                 160

His Gly Ile Asn Val His Ile Asp Gly Ala Arg Ile Phe Asn Ala Ser
                165                 170                 175

Ile Ala Ser Gly Val Pro Val Lys Glu Tyr Ala Gly Tyr Ala Asp Ser
                180                 185                 190

-continued

INFORMAL SEQUENCE LISTING:

```
Val Met Phe Cys Leu Ser Lys Gly Leu Cys Ala Pro Val Gly Ser Val
        195                 200                 205

Val Val Gly Asp Arg Asp Phe Ile Glu Arg Ala Arg Lys Ala Arg Lys
        210                 215                 220

Met Leu Gly Gly Gly Met Arg Gln Ala Gly Val Leu Ala Ala Ala Gly
225                 230                 235                 240

Ile Ile Ala Leu Thr Lys Met Val Asp Arg Leu Lys Glu Asp His Glu
                245                 250                 255

Asn Ala Arg Phe Leu Ala Leu Lys Leu Lys Glu Ile Gly Tyr Ser Val
                260                 265                 270

Asn Pro Glu Asp Val Lys Thr Asn Met Val Ile Leu Arg Thr Asp Asn
                275                 280                 285

Leu Lys Val Asn Ala His Gly Phe Ile Glu Ala Leu Arg Asn Ser Gly
                290                 295                 300

Val Leu Ala Asn Ala Val Ser Asp Thr Glu Ile Arg Leu Val Thr His
305                 310                 315                 320

Lys Asp Val Ser Arg Asn Asp Ile Glu Glu Ala Leu Asn Ile Phe Glu
                325                 330                 335

Lys Leu Phe Arg Lys Phe Ser
                340

SEQ ID NO: 7 (TmTrpB)
Met Lys Gly Tyr Phe Gly Pro Tyr Gly Gly Gln Tyr Val Pro Glu Ile
1               5                   10                  15

Leu Met Pro Ala Leu Glu Glu Leu Glu Ala Ala Tyr Glu Glu Ile Met
                20                  25                  30

Lys Asp Glu Ser Phe Trp Lys Glu Phe Asn Asp Leu Leu Arg Asp Tyr
                35                  40                  45

Ala Gly Arg Pro Thr Pro Leu Tyr Phe Ala Arg Arg Leu Ser Glu Lys
                50                  55                  60

Tyr Gly Ala Arg Ile Tyr Leu Lys Arg Glu Asp Leu Leu His Thr Gly
65                  70                  75                  80

Ala His Lys Ile Asn Asn Ala Ile Gly Gln Val Leu Leu Ala Lys Lys
                85                  90                  95

Met Gly Lys Thr Arg Ile Ile Ala Glu Thr Gly Ala Gly Gln His Gly
                100                 105                 110

Val Ala Thr Ala Thr Ala Ala Ala Leu Phe Gly Met Glu Cys Val Ile
                115                 120                 125

Tyr Met Gly Glu Glu Asp Thr Ile Arg Gln Lys Pro Asn Val Glu Arg
130                 135                 140

Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
                165                 170                 175

Leu Gln Thr Thr Tyr Tyr Val Ile Gly Ser Val Val Gly Pro His Pro
                180                 185                 190

Tyr Pro Ile Ile Val Arg Asn Phe Gln Lys Val Ile Gly Glu Glu Thr
                195                 200                 205

Lys Lys Gln Ile Leu Glu Lys Glu Gly Arg Leu Pro Asp Tyr Ile Val
                210                 215                 220

Ala Cys Val Gly Gly Gly Ser Asn Ala Ala Gly Ile Phe Tyr Pro Phe
225                 230                 235                 240
```

-continued

INFORMAL SEQUENCE LISTING:

Ile Asp Ser Gly Val Lys Leu Ile Gly Val Glu Ala Gly Gly Glu Gly
            245                 250                 255

Leu Glu Thr Gly Lys His Ala Ala Ser Leu Leu Lys Gly Lys Ile Gly
        260                 265                 270

Tyr Leu His Gly Ser Lys Thr Phe Val Leu Gln Asp Asp Trp Gly Gln
            275                 280                 285

Val Gln Val Thr His Ser Val Ser Ala Gly Leu Asp Tyr Ser Gly Val
        290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
            325                 330                 335

Leu Glu Gly Ile Ile Pro Ala Leu Glu Ser Ser His Ala Leu Ala Tyr
            340                 345                 350

Leu Lys Lys Ile Asn Ile Lys Gly Lys Val Val Val Asn Leu Ser
            355                 360                 365

Gly Arg Gly Asp Lys Asp Leu Glu Ser Val Leu Asn His Pro Tyr Val
        370                 375                 380

Arg Glu Arg Ile Arg
385

SEQ ID NO: 8 (A. flugidus TrpB)
Met Arg Cys Trp Leu Glu Asn Leu Ser Gly Gly Arg Lys Met Lys Phe
1               5                   10                  15

Gly Glu Phe Gly Gly Arg Phe Val Pro Glu Val Leu Ile Pro Pro Leu
            20                  25                  30

Glu Glu Leu Glu Lys Ala Tyr Asp Arg Phe Lys Asp Asp Glu Glu Phe
        35                  40                  45

Lys Ala Arg Leu Glu Tyr Tyr Leu Lys Ser Tyr Ala Gly Arg Pro Thr
    50                  55                  60

Pro Leu Tyr Phe Ala Glu Asn Leu Ser Arg Glu Leu Gly Val Lys Ile
65                  70                  75                  80

Tyr Leu Lys Arg Glu Asp Leu Leu His Gly Gly Ala His Lys Ile Asn
            85                  90                  95

Asn Thr Ile Gly Gln Ala Leu Leu Ala Lys Phe Met Gly Lys Lys Arg
            100                 105                 110

Val Ile Ala Glu Thr Gly Ala Gly Gln His Gly Val Ala Thr Ala Met
        115                 120                 125

Ala Ala Ala Leu Leu Gly Leu Glu Ala Glu Ile Tyr Met Gly Ala Glu
    130                 135                 140

Asp Tyr Glu Arg Gln Lys Met Asn Val Phe Arg Met Glu Leu Leu Gly
145                 150                 155                 160

Ala Lys Val Thr Ala Val Glu Ser Gly Ser Arg Thr Leu Lys Asp Ala
            165                 170                 175

Ile Asn Glu Ala Leu Arg Asp Trp Val Glu Ser Phe Glu His Thr His
            180                 185                 190

Tyr Leu Ile Gly Ser Val Val Gly Pro His Pro Phe Pro Thr Ile Val
        195                 200                 205

Arg Asp Phe Gln Ala Val Ile Gly Lys Glu Ala Arg Arg Gln Ile Ile
    210                 215                 220

Glu Ala Glu Gly Gly Met Pro Asp Ala Ile Ile Ala Cys Val Gly Gly
225                 230                 235                 240

-continued

INFORMAL SEQUENCE LISTING:

Gly Ser Asn Ala Met Gly Ile Phe His Pro Phe Leu Asn Asp Asp Val
                245                 250                 255

Arg Leu Ile Gly Val Glu Ala Gly Gly Glu Gly Ile Glu Ser Gly Arg
                260                 265                 270

His Ser Ala Ser Leu Thr Ala Gly Ser Lys Gly Val Leu His Gly Met
                275                 280                 285

Leu Ser Tyr Phe Leu Gln Asp Glu Glu Gly Met Met Leu Asp Thr His
                290                 295                 300

Ser Val Ser Ala Gly Leu Asp Tyr Pro Gly Val Gly Pro Glu His Ala
305                 310                 315                 320

Tyr Leu Lys Glu Thr Gly Arg Cys Glu Tyr Val Thr Val Asn Asp Glu
                325                 330                 335

Glu Ala Leu Arg Ala Phe Lys Thr Leu Ser Lys Leu Glu Gly Ile Ile
                340                 345                 350

Pro Ala Leu Glu Ser Ala His Ala Ile Ala Tyr Ala Met Lys Met Ala
                355                 360                 365

Glu Glu Met Gln Arg Asp Asp Val Leu Val Val Asn Leu Ser Gly Arg
                370                 375                 380

Gly Asp Lys Asp Met Asp Ile Val Arg Arg Leu Ala
385                 390                 395

SEQ ID NO: 9 (E.coli TrpB)
Met Thr Thr Leu Leu Asn Pro Tyr Phe Gly Glu Phe Gly Gly Met Tyr
1               5                   10                  15

Val Pro Gln Ile Leu Met Pro Ala Leu Arg Gln Leu Glu Glu Ala Phe
                20                  25                  30

Val Ser Ala Gln Lys Asp Pro Glu Phe Gln Ala Gln Phe Asn Asp Leu
                35                  40                  45

Leu Lys Asn Tyr Ala Gly Arg Pro Thr Ala Leu Thr Lys Cys Gln Asn
                50                  55                  60

Ile Thr Ala Gly Thr Asn Thr Thr Leu Tyr Leu Lys Arg Glu Asp Leu
65                  70                  75                  80

Leu His Gly Gly Ala His Lys Thr Asn Gln Val Leu Gly Gln Ala Leu
                85                  90                  95

Leu Ala Lys Arg Met Gly Lys Thr Glu Ile Ile Ala Glu Thr Gly Ala
                100                 105                 110

Gly Gln His Gly Val Ala Ser Ala Leu Ala Ser Ala Leu Leu Gly Leu
                115                 120                 125

Lys Cys Arg Ile Tyr Met Gly Ala Lys Asp Val Glu Arg Gln Ser Pro
                130                 135                 140

Asn Val Phe Arg Met Arg Leu Met Gly Ala Glu Val Ile Pro Val His
145                 150                 155                 160

Ser Gly Ser Ala Thr Leu Lys Asp Ala Cys Asn Glu Ala Leu Arg Asp
                165                 170                 175

Trp Ser Gly Ser Tyr Glu Thr Ala His Tyr Met Leu Gly Thr Ala Ala
                180                 185                 190

Gly Pro His Pro Tyr Pro Thr Ile Val Arg Glu Phe Gln Arg Met Ile
                195                 200                 205

Gly Glu Glu Thr Lys Ala Gln Ile Leu Glu Arg Glu Gly Arg Leu Pro
                210                 215                 220

Asp Ala Val Ile Ala Cys Val Gly Gly Gly Ser Asn Ala Ile Gly Met
225                 230                 235                 240

-continued

INFORMAL SEQUENCE LISTING:

Phe Ala Asp Phe Ile Asn Glu Thr Asn Val Gly Leu Ile Gly Val Glu
            245                 250                 255

Pro Gly Gly His Gly Ile Glu Thr Gly Glu His Gly Ala Pro Leu Lys
            260                 265                 270

His Gly Arg Val Gly Ile Tyr Phe Gly Met Lys Ala Pro Met Met Gln
            275                 280                 285

Thr Glu Asp Gly Gln Ile Glu Glu Ser Tyr Ser Ile Ser Ala Gly Leu
            290                 295                 300

Asp Phe Pro Ser Val Gly Pro Gln His Ala Tyr Leu Asn Ser Thr Gly
305                 310                 315                 320

Arg Ala Asp Tyr Val Ser Ile Thr Asp Asp Glu Ala Leu Glu Ala Phe
            325                 330                 335

Lys Thr Leu Cys Leu His Glu Gly Ile Ile Pro Ala Leu Glu Ser Ser
            340                 345                 350

His Ala Leu Ala His Ala Leu Lys Met Met Arg Glu Asn Pro Asp Lys
            355                 360                 365

Glu Gln Leu Leu Val Val Asn Leu Ser Gly Arg Gly Asp Lys Asp Ile
            370                 375                 380

Phe Thr Val His Asp Ile Leu Lys Ala Arg Gly Glu Ile
385                 390                 395

What is claimed is:

1. A method for preparing a β-substituted amino acid according to Formula I:

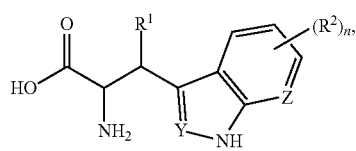

the method comprising:
combining i) an unsubstituted indole or a substituted indole, ii) a β-substituted serine, and iii) a tryptophan synthase β-subunit comprising a polypeptide having tryptophan synthase activity and having:
at least 85% identity to the amino acid sequence set forth in SEQ ID NO:1, amino acid mutations at residues corresponding to positions 91, 161, and 274 of SEQ ID NO:1, and
optionally at least one amino acid mutation at residues corresponding to positions selected from the group consisting of 68, 139, 166, 173, and 335 of SEQ ID NO:1; and
maintaining the resulting mixture under conditions sufficient to form the β-substituted amino acid according to Formula I;
wherein:
$R^1$ is $C_{2-8}$ alkyl, which is optionally substituted with one or more $R^{1a}$;
each $R^{1a}$ is independently selected from the group consisting of halogen, —OH, —CN, —N$_3$, —NO$_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N(R$^{1b}$)$_2$, —B(OR$^{1b}$)$_2$, —C(O)R$^{1c}$, —C(O)N(R$^{1b}$)$_2$, —NR$^{1b}$C(O)R$^{1c}$ and —OC(O)R$^{1c}$;
each $R^{1b}$ is independently selected from the group consisting of H and $C_{1-6}$ alkyl;
each $R^{1c}$ is independently selected from the group consisting of H, —OH, halogen, $C_{1-6}$ alkyl, $C_{1-6}$ alkoxy;

Y and Z are independently selected from the group consisting of CH, CR², and N;

each R² is independently selected from the group consisting of halogen, —OH, —CN, —N₃, —NO₂, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N(R²ᵃ)₂, —B(OR²ᵃ)₂, —C(O)R²ᵇ, —C(O)N(R²ᵃ)₂, —NR²ᵃC(O)R²ᵇ, and —OC(O)R²ᵇ;

each R²ᵃ is independently selected from the group consisting of H and $C_{1-6}$ alkyl;

each R²ᵇ is independently selected from the group consisting of H, —OH, halogen, $C_{1-6}$ alkyl, $C_{1-6}$ alkoxy; and subscript n is 0, 1, 2, or 3.

2. The method of claim 1, wherein the amino acid mutation at the residue corresponding to position 91 in SEQ ID NO:1 is a mutation to a proline residue.

3. The method of claim 2, wherein the amino acid mutation at the residue corresponding to position 161 in SEQ ID NO:1 is a mutation to an alanine residue or a valine residue.

4. The method of claim 1, wherein the tryptophan synthase β-subunit comprises the amino acid sequence set forth in any one of SEQ ID NOS:2-4.

5. The method of claim 4, wherein the tryptophan synthase β-subunit comprises the amino acid sequence set forth in SEQ ID NO:4.

6. The method of claim 1, wherein R¹ is selected from the group consisting of ethyl and n-propyl.

7. The method of claim 1, wherein Y is selected from the group consisting of CH and N.

8. The method of claim 1, wherein subscript n is 0 or 1.

9. The method of claim 1, wherein R² is selected from the group consisting of halogen and $C_{1-6}$ alkyl.

10. The method of claim 1, wherein the β-substituted serine is prepared by combining a) glycine, b) an aldehyde, and c) an aldolase or variant thereof under conditions sufficient to form the β-substituted serine.

11. The method of claim 1, further comprising protecting the β-substituted amino acid according to Formula I.

12. A tryptophan synthase β-subunit comprising a polypeptide having tryptophan synthase activity and having:
at least 85% identity to the amino acid sequence set forth in SEQ ID NO:1,
amino acid mutations at residues corresponding to positions 91, 161, and 274 of SEQ ID NO:1, and
optionally at least one amino acid mutation at residues corresponding to positions selected from the group consisting of 68, 139, 166, 173, and 335 of SEQ ID NO:1.

13. The tryptophan synthase β-subunit of claim 12, wherein the amino acid mutation at the residue corresponding to position 161 of SEQ ID NO:1 is selected from the group consisting of an L161A mutation and an L161V mutation.

14. The tryptophan synthase β-subunit of claim 12, comprising an alanine residue at position 161 of SEQ ID NO:1.

15. The tryptophan synthase β-subunit of claim 14, further comprising a mutation at a residue corresponding to position 321 of SEQ ID NO:1.

16. The tryptophan synthase β-subunit of claim 14, which comprises the amino acid sequence set forth in any one of SEQ ID NOS:2-4.

17. The tryptophan synthase β-subunit of claim 12, consisting of the amino acid sequence set forth in SEQ ID NO:2.

18. The tryptophan synthase β-subunit of claim 12, consisting of the amino acid sequence set forth in SEQ ID NO:3.

19. The tryptophan synthase β-subunit of claim 12, consisting of the amino acid sequence set forth in SEQ ID NO:4.

* * * * *

SEQUENCE LISTING

<160> NUMBER OF SEQ ID NOS: 37

<210> SEQ ID NO 1
<211> LENGTH: 388
<212> TYPE: PRT
<213> ORGANISM: Artificial Sequence
<220> FEATURE:
<223> OTHER INFORMATION: Synthetic Construct

<400> SEQUENCE: 1

Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
            35                  40                  45

Arg Pro Thr Pro Leu Tyr Tyr Ala Lys Arg Leu Thr Glu Lys Ile Gly
        50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Leu Leu Ala Lys Leu Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Met
    130                 135                 140

Lys Leu Leu Gly Ala Asn Val Ile Pro Val Asn Ser Gly Ser Arg Thr
145                 150                 155                 160

Leu Lys Asp Ala Ile Asn Glu Ala Leu Arg Asp Trp Val Ala Thr Phe
                165                 170                 175
Glu Tyr Thr His Tyr Leu Ile Gly Ser Val Val Gly Pro His Pro Tyr
            180                 185                 190
Pro Thr Ile Val Arg Asp Phe Gln Ser Val Ile Gly Arg Glu Ala Lys
        195                 200                 205
Ala Gln Ile Leu Glu Ala Glu Gly Gln Leu Pro Asp Val Ile Val Ala
    210                 215                 220
Cys Val Gly Gly Ser Asn Ala Met Gly Ile Phe Tyr Pro Phe Val
225                 230                 235                 240
Asn Asp Lys Lys Val Lys Leu Val Gly Val Glu Ala Gly Gly Lys Gly
                245                 250                 255
Leu Glu Ser Gly Lys His Ser Ala Ser Leu Asn Ala Gly Gln Val Gly
            260                 265                 270
Val Ser His Gly Met Leu Ser Tyr Phe Leu Gln Asp Glu Gly Gln
        275                 280                 285
Ile Lys Pro Ser His Ser Ile Ala Pro Gly Leu Asp Tyr Pro Gly Val
    290                 295                 300
Gly Pro Glu His Ala Tyr Leu Lys Lys Ile Gln Arg Ala Glu Tyr Val
305                 310                 315                 320
Ala Val Thr Asp Glu Glu Ala Leu Lys Ala Phe His Glu Leu Ser Arg
                325                 330                 335
Thr Glu Gly Ile Ile Pro Ala Leu Glu Ser Ala His Ala Val Ala Tyr
            340                 345                 350
Ala Met Lys Leu Ala Lys Glu Met Ser Arg Asp Glu Ile Ile Ile Val
        355                 360                 365
Asn Leu Ser Gly Arg Gly Asp Lys Asp Leu Asp Ile Val Leu Lys Ala
    370                 375                 380
Ser Gly Asn Val
385

<210> SEQ ID NO 2
<211> LENGTH: 388
<212> TYPE: PRT
<213> ORGANISM: Artificial Sequence
<220> FEATURE:
<223> OTHER INFORMATION: Synthetic Construct

<400> SEQUENCE: 2

Met Trp Phe Gly Glu Phe Gly Gly Gln Tyr Val Pro Glu Thr Leu Val
1               5                   10                  15
Gly Pro Leu Lys Glu Leu Glu Lys Ala Tyr Lys Arg Phe Lys Asp Asp
                20                  25                  30
Glu Glu Phe Asn Arg Gln Leu Asn Tyr Tyr Leu Lys Thr Trp Ala Gly
            35                  40                  45
Arg Pro Thr Pro Leu Tyr Tyr Ala Lys Arg Leu Thr Glu Lys Ile Gly
        50                  55                  60
Gly Ala Lys Val Tyr Leu Lys Arg Glu Asp Leu Val His Gly Gly Ala
65                  70                  75                  80
His Lys Thr Asn Asn Ala Ile Gly Gln Ala Pro Leu Ala Lys Leu Met
                85                  90                  95
Gly Lys Thr Arg Leu Ile Ala Glu Thr Gly Ala Gly Gln His Gly Val
            100                 105                 110
Ala Thr Ala Met Ala Gly Ala Leu Leu Gly Met Lys Val Asp Ile Tyr
        115                 120                 125

```
Met Gly Ala Glu Asp Val Glu Arg Gln Lys Met Asn Val Phe Arg Met
130                 135                 140

Lys Leu Leu Gly Ala Asn Val Ile Pro Val Asn Ser Gly Ser Arg Thr
145                 150                 155                 160

Ala Lys Asp Ala Ile Asn Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
        275                 280                 285

Ile Lys Pro Ser His Ser Ile Ala Pro Gly Leu Asp Tyr Pro Gly Val
290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Ala
370                 375                 380

Ser Gly Asn Val
385

<210> SEQ ID NO 3
<211> LENGTH: 388
<212> TYPE: PRT
<213> ORGANISM: Artificial Sequence
<220> FEATURE:
<223> OTHER INFORMATION: Synthetic Construct

<400> SEQUENCE: 3

Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
    50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Pro Leu Ala Lys Leu Met
                85                  90                  95
```

```
Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Met
130                 135                 140

Lys Leu Leu Gly Ala Asn Val Ile Pro Val Asn Ser Gly Ser Arg Thr
145                 150                 155                 160

Ala Lys Asp Ala Ile Asn Glu Ala Leu Arg Asp Trp Glu Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
        275                 280                 285

Ile Lys Pro Ser His Ser Ile Ala Pro Gly Leu Asp Tyr Pro Gly Val
290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Ala
370                 375                 380

Ser Gly Asn Val
385

<210> SEQ ID NO 4
<211> LENGTH: 388
<212> TYPE: PRT
<213> ORGANISM: Artificial Sequence
<220> FEATURE:
<223> OTHER INFORMATION: Synthetic Construct

<400> SEQUENCE: 4

Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
50                  55                  60
```

Gly Ala Lys Ile Tyr Leu Lys Arg Glu Asp Leu Val His Gly Gly Ala
65                  70                  75                  80

His Lys Thr Asn Asn Ala Ile Gly Gln Ala Pro Leu Ala Lys Leu Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Met
    130                 135                 140

Lys Leu Leu Gly Ala Asn Val Ile Pro Val Asn Ser Gly Ser Arg Thr
145                 150                 155                 160

Ala Lys Asp Ala Ile Asn Glu Ala Leu Arg Asp Trp Glu Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
    210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Leu His Gly Met Leu Ser Tyr Phe Leu Gln Asp Glu Glu Gly Gln
        275                 280                 285

Ile Lys Pro Ser His Ser Ile Ala Pro Gly Leu Asp Tyr Pro Gly Val
    290                 295                 300

Gly Pro Glu His Ala Tyr Leu Lys Lys Ile Gln Arg Ala Glu Tyr Val
305                 310                 315                 320

Thr Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Ala
    370                 375                 380

Ser Gly Asn Val
385

<210> SEQ ID NO 5
<211> LENGTH: 388
<212> TYPE: PRT
<213> ORGANISM: Artificial Sequence
<220> FEATURE:
<223> OTHER INFORMATION: Synthetic Construct

<400> SEQUENCE: 5

Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

```
Glu Glu Phe Asn Arg Gln Leu Asn Tyr Tyr Leu Lys Thr Trp Ala Gly
             35                  40                  45

Arg Pro Thr Pro Leu Tyr Tyr Ala Lys Arg Leu Thr Glu Lys Ile Gly
 50                  55                  60

Gly Ala Lys Ile Tyr Leu Lys Arg Glu Asp Leu Val His Gly Gly Ala
 65                  70                  75                  80

His Lys Thr Asn Asn Ala Ile Gly Gln Ala Leu Leu Ala Lys Leu Met
                 85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
            115                 120                 125

Met Gly Ala Glu Asp Val Glu Arg Gln Lys Leu Asn Val Phe Arg Met
130                 135                 140

Lys Leu Leu Gly Ala Asn Val Ile Pro Val Asn Ser Gly Ser Arg Thr
145                 150                 155                 160

Ala Lys Asp Ala Ile Asp Glu Ala Leu Arg Asp Trp Glu Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
            195                 200                 205

Ala Gln Ile Leu Glu Ala Glu Gly Gln Leu Pro Asp Val Ile Val Ala
            210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Leu His Gly Met Leu Ser Tyr Phe Leu Gln Asp Glu Glu Gly Gln
            275                 280                 285

Ile Lys Pro Ser His Ser Ile Ala Pro Gly Leu Asp Tyr Pro Gly Val
            290                 295                 300

Gly Pro Glu His Ala Tyr Leu Lys Lys Ile Gln Arg Ala Glu Tyr Val
305                 310                 315                 320

Thr Val Thr Asp Glu Glu Ala Leu Lys Ala Phe His Glu Leu Asn Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
            355                 360                 365

Asn Leu Ser Gly Arg Gly Asp Lys Asp Leu Asp Ile Val Leu Lys Ala
            370                 375                 380

Ser Gly Asn Val
385

<210> SEQ ID NO 6
<211> LENGTH: 343
<212> TYPE: PRT
<213> ORGANISM: Thermotoga maritima

<400> SEQUENCE: 6

Met Ile Asp Leu Arg Ser Asp Thr Val Thr Lys Pro Thr Glu Glu Met
1               5                   10                  15
```

Arg Lys Ala Met Ala Gln Ala Glu Val Gly Asp Asp Val Tyr Gly Glu
               20                  25                  30

Asp Pro Thr Ile Asn Glu Leu Glu Arg Leu Ala Ala Glu Thr Phe Gly
           35                  40                  45

Lys Glu Ala Ala Leu Phe Val Pro Ser Gly Thr Met Gly Asn Gln Val
 50                  55                  60

Ser Ile Met Ala His Thr Gln Arg Gly Asp Glu Val Ile Leu Glu Ala
 65                  70                  75                  80

Asp Ser His Ile Phe Trp Tyr Glu Val Gly Ala Met Ala Val Leu Ser
                 85                  90                  95

Gly Val Met Pro His Pro Val Pro Gly Lys Asn Gly Ala Met Asp Pro
                100                 105                 110

Asp Asp Val Arg Lys Ala Ile Arg Pro Arg Asn Ile His Phe Pro Arg
            115                 120                 125

Thr Ser Leu Ile Ala Ile Glu Asn Thr His Asn Arg Ser Gly Gly Arg
130                 135                 140

Val Val Pro Leu Glu Asn Ile Lys Glu Ile Cys Thr Ile Ala Lys Glu
145                 150                 155                 160

His Gly Ile Asn Val His Ile Asp Gly Ala Arg Ile Phe Asn Ala Ser
                165                 170                 175

Ile Ala Ser Gly Val Pro Val Lys Glu Tyr Ala Gly Tyr Ala Asp Ser
            180                 185                 190

Val Met Phe Cys Leu Ser Lys Gly Leu Cys Ala Pro Val Gly Ser Val
            195                 200                 205

Val Val Gly Asp Arg Asp Phe Ile Glu Arg Ala Arg Lys Ala Arg Lys
            210                 215                 220

Met Leu Gly Gly Gly Met Arg Gln Ala Gly Val Leu Ala Ala Ala Gly
225                 230                 235                 240

Ile Ile Ala Leu Thr Lys Met Val Asp Arg Leu Lys Glu Asp His Glu
                245                 250                 255

Asn Ala Arg Phe Leu Ala Leu Lys Leu Lys Glu Ile Gly Tyr Ser Val
            260                 265                 270

Asn Pro Glu Asp Val Lys Thr Asn Met Val Ile Leu Arg Thr Asp Asn
            275                 280                 285

Leu Lys Val Asn Ala His Gly Phe Ile Glu Ala Leu Arg Asn Ser Gly
290                 295                 300

Val Leu Ala Asn Ala Val Ser Asp Thr Glu Ile Arg Leu Val Thr His
305                 310                 315                 320

Lys Asp Val Ser Arg Asn Asp Ile Glu Glu Ala Leu Asn Ile Phe Glu
                325                 330                 335

Lys Leu Phe Arg Lys Phe Ser
            340

<210> SEQ ID NO 7
<211> LENGTH: 389
<212> TYPE: PRT
<213> ORGANISM: Thermotoga maritima

<400> SEQUENCE: 7

Met Lys Gly Tyr Phe Gly Pro Tyr Gly Gly Gln Tyr Val Pro Glu Ile
 1               5                  10                  15

Leu Met Pro Ala Leu Glu Glu Leu Glu Ala Ala Tyr Glu Glu Ile Met
            20                  25                  30

Lys Asp Glu Ser Phe Trp Lys Glu Phe Asn Asp Leu Leu Arg Asp Tyr

```
                35                  40                  45
Ala Gly Arg Pro Thr Pro Leu Tyr Phe Ala Arg Arg Leu Ser Glu Lys
 50                  55                  60

Tyr Gly Ala Arg Ile Tyr Leu Lys Arg Glu Asp Leu Leu His Thr Gly
 65                  70                  75                  80

Ala His Lys Ile Asn Asn Ala Ile Gly Gln Val Leu Leu Ala Lys Lys
                 85                  90                  95

Met Gly Lys Thr Arg Ile Ile Ala Glu Thr Gly Ala Gly Gln His Gly
            100                 105                 110

Val Ala Thr Ala Thr Ala Ala Leu Phe Gly Met Glu Cys Val Ile
        115                 120                 125

Tyr Met Gly Glu Glu Asp Thr Ile Arg Gln Lys Pro Asn Val Glu Arg
        130                 135                 140

Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
        195                 200                 205

Lys Lys Gln Ile Leu Glu Lys Glu Gly Arg Leu Pro Asp Tyr Ile Val
    210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
        275                 280                 285

Val Gln Val Thr His Ser Val Ser Ala Gly Leu Asp Tyr Ser Gly Val
    290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
            340                 345                 350

Leu Lys Lys Ile Asn Ile Lys Gly Lys Val Val Val Asn Leu Ser
        355                 360                 365

Gly Arg Gly Asp Lys Asp Leu Glu Ser Val Leu Asn His Pro Tyr Val
    370                 375                 380

Arg Glu Arg Ile Arg
385

<210> SEQ ID NO 8
<211> LENGTH: 397
<212> TYPE: PRT
<213> ORGANISM: Archaeoglobus fulgidus

<400> SEQUENCE: 8

Met Arg Cys Trp Leu Glu Asn Leu Ser Gly Gly Arg Lys Met Lys Phe
 1                   5                  10                  15
```

-continued

Gly Glu Phe Gly Gly Arg Phe Val Pro Val Leu Ile Pro Pro Leu
                20                  25                  30

Glu Glu Leu Glu Lys Ala Tyr Asp Arg Phe Lys Asp Asp Glu Phe
            35                  40                  45

Lys Ala Arg Leu Glu Tyr Tyr Leu Lys Ser Tyr Ala Gly Arg Pro Thr
 50                  55                  60

Pro Leu Tyr Phe Ala Glu Asn Leu Ser Arg Glu Leu Gly Val Lys Ile
 65                  70                  75                  80

Tyr Leu Lys Arg Glu Asp Leu Leu His Gly Ala His Lys Ile Asn
                85                  90                  95

Asn Thr Ile Gly Gln Ala Leu Leu Ala Lys Phe Met Gly Lys Lys Arg
                100                 105                 110

Val Ile Ala Glu Thr Gly Ala Gly Gln His Gly Val Ala Thr Ala Met
            115                 120                 125

Ala Ala Ala Leu Leu Gly Leu Glu Ala Glu Ile Tyr Met Gly Ala Glu
            130                 135                 140

Asp Tyr Glu Arg Gln Lys Met Asn Val Phe Arg Met Glu Leu Leu Gly
145                 150                 155                 160

Ala Lys Val Thr Ala Val Glu Ser Gly Ser Arg Thr Leu Lys Asp Ala
                165                 170                 175

Ile Asn Glu Ala Leu Arg Asp Trp Val Glu Ser Phe Glu His Thr His
            180                 185                 190

Tyr Leu Ile Gly Ser Val Val Gly Pro His Pro Phe Pro Thr Ile Val
            195                 200                 205

Arg Asp Phe Gln Ala Val Ile Gly Lys Glu Ala Arg Arg Gln Ile Ile
210                 215                 220

Glu Ala Glu Gly Gly Met Pro Asp Ala Ile Ile Ala Cys Val Gly Gly
225                 230                 235                 240

Gly Ser Asn Ala Met Gly Ile Phe His Pro Phe Leu Asn Asp Val
                245                 250                 255

Arg Leu Ile Gly Val Glu Ala Gly Gly Glu Gly Ile Glu Ser Gly Arg
                260                 265                 270

His Ser Ala Ser Leu Thr Ala Gly Ser Lys Gly Val Leu His Gly Met
            275                 280                 285

Leu Ser Tyr Phe Leu Gln Asp Glu Glu Gly Met Met Leu Asp Thr His
            290                 295                 300

Ser Val Ser Ala Gly Leu Asp Tyr Pro Gly Val Gly Pro Glu His Ala
305                 310                 315                 320

Tyr Leu Lys Glu Thr Gly Arg Cys Glu Tyr Val Thr Val Asn Asp Glu
                325                 330                 335

Glu Ala Leu Arg Ala Phe Lys Thr Leu Ser Lys Leu Glu Gly Ile Ile
            340                 345                 350

Pro Ala Leu Glu Ser Ala His Ala Ile Ala Tyr Ala Met Lys Met Ala
            355                 360                 365

Glu Glu Met Gln Arg Asp Asp Val Leu Val Val Asn Leu Ser Gly Arg
            370                 375                 380

Gly Asp Lys Asp Met Asp Ile Val Arg Arg Leu Ala
385                 390                 395

<210> SEQ ID NO 9
<211> LENGTH: 397
<212> TYPE: PRT
<213> ORGANISM: Escherichia coli

<400> SEQUENCE: 9

-continued

```
Met Thr Thr Leu Leu Asn Pro Tyr Phe Gly Glu Phe Gly Met Tyr
 1               5                  10                 15

Val Pro Gln Ile Leu Met Pro Ala Leu Arg Gln Leu Glu Glu Ala Phe
                 20                  25                  30

Val Ser Ala Gln Lys Asp Pro Glu Phe Gln Ala Gln Phe Asn Asp Leu
             35                  40                  45

Leu Lys Asn Tyr Ala Gly Arg Pro Thr Ala Leu Thr Lys Cys Gln Asn
         50                  55                  60

Ile Thr Ala Gly Thr Asn Thr Thr Leu Tyr Leu Lys Arg Glu Asp Leu
 65                  70                  75                  80

Leu His Gly Gly Ala His Lys Thr Asn Gln Val Leu Gly Gln Ala Leu
                 85                  90                  95

Leu Ala Lys Arg Met Gly Lys Thr Glu Ile Ile Ala Glu Thr Gly Ala
            100                 105                 110

Gly Gln His Gly Val Ala Ser Ala Leu Ala Ser Ala Leu Leu Gly Leu
            115                 120                 125

Lys Cys Arg Ile Tyr Met Gly Ala Lys Asp Val Glu Arg Gln Ser Pro
130                 135                 140

Asn Val Phe Arg Met Arg Leu Met Gly Ala Glu Val Ile Pro Val His
145                 150                 155                 160

Ser Gly Ser Ala Thr Leu Lys Asp Ala Cys Asn Glu Ala Leu Arg Asp
                165                 170                 175

Trp Ser Gly Ser Tyr Glu Thr Ala His Tyr Met Leu Gly Thr Ala Ala
                180                 185                 190

Gly Pro His Pro Tyr Pro Thr Ile Val Arg Glu Phe Gln Arg Met Ile
            195                 200                 205

Gly Glu Glu Thr Lys Ala Gln Ile Leu Glu Arg Glu Gly Arg Leu Pro
210                 215                 220

Asp Ala Val Ile Ala Cys Val Gly Gly Gly Ser Asn Ala Ile Gly Met
225                 230                 235                 240

Phe Ala Asp Phe Ile Asn Glu Thr Asn Val Gly Leu Ile Gly Val Glu
                245                 250                 255

Pro Gly Gly His Gly Ile Glu Thr Gly Glu His Gly Ala Pro Leu Lys
            260                 265                 270

His Gly Arg Val Gly Ile Tyr Phe Gly Met Lys Ala Pro Met Met Gln
275                 280                 285

Thr Glu Asp Gly Gln Ile Glu Glu Ser Tyr Ser Ile Ser Ala Gly Leu
290                 295                 300

Asp Phe Pro Ser Val Gly Pro Gln His Ala Tyr Leu Asn Ser Thr Gly
305                 310                 315                 320

Arg Ala Asp Tyr Val Ser Ile Thr Asp Asp Glu Ala Leu Glu Ala Phe
                325                 330                 335

Lys Thr Leu Cys Leu His Glu Gly Ile Ile Pro Ala Leu Glu Ser Ser
            340                 345                 350

His Ala Leu Ala His Ala Leu Lys Met Met Arg Glu Asn Pro Asp Lys
            355                 360                 365

Glu Gln Leu Leu Val Val Asn Leu Ser Gly Arg Gly Asp Lys Asp Ile
370                 375                 380

Phe Thr Val His Asp Ile Leu Lys Ala Arg Gly Glu Ile
385                 390                 395
```

<210> SEQ ID NO 10
<211> LENGTH: 41

```
<212> TYPE: DNA
<213> ORGANISM: Artificial Sequence
<220> FEATURE:
<223> OTHER INFORMATION: Synthetic Construct

<400> SEQUENCE: 10
gaaataattt tgtttaactt taagaaggag atatacatat g                41

<210> SEQ ID NO 11
<211> LENGTH: 35
<212> TYPE: DNA
<213> ORGANISM: Artificial Sequence
<220> FEATURE:
<223> OTHER INFORMATION: Synthetic Construct

<400> SEQUENCE: 11
gccggatctc agtggtggtg gtggtggtgc tcgag                       35

<210> SEQ ID NO 12
<211> LENGTH: 41
<212> TYPE: DNA
<213> ORGANISM: Artificial Sequence
<220> FEATURE:
<223> OTHER INFORMATION: Synthetic Construct

<400> SEQUENCE: 12
catatgtata tctccttctt aaagttaaac aaaattattt c                41

<210> SEQ ID NO 13
<211> LENGTH: 35
<212> TYPE: DNA
<213> ORGANISM: Artificial Sequence
<220> FEATURE:
<223> OTHER INFORMATION: Synthetic Construct

<400> SEQUENCE: 13
ctcgagcacc accaccacca ccactgagat ccggc                       35

<210> SEQ ID NO 14
<211> LENGTH: 41
<212> TYPE: DNA
<213> ORGANISM: Artificial Sequence
<220> FEATURE:
<223> OTHER INFORMATION: Synthetic Construct

<400> SEQUENCE: 14
gaaataattt tgtttaactt taagaaggag atatacatat g                41

<210> SEQ ID NO 15
<211> LENGTH: 26
<212> TYPE: DNA
<213> ORGANISM: Artificial Sequence
<220> FEATURE:
<223> OTHER INFORMATION: Synthetic Construct

<400> SEQUENCE: 15
ccagaaacgc tgrtagracc cctgaa                                 26

<210> SEQ ID NO 16
<211> LENGTH: 33
<212> TYPE: DNA
<213> ORGANISM: Artificial Sequence
<220> FEATURE:
<223> OTHER INFORMATION: Synthetic Construct

<400> SEQUENCE: 16
```

```
ggctctgcgt gattgggwag ctactttga ata                          33
```

<210> SEQ ID NO 17
<211> LENGTH: 32
<212> TYPE: DNA
<213> ORGANISM: Artificial Sequence
<220> FEATURE:
<223> OTHER INFORMATION: Synthetic Construct

<400> SEQUENCE: 17

```
gtgctgaata cgtgrcagta accgatgaag aa                          32
```

<210> SEQ ID NO 18
<211> LENGTH: 41
<212> TYPE: DNA
<213> ORGANISM: Artificial Sequence
<220> FEATURE:
<223> OTHER INFORMATION: Synthetic Construct

<400> SEQUENCE: 18

```
gaaataattt tgtttaactt taagaaggag atatacatat g                41
```

<210> SEQ ID NO 19
<211> LENGTH: 29
<212> TYPE: DNA
<213> ORGANISM: Artificial Sequence
<220> FEATURE:
<223> OTHER INFORMATION: Synthetic Construct

<400> SEQUENCE: 19

```
cggtggtgct aaartatacc tgaaacgtg                              29
```

<210> SEQ ID NO 20
<211> LENGTH: 32
<212> TYPE: DNA
<213> ORGANISM: Artificial Sequence
<220> FEATURE:
<223> OTHER INFORMATION: Synthetic Construct

<400> SEQUENCE: 20

```
ggtcaggttg gtgtgtykca tggcatgctg tc                          32
```

<210> SEQ ID NO 21
<211> LENGTH: 33
<212> TYPE: DNA
<213> ORGANISM: Artificial Sequence
<220> FEATURE:
<223> OTHER INFORMATION: Synthetic Construct

<400> SEQUENCE: 21

```
gatattgtcc tgaaagyatc tggcaacgtg ctc                         33
```

<210> SEQ ID NO 22
<211> LENGTH: 26
<212> TYPE: DNA
<213> ORGANISM: Artificial Sequence
<220> FEATURE:
<223> OTHER INFORMATION: Synthetic Construct

<400> SEQUENCE: 22

```
ttcaggggty ctaycagcgt ttctgg                                 26
```

<210> SEQ ID NO 23
<211> LENGTH: 33
<212> TYPE: DNA
<213> ORGANISM: Artificial Sequence

```
<220> FEATURE:
<223> OTHER INFORMATION: Synthetic Construct

<400> SEQUENCE: 23
tattcaaaag tagctwccca atcacgcaga gcc                                33

<210> SEQ ID NO 24
<211> LENGTH: 32
<212> TYPE: DNA
<213> ORGANISM: Artificial Sequence
<220> FEATURE:
<223> OTHER INFORMATION: Synthetic Construct

<400> SEQUENCE: 24
ttcttcatcg gttactgyca cgtattcagc ac                                 32

<210> SEQ ID NO 25
<211> LENGTH: 35
<212> TYPE: DNA
<213> ORGANISM: Artificial Sequence
<220> FEATURE:
<223> OTHER INFORMATION: Synthetic Construct

<400> SEQUENCE: 25
gccggatctc agtggtggtg gtggtggtgc tcgag                              35

<210> SEQ ID NO 26
<211> LENGTH: 29
<212> TYPE: DNA
<213> ORGANISM: Artificial Sequence
<220> FEATURE:
<223> OTHER INFORMATION: Synthetic Construct

<400> SEQUENCE: 26
cacgtttcag gtatayttta gcaccaccg                                     29

<210> SEQ ID NO 27
<211> LENGTH: 32
<212> TYPE: DNA
<213> ORGANISM: Artificial Sequence
<220> FEATURE:
<223> OTHER INFORMATION: Synthetic Construct

<400> SEQUENCE: 27
gacagcatgc catgmracac accaacctga cc                                 32

<210> SEQ ID NO 28
<211> LENGTH: 33
<212> TYPE: DNA
<213> ORGANISM: Artificial Sequence
<220> FEATURE:
<223> OTHER INFORMATION: Synthetic Construct

<400> SEQUENCE: 28
gagcacgttg ccagatrctt tcaggacaat atc                                33

<210> SEQ ID NO 29
<211> LENGTH: 35
<212> TYPE: DNA
<213> ORGANISM: Artificial Sequence
<220> FEATURE:
<223> OTHER INFORMATION: Synthetic Construct

<400> SEQUENCE: 29
gccggatctc agtggtggtg gtggtggtgc tcgag                              35
```

```
<210> SEQ ID NO 30
<211> LENGTH: 33
<212> TYPE: DNA
<213> ORGANISM: Artificial Sequence
<220> FEATURE:
<223> OTHER INFORMATION: Synthetic Construct

<400> SEQUENCE: 30
ccggttctcg caccgggaaa gacgcaatca acg                                    33

<210> SEQ ID NO 31
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (32)..(32)
<223> OTHER INFORMATION: n = A, C, G, or T
<220> FEATURE:
<221> NAME/KEY: misc_feature
<222> LOCATION: (33)..(33)
<223> OTHER INFORMATION: n = A, G, or T
<220> FEATURE:
<221> NAME/KEY: misc_feature
<222> LOCATION: (34)..(34)
<223> OTHER INFORMATION: n = T

<400> SEQUENCE: 31
cgtaattcca gttaactccg gttctcgcac cnnnaaagac gcaatcaacg                  50

<210> SEQ ID NO 32
<211> LENGTH: 23
<212> TYPE: DNA
<213> ORGANISM: Artificial Sequence
<220> FEATURE:
<223> OTHER INFORMATION: Synthetic Construct

<400> SEQUENCE: 32
ttctcgcacc gtgaaagacg caa                                               23

<210> SEQ ID NO 33
<211> LENGTH: 32
<212> TYPE: DNA
<213> ORGANISM: Artificial Sequence
<220> FEATURE:
<223> OTHER INFORMATION: Synthetic Construct

<400> SEQUENCE: 33
ggccaagagc gtgcccttc tgcgttagtt gc                                      32

<210> SEQ ID NO 34
<211> LENGTH: 36
<212> TYPE: DNA
<213> ORGANISM: Artificial Sequence
<220> FEATURE:
<223> OTHER INFORMATION: Synthetic Construct

<400> SEQUENCE: 34
ggtgcgagaa ccggagttaa ctggaattac gtttgc                                 36

<210> SEQ ID NO 35
<211> LENGTH: 25
<212> TYPE: DNA
<213> ORGANISM: Artificial Sequence
<220> FEATURE:
<223> OTHER INFORMATION: Synthetic Construct
```

```
<400> SEQUENCE: 35
ccggagttaa ctggaattac gtttg                                          25

<210> SEQ ID NO 36
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (32)..(32)
<223> OTHER INFORMATION: n = A, C, or G
<220> FEATURE:
<221> NAME/KEY: misc_feature
<222> LOCATION: (33)..(33)
<223> OTHER INFORMATION: n = A, C, or T
<220> FEATURE:
<221> NAME/KEY: misc_feature
<222> LOCATION: (34)..(34)
<223> OTHER INFORMATION: n = G

<400> SEQUENCE: 36
cgtaattcca gttaactccg gttctcgcac cnnnaaagac gcaatcaacg               50

<210> SEQ ID NO 37
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (32)..(32)
<223> OTHER INFORMATION: n = T
<220> FEATURE:
<221> NAME/KEY: misc_feature
<222> LOCATION: (33)..(33)
<223> OTHER INFORMATION: n = G
<220> FEATURE:
<221> NAME/KEY: misc_feature
<222> LOCATION: (34)..(34)
<223> OTHER INFORMATION: n = G

<400> SEQUENCE: 37
cgtaattcca gttaactccg gttctcgcac cnnnaaagac gcaatcaacg               50
```